United States Patent [19]

Audia et al.

[11] Patent Number: 6,096,782
[45] Date of Patent: Aug. 1, 2000

[54] N-(ARYL/HETEROARYL) AMINO ACID DERIVATIVES PHARMACEUTICAL COMPOSITIONS COMPRISING SAME AND METHODS FOR INHIBITING β-AMYLOID PEPTIDE RELEASE AND/OR ITS SYNTHESIS BY USE OF SUCH COMPOUNDS

[75] Inventors: James E. Audia, Indianapolis, Ind.; Beverly K. Folmer, Newark, Del.; Varghese John, San Francisco; Lee H. Latimer, Oakland, both of Calif.; Jeffrey S. Nissen; Warren J. Porter, both of Indianapolis, Ind.; Eugene D. Thorsett, Moss Beach; Jing Wu, San Mateo, both of Calif.

[73] Assignees: Athena Neurosciences, Inc., South San Francisco, Calif.; Eli Lilly & Company, Indianapolis, Ind.

[21] Appl. No.: 08/976,191

[22] Filed: Nov. 21, 1997

Related U.S. Application Data

[60] Provisional application No. 60/077,175, Nov. 22, 1996.
[51] Int. Cl.$^7$ .......................... A01N 37/20; A01N 43/50; C07C 229/24; C07D 233/61
[52] U.S. Cl. ...................... 514/506; 514/399; 548/335.5; 560/41
[58] Field of Search .............................. 560/41; 514/506, 514/399; 548/335.5

[56] References Cited

U.S. PATENT DOCUMENTS 5,536,737  7/1996  Kobayashi et al. .................... 514/365
5,552,415  9/1996  May ........................................ 514/324

FOREIGN PATENT DOCUMENTS

| 0 778 266 | 6/1997 | European Pat. Off. . |
|---|---|---|
| WO 95/09838 | 4/1995 | WIPO . |
| WO 96/20725 | 7/1996 | WIPO . |
| WO 96/22966 | 8/1996 | WIPO . |

OTHER PUBLICATIONS

Database CAPLUS on STN, No. 94:133017, Kourai, 'Antimicrobial activities of amino acid derivatives 2. Antimicrobial activities of N–p–chlorophenylglycyl–D,L–alanine and N–p–chlorophenylglycyl–L–leucine.' abstract of Bokin Bobai (1980), 8(12), pp. 517–525.

Iwakura, et al., "Reaction of Alkylidenepseudoxazolones With Amines", Tetrahedron, vol. 24, pp. 575–583, 1968.

Papadopoulos, et al., Tetrahedron, 47(4/5):563–572 (1991).

Waldmann, et al., Tetrahedron Letters, 37(48):8725–8728 (1996).

*Primary Examiner*—Brian M. Burn
*Assistant Examiner*—Brian J. Davis
*Attorney, Agent, or Firm*—Burns, Doane, Swecker & Mathis, LLP

[57] ABSTRACT

Disclosed are compounds which inhibit β-amyloid peptide release and/or its synthesis, and, accordingly, have utility in treating Alzheimer's disease. Also disclosed are pharmaceutical compositions comprising a compound which inhibits β-amyloid peptide release and/or its synthesis as well as methods for treating Alzheimer's disease both prophylactically and therapeutically with such pharmaceutical compositions.

27 Claims, No Drawings

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
       (A) LENGTH: 43 amino acids
       (B) TYPE: amino acid
       (D) TOPOLOGY: linear (ii) MOLECULE TYPE: peptide (xi) SEQUENCE DESCRIPTION: SEQ ID NO:1:

```
Asp Ala Glu Phe Arg His Asp Ser Gly Tyr Glu Val His His
 1               5                  10

Gln Lys Leu Val Phe Phe Ala Glu Asp Val Gly Ser Asn Lys
15                  20                  25

Gly Ala Ile Ile Gly Leu Met Val Gly Gly Val Val Ile Ala
    30                  35                  40

Thr
```

N-(ARYL/HETEROARYL) AMINO ACID DERIVATIVES PHARMACEUTICAL COMPOSITIONS COMPRISING SAME AND METHODS FOR INHIBITING β-AMYLOID PEPTIDE RELEASE AND/OR ITS SYNTHESIS BY USE OF SUCH COMPOUNDS

CROSS-REFERENCE TO RELATED APPLICATIONS

This application claims the benefit of U.S. Provisional Application No. 60/077,175, which was converted pursuant to 37 C.F.R. § 1.53(b)(2)(ii) from U.S. patent application Ser. No. 08/755,334, filed Nov. 22, 1996, which is incorporated herein by reference in its entirety.

BACKGROUND OF THE INVENTION

1. Field of the Invention

This invention relates to compounds which inhibit β-amyloid peptide release and/or its synthesis, and, accordingly, have utility in treating Alzheimer's disease. This invention also relates to pharmaceutical compositions comprising such compounds as well as methods for inhibiting release of β-amyloid peptide.

2. References

The following publications, patents and patent applications are cited in this application as superscript numbers:

[1] Glenner, et al., "Alzheimer's Disease: Initial Report of the Purification and Characterization of a Novel Cerebrovascular Amyloid Protein", *Biochem. Biophys. Res. Commun.*, 120:885–890 (1984).

[2] Glenner, et al., "Polypeptide Marker for Alzheimer's Disease and its Use for Diagnosis", U.S. Pat. No. 4,666,829 issued May 19, 1987.

[3] Selkoe, "The Molecular Pathology of Alzheimer's Disease", *Neuron*, 6:487–498 (1991).

[4] Goate, et al., "Segregation of a Missense Mutation in the Amyloid Precursor Protein Gene with Familial Alzheimer's Disease", *Nature*, 349:704–706 (1990).

[5] Chartier-Harlan, et al., "Early-Onset Alzheimer's Disease Caused by Mutations at Codon 717 of the β-Amyloid Precursor Protein Gene", *Nature*, 3:844–846 (1989).

[6] Murrell, et al., "A Mutation in the Amyloid Precursor Protein Associated with Hereditary Alzheimer's Disease", *Science*, 254:97–99 (1991).

[7] Mullan, et al., "A Pathogenic Mutation for Probable Alzheimer's Disease in the APP Gene at the N-Terminus of β-Amyloid, *Nature Genet.*, 1:345–347 (1992).

[8] Schenk, et al., "Methods and Compositions for the Detection of Soluble β-Amyloid Peptide", International Patent Application Publication No. WO 94/10569, published May 11, 1994.

[9] Selkoe, "Amyloid Protein and Alzheimer's Disease", *Scientific American*, pp. 2–8, November, 1991.

[10] Yates, et al., "N,N-Disubstituted Amino Acid Herbicides", U.S. Pat. No. 3,598,859, issued Aug. 10, 1971.

[11] Citron, et al., "Mutation of the β-Amyloid Precursor Protein in Familial Alzheimer's Disease Increases β-Protein Production, *Nature*, 360:672–674 (1992).

[12] Hansen, et al., "Reexamination and Further Development of a Precise and Rapid Dye Method for Measuring Cell Growth/Cell Kill", *J. Immun. Meth.*, 119:203–210 (1989).

All of the above publications, patents and patent applications are herein incorporated by reference in their entirety to the same extent as if each individual publication, patent or patent application was specifically and individually indicated to be incorporated by reference in its entirety.

State of the Art

Alzheimer's Disease (AD) is a degenerative brain disorder characterized clinically by progressive loss of memory, cognition, reasoning, judgment and emotional stability that gradually leads to profound mental deterioration and ultimately death. AD is a very common cause of progressive mental failure (dementia) in aged humans and is believed to represent the fourth most common medical cause of death in the United States. AD has been observed-in races and ethnic groups worldwide and presents a major present and future public health problem. The disease is currently estimated to affect about two to three million individuals in the United States alone. AD is at present incurable. No treatment that effectively prevents AD or reverses its symptoms and course is currently known.

The brains of individuals with AD exhibit characteristic lesions termed senile (or amyloid) plaques, amyloid angiopathy (amyloid deposits in blood vessels) and neurofibrillary tangles. Large numbers of these lesions, particularly amyloid plaques and neurofibrillary tangles, are generally found in several areas of the human brain important for memory and cognitive function in patients with AD. Smaller numbers of these lesions in a more restrictive anatomical distribution are also found in the brains of most aged humans who do not have clinical AD. Amyloid plaques and amyloid angiopathy also characterize the brains of individuals with Trisomy 21 (Down's Syndrome) and Hereditary Cerebral Hemorrhage with Amyloidosis of the Dutch Type (HCHWA-D). At present, a definitive diagnosis of AD usually requires observing the aforementioned lesions in the brain tissue of patients who have died with the disease or, rarely, in small biopsied samples of brain tissue taken during an invasive neurosurgical procedure.

The principal chemical constituent of the amyloid plaques and vascular amyloid deposits (amyloid angiopathy) characteristic of AD and the other disorders mentioned above is an approximately 4.2 kilodalton (kD) protein of about 39–43 amino acids designated the β-amyloid peptide (βAP) or sometimes Aβ, AβP or β/A4. β-Amyloid peptide was first purified and a partial amino acid sequence was provided by Glenner, et al.[1] The isolation procedure and the sequence data for the first 28 amino acids are described in U.S. Pat. No. 4,666,829[2].

Molecular biological and protein chemical analyses have shown that the β-amyloid peptide is a small fragment of a much larger precursor protein (APP), that is normally produced by cells in many tissues of various animals, including humans. Knowledge of the structure of the gene encoding the APP has demonstrated that β-amyloid peptide arises as a peptide fragment that is cleaved from APP by protease enzyme(s). The precise biochemical mechanism by which the β-amyloid peptide fragment is cleaved from APP and subsequently deposited as amyloid plaques in the cerebral tissue and in the walls of the cerebral and meningeal blood vessels is currently unknown.

Several lines of evidence indicate that progressive cerebral deposition of β-amyloid peptide plays a seminal role in the pathogenesis of AD and can precede cognitive symptoms by years or decades. See, for example, Selkoe[3]. The most important line of evidence is the discovery that missense DNA mutations at amino acid 717 of the 770-amino acid isoform of APP can be found in affected members but not unaffected members of several families with a genetically determined (familial) form of AD (Goate, et al.[4]; Chartier Harlan, et al.[5]; and Murrell, et al.[6]) and is referred to as the Swedish variant. A double mutation changing lysine$^{595}$-methionine$^{596}$ to asparagine$^{595}$-leucine$^{596}$ (with reference to the 695 isoform) found in a Swedish family was reported in 1992 (Mullan, et al.[7]). Genetic linkage analyses have demonstrated that these mutations, as well as certain other mutations in the APP gene, are the specific molecular cause of AD in the affected members of such families. In addition, a mutation at amino acid 693 of the 770-amino acid isoform of APP has been identified as the cause of the β-amyloid peptide deposition disease, HCHWA-D, and a change from alanine to glycine at amino acid 692 appears to cause a phenotype that resembles AD is some patients but HCHWA-D in others. The discovery of these and other mutations in APP in genetically based cases of AD prove that alteration of APP and subsequent deposition of its β-amyloid peptide fragment can cause AD.

Despite the progress which has been made in understanding the underlying mechanisms of AD and other β-amyloid peptide related diseases, there remains a need to develop methods and compositions for treatment of the disease(s). Ideally, the treatment methods would advantageously be based on drugs which are capable of inhibiting β-amyloid peptide release and/or its synthesis.

SUMMARY OF THE INVENTION

This invention is directed to the discovery of a class of compounds which inhibit β-amyloid peptide release and/or its synthesis and, therefore, are useful in the prevention of AD in patients susceptible to AD and/or in the treatment of patients with AD in order to inhibit further deterioration in their condition. The class of compounds having the described properties are defined by formula I below:

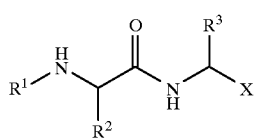

I wherein:
$R^1$ is selected from the group consisting of
(a) phenyl,
(b) a substituted phenyl group of formula II:

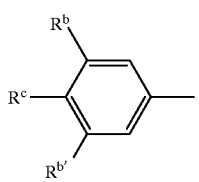

II wherein $R^c$ is selected from the group consisting of acyl, alkyl, alkoxy, alkylalkoxy, azido, cyano, halo, hydrogen, nitro, trihalomethyl, thioalkoxy, and wherein $R^b$ and $R^c$ are fused to form a heteroaryl or heterocyclic ring with the phenyl ring, $R^b$ and $R^{b'}$ are independently selected from the group consisting of hydrogen, halo, nitro, cyano, trihalomethyl, alkoxy, and thioalkoxy with the proviso that when $R^c$ is hydrogen, then $R^b$ and $R^{b'}$ are either both hydrogen or both substituents other than hydrogen,
(c) 2-naphthyl,
(d) 2-naphthyl substituted at the 4, 5, 6, 7 and/or 8 positions with 1 to 5 substituents selected from the group consisting of alkyl, alkoxy, halo, cyano, nitro, trihalomethyl, thioalkoxy, aryl, and heteroaryl,
(e) heteroaryl, and
(f) substituted heteroaryl containing 1 to 3 substituents selected from the group consisting of alkyl, alkoxy, aryl, aryloxy, cyano, halo, nitro, heteroaryl, thioalkoxy and thioaryloxy provided that said substituents are not ortho (adjacent) to the heteroaryl attachment to the —NH group;

$R^2$ is selected from the group consisting of hydrogen, alkyl of from 1 to 4 carbon atoms, alkylalkoxy of from 1 to 4 carbon atoms, alkylthioalkoxy of from 1 to 4 carbon atoms, aryl, heteroaryl, substituted aryl and substituted heteroaryl provided that the substituents are not ortho (adjacent) to the attachment of the aryl or heteroaryl atom to the carbon atom;

$R^3$ is selected from the group consisting of alkyl, alkenyl, alkynyl, aryl, cycloalkyl, cycloalkenyl, heteroaryl, substituted alkyl, substituted alkenyl, substituted alkynyl, and heterocyclic;

X is —C(O)Y where Y is selected from the group consisting of
(a) alkyl,
(b) substituted alkyl with the proviso that the substitution on said substituted alkyl does not include α-haloalkyl, α-diazoalkyl or α-OC(O)alkyl groups,
(c) alkoxy or thioalkoxy,
(d) substituted alkoxy or substituted thioalkoxy,
(e) hydroxy,
(f) aryl,
(g) heteroaryl,
(h) heterocyclic,
(i) —NR'R" where R' and R" are independently selected from the group consisting of hydrogen, alkyl, substituted alkyl, cycloalkyl, aryl, heteroaryl, heterocyclic, and where R' and R" are joined to form a cyclic group having from 2 to 8 carbon atoms optionally containing 1 to 2 additional heteroatoms selected from the group consisting of oxygen, sulfur and nitrogen and optionally substituted with one or more alkyl or alkoxy groups, and when $R^3$ contains at least 3 carbon atoms, X can also be —CR$^4$R$^4$Y' where each $R^4$ is independently selected from the group consisting of hydrogen, alkyl, cycloalkyl, aryl, heteroaryl and heterocyclic and Y' is selected from the group consisting of hydroxyl, amino, thiol, —OC(O)R$^5$, —SSR$^5$, —SSC(O)R$^5$ where $R^5$ is selected from the group consisting of alkyl, substituted alkyl, cycloalkyl, aryl, heteroaryl and heterocyclic, and with the proviso that when $R^1$ is 3,4-dichlorophenyl, $R^2$ is methyl, and $R^3$ is benzyl derived from D-phenylalanine, then X is not —C(O)OCH$_3$.

Accordingly, in one of its method aspects, this invention is directed to a method for inhibiting β-amyloid peptide release and/or its synthesis in a cell which method comprises administering to such a cell an amount of a compound or a mixture of compounds of formula I above effective in inhibiting the cellular release and/or synthesis of β-amyloid peptide.

Because the in vivo generation of β-amyloid peptide is associated with the pathogenesis of AD[8,9], the compounds of formula I can also be employed in conjunction with a pharmaceutical composition to prophylactically and/or therapeutically prevent and/or treat AD. Accordingly, in another of its method aspects, this invention is directed to a prophylactic method for preventing the onset of AD in a patient at risk for developing AD which method comprises administering to said patient a pharmaceutical composition comprising a pharmaceutically inert carrier and an effective amount of a compound or a mixture of compounds of formula I above.

In yet another of its method aspects, this invention is directed to a therapeutic method for treating a patient with AD in order to inhibit further deterioration in the condition of that patient which method comprises administering to said patient a pharmaceutical composition comprising a pharmaceutically inert carrier and an effective amount of a compound or a mixture of compounds of formula I above.

In formula I above, $R^1$ substituted phenyls are preferably 4-substituted, 3,5-disubstituted or 3,4-disubstituted phenyl substituents wherein the substituents at the 3 and/or 5 positions are defined by $R^b$, $R^{b'}$ as above and the substituents at the 4 position is defined by $R^c$ as above. Particularly preferred 3,5-disubstituted phenyls include, by way of example, 3,5-dichlorophenyl, 3,5-difluorophenyl, 3,5-di(trifluoromethyl)phenyl, 3,5-dimethoxyphenyl, and the like. Particularly, preferred 3,4-disubstituted phenyls include, by way of example, 3,4-dichlorophenyl, 3,4-difluorophenyl, 3-(trifluoromethyl)-4-chlorophenyl, 3-chloro-4-cyanophenyl, 3-chloro-4-iodophenyl, 3,4-methylenedioxyphenyl, and the like. Particularly preferred 4-substituted phenyls include, by way of example, 4-azidophenyl, 4-bromophenyl, 4-chlorophenyl, 4-cyanophenyl, 4-ethylphenyl, 4-fluorophenyl, 4-iodophenyl, 4-(phenylcarbonyl)phenyl, 4-(1-ethoxy)ethylphenyl, and the like.

Other preferred $R^1$ substituents include, by way of example, 2-naphthyl, quinolin-3-yl, 2-methylquinolin-6-yl, benzothiazol-6-yl, benzothiazol-2-yl, 5-indolyl, phenyl, 2-naphthyl, and the like.

Preferably $R^2$ is selected from the group consisting of alkyl of from 1 to 4 carbon atoms, alkylalkoxy of from 1 to 4 carbon atoms, alkylthioalkoxy of from 1 to 4 carbon atoms, aryl, heteroaryl, substituted aryl and substituted heteroaryl provided that the substituents are not ortho to the attachment of the aryl or heteroaryl atom to the carbon atom. Particularly preferred $R^2$ substituents include, by way of example, methyl, ethyl, n-propyl, iso-propyl, n-butyl, iso-butyl, —$CH_2CH_2SCH_3$, phenyl and the like.

Preferred $R^3$ substituents include alkyl groups such as methyl, ethyl, n-propyl, iso-propyl, n-butyl, iso-butyl, sec-butyl, and the like; substituted alkyl groups such as α-hydroxyethyl, —$CH_2$-cyclohexyl, benzyl, p-hydroxybenzyl, 3-iodo-4-hydroxybenzyl, 3,5-diiodo-4-hydroxybenzyl, —$CH_2$-indol-3-yl, phenyl, —$(CH_2)_4$—NH-BOC, —$(CH_2)_4$—$NH_2$, —$CH_2$-(1-N-benzyl-imidazol-4-yl), —$CH_2$-imidazol-4-yl, —$CH_2CH_2SCH_3$, —$(CH_2)_4$NCH(O)$(CH_2)_4CH_3$, —$(CH_2)_yC(O)OR^5$ where y is 1 or 2 and $R^5$ is hydrogen, methyl, tert-butyl, phenyl, and the like.

Preferred X substituents include —C(O)Y groups where Y is methoxy, ethyoxy, n-propoxy, iso-propoxy, n-butoxy, iso-butoxy, tert-butoxy, amino (—$NH_2$), N-(iso-butyl)amino, N-methylamino, N,N-dimethylamino, N-benzylamino, and the like as well as where X is —$CH_2OH$ and the like.

This invention also provides for novel pharmaceutical compositions comprising a pharmaceutically inert Tier and a compound of the formula I above.

Particularly preferred compounds for use in the methods and compositions of this invention include, by way of example, the following wherein the stereochemistry of the $R^2$ and $R^3$ groups is preferably derived from the L-amino acid:

N-[N-(3,4-dichlorophenyl)alanyl]valine methyl ester
N-[N-(3,4-dichlorophenyl)alanyl]valine N-iso-butyl amide
N-[N-(3,4-dichlorophenyl)alanyl]threonine methyl ester
N-[N-(3,4-dichlorophenyl)alanyl]valine ethyl ester
N-[N-(3,4-dichlorophenyl)alanyl]valine tert-butyl ester
N-[N-(3,4-dichlorophenyl)alanyl]valine amide
N-(3,4-dichlorophenyl)alanine N-(1-hydroxy-3-methyl-2-butyl) amide
N-[N-(3,4-dichlorophenyl)alanyl]valine N,N-dimethyl amide
N-[N-(3,4-dichlorophenyl)alanyl]valine N-methyl amide
N-[N-(3,4-dichlorophenyl)alanyl]alanine methyl ester
N-[N-(3,4-dichlorophenyl)alanyl]leucine methyl ester
N-[N-(3,4-dichlorophenyl)alanyl]phenylalanine methyl ester
N-[N-(3,4-dichlorophenyl)alanyl]isoleucine methyl ester
N-[N-(3,4-dichlorophenyl)alanyl]-2-aminopentanoic acid methyl ester
N-[N-(3,4-dichlorophenyl)alanyl]-2-aminohexanoic acid methyl ester
N-[N-(3,4-dichlorophenyl)alanyl]tryptophan methyl ester
N-[N-(3,4-dichlorophenyl)alanyl]aspartic acid α-methyl ester
N-[N-(3,4-dichlorophenyl)alanyl]aspartic acid β-(tert-butyl ester)α-methyl ester
N-[N-(3,4-dichlorophenyl)alanyl]-N-BOC-lysine methyl ester
N-[N-benzothiazol-6-yl)alanyl]-2-aminohexanoic acid methyl ester
N-[N-(3,4-dichlorophenyl)alanyl]lysine methyl ester
N-[N-(3,4-dichlorophenyl)alanyl]tyrosine methyl ester
N-[N-(3,5-dichlorophenyl)alanyl]alanine methyl ester
N-[N-(3,5-dichlorophenyl)alanyl]-2-aminopentanoic acid methyl ester
N-[N-(3,5-dichlorophenyl)alanyl]phenylalanine methyl ester
N-[N-(3,4-dichlorophenyl)alanyl]aspartic acid β-(methyl ester)α-methyl ester
N-[N-(3,4-dichlorophenyl)alanyl]-1-benzylhistidine methyl ester
N-[N-(3,4-dichlorophenyl)alanyl]glutamic acid γ-(tert-butyl ester)α-methyl ester
N-[N-(3,4-dichlorophenyl)alanyl]leucine amide
N-[N-(3,4-dichlorophenyl)alanyl]glutamic acid α-methyl ester
N-[N-(3,4-dichlorophenyl)alanyl]-(3,5-diiodo)tyrosine methyl ester
N-[N-(3,4-dichlorophenyl)alanyl]-(3-iodo)tyrosine methyl ester N-[N-(3,5-dichlorophenyl)glycyl]-2-aminopentanoic acid methyl ester N-[N-(3,4-dichlorophenyl)alanyl]-Nε-(hexanoyl)lysine methyl ester N-[N-(3,4-dichlorophenyl)alanyl]phenylalanine amide N-[N-(3,4-dichlorophenyl)alanyl]-2-aminohexan-(N-methyl)-amide N-[N-(3,4-dichlorophenyl)alanyl]-β-cyclohexylalanine methyl ester N-[N-(3,4-dichlorophenyl)alanyl]-2-aminohexanamide N-[N-(3,4-dichlorophenyl)alanyl]-2-aminohexan-(N,N-dimethyl)-amide N-[N-(3,4-dichlorophenyl)alanyl]methionine methyl ester N-[N-(3,5-dichlorophenyl)alanyl]-2-aminohexan-(N,N-dimethyl)-amide N-[N-(3,5-dichlorophenyl)alanyl]-2-aminohexanamide N-[N-(3,5-dichlorophenyl)alanyl]-2-aminohexan-(N-methyl)-amide N-[N-(3,4-dichlorophenyl)alanyl]histidine methyl ester N-[N-(quinolin-3-yl)alanyl]-2-aminohexanoic acid methyl ester N-[N-(benzothiazol-2-yl)alanyl]-2-aminohexanoic acid methyl ester N-[N-(3,5-difluorophenyl)alanyl]alanine methyl ester N-[N-(3,5-difluorophenyl)alanyl]-2-aminohexanoic acid methyl ester N-[N-(3,4-dichlorophenyl)alanyl]-2-aminohexanamide N-[N-(3,4-dichlorophenyl)alanyl]-2-aminohexan-(N-benzyl)-amide N-[N-(3,4-dichlorophenyl)alanyl]-2-amino-2-phenylethanol N-[N-(3,5-dichlorophenyl)phenylglycinyl]alanine methyl ester N-[N-(3,4-dichlorophenyl)alanyl]-2-aminohexanol N-[N-(3,5-dichlorophenyl)alanyl]-2-amino-2-phenylethanol N-[N-(3,5-dichlorophenyl)alanyl]-phenylglycine tert-butyl ester N-[N-(3,5-di-(trifluoromethyl)phenyl)alanyl]-phenylglycine tert-butyl ester N-[N-(3,5-dimethoxyphenyl)alanyl]-2-aminohexanoic acid methyl ester and pharmaceutically acceptable salts thereof.

Still further, this invention provides for novel compounds of the formula III:

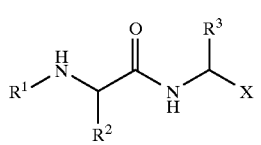

III wherein:

R¹ is selected from the group consisting of (a) phenyl, (b) a substituted phenyl group of formula II:

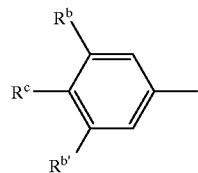

II wherein R$^c$ is selected from the group consisting of acyl, alkyl, alkoxy, alkylalkoxy, azido, cyano, halo, hydrogen, nitro, trihalomethyl, thioalkoxy, and wherein R$^b$ and R$^c$ are fused to form a heteroaryl or heterocyclic ring with the phenyl ring, R$^b$ and R$^{b'}$ are independently selected from the group consisting of hydrogen, halo, nitro, cyano, trihalomethyl, alkoxy, and thioalkoxy with the proviso that when R$^c$ is hydrogen, then R$^b$ and R$^{b'}$ are either both hydrogen or both substituents other than hydrogen, (c) 2-naphthyl, (d) 2-naphthyl substituted at the 4, 5, 6, 7 and/or 8 positions with 1 to 5 substituents selected from the group consisting of alkyl, alkoxy, halo, cyano, nitro, trihalomethyl, thioalkoxy, aryl, and heteroaryl, (e) heteroaryl, and (f) substituted heteroaryl containing 1 to 3 substituents selected from the group consisting of alkyl, alkoxy, aryl, aryloxy, cyano, halo, nitro, heteroaryl, thioalkoxy and thioaryloxy provided that said substituents are not ortho to the heteroaryl attachment to the —NH group;

R² is selected from the group consisting of hydrogen, alkyl of from 1 to 4 carbon atoms, alkylalkoxy of from 1 to 4 carbon atoms, alkylthioalkoxy of from 1 to 4 carbon atoms, aryl, heteroaryl, substituted aryl and substituted heteroaryl provided that the substituents are not ortho to the attachment of the aryl or heteroaryl atom to the carbon atom;

R³ is selected from the group consisting of alkyl, alkenyl, alkynyl, aryl, cycloalkyl, cycloalkenyl, heteroaryl, substituted alkyl, substituted alkenyl, substituted alkynyl, and heterocyclic;

X is —C(O)Y where Y is selected from the group consisting of (a) alkyl, (b) substituted alkyl with the proviso that the substitution on said substituted alkyl does not include α-haloalkyl, α-diazoalkyl or α-OC(O)alkyl groups, (c) alkoxy or thioalkoxy, (d) substituted alkoxy or substituted thioalkoxy, (e) hydroxy, (f) aryl, (g) heteroaryl, (h) heterocyclic, (i) —NR'R" where R' and R" are independently selected from the group consisting of hydrogen, alkyl, substituted alkyl, cycloalkyl, aryl, heteroaryl, heterocyclic, and where R' and R" are joined to form a cyclic group having from 2 to 8 carbon atoms optionally containing 1 to 2 additional heteroatoms selected from the group consisting of oxygen, sulfur and nitrogen and optionally substituted with one or more alkyl or alkoxy groups, and when R³ contains at least 3 carbon atoms, X can also be —CR⁴R⁴Y' where each R⁴ is independently selected from the group consisting of hydrogen, alkyl, cycloalkyl, aryl, heteroaryl and heterocyclic and Y' is selected from the group consisting of hydroxyl, amino, thiol, —OC(O)R$^5$, —SSR$^5$, —SSC(O)R$^5$ where R$^5$ is selected from the group consisting of alkyl, substituted alkyl, cycloalkyl, aryl, heteroaryl and heterocyclic, and with the proviso that when R$^1$ is 3,4-dichlorophenyl, R$^2$ is methyl, and R$^3$ is benzyl derived from D-phenylglycine, then X is not —C(O)OCH$_3$, and still with the further proviso excluding the following known compounds:

when R$^1$ is phenyl, R$^2$ is methyl, X is —C(O)NHφ, then R$^3$ is not methyl, iso-propyl, iso-butyl; and when R$^1$ is phenyl, R$^2$ is methyl, X is —C(O)NH$_2$, then R$^3$ is not benzyl.

Preferred compounds of formula III above include those set forth below in Table I below:

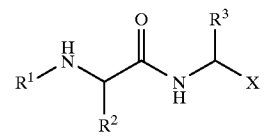

III

TABLE I

| R$^1$ | R$^2$ | R$^3$ | X |
|---|---|---|---|
| 3,4-dichlorophenyl | —CH$_3$ | —CH(CH$_3$)$_2$ | —C(O)OCH$_3$ |
| 3,4-dichlorophenyl | —CH$_3$ | —CH(CH$_3$)$_2$ | —C(O)NHCH$_2$CH(CH$_3$)$_2$ |
| 3,4-dichlorophenyl | —CH$_3$ | —CH(OH)CH$_3$ | —C(O)OCH$_3$ |
| 3,4-dichlorophenyl | —CH$_3$ | —CH(CH$_3$)$_2$ | —C(O)OCH$_2$CH$_3$ |
| 3,4-dichlorophenyl | —CH$_3$ | —CH(CH$_3$)$_2$ | —C(O)OC(CH$_3$)$_3$ |
| 3,4-dichlorophenyl | —CH$_3$ | —CH(CH$_3$)$_2$ | —C(O)NH$_2$ |
| 3,4-dichlorophenyl | —CH$_3$ | —CH(CH$_3$)$_2$ | —CH$_2$OH |
| 3,4-dichlorophenyl | —CH$_3$ | —CH(CH$_3$)$_2$ | —C(O)N(CH$_3$)$_2$ |
| 3,4-dichlorophenyl | —CH$_3$ | —CH(CH$_3$)$_2$ | —C(O)NHCH$_3$ |
| 3,4-dichlorophenyl | —CH$_3$ | —CH$_3$ | —C(O)OCH$_3$ |
| 3,4-dichlorophenyl | —CH$_3$ | —CH$_2$CH(CH$_3$)$_2$ | —C(O)OCH$_3$ |
| 3,4-dichlorophenyl | —CH$_3$ | —CH$_2$-φ | —C(O)OCH$_3$ |
| 3,4-dichlorophenyl | —CH$_3$ | —CH(CH$_3$)CH$_2$CH$_3$ | —C(O)OCH$_3$ |
| 3,4-dichlorophenyl | —CH$_3$ | —CH$_2$CH$_2$CH$_3$ | —C(O)OCH$_3$ |
| 3,4-dichlorophenyl | —CH$_3$ | —(CH$_2$)$_3$CH$_3$ | —C(O)OCH$_3$ |
| 3,4-dichlorophenyl | —CH$_3$ | —CH$_2$-indol-3-yl | —C(O)OCH$_3$ |
| 3,4-dichlorophenyl | —CH$_3$ | —CH$_2$COOH | —C(O)OCH$_3$ |
| 3,4-dichlorophenyl | —CH$_3$ | —CH$_2$C(O)O-tert-butyl | —C(O)OCH$_3$ |
| 3,4-dichlorophenyl | —CH$_3$ | —(CH$_2$)$_4$-NH—BOC | —C(O)OCH$_3$ |
| benzothiazol-6-yl | —CH$_3$ | —(CH$_2$)$_3$CH$_3$ | —C(O)OCH$_3$ |
| 3,4-dichlorophenyl | —CH$_3$ | —(CH$_2$)$_4$NH$_2$ | —C(O)OCH$_3$ |
| 3,4-dichlorophenyl | —CH$_3$ | p-hydroxybenzyl | —C(O)OCH$_3$ |
| 3,5-dichlorophenyl | —CH$_3$ | —CH$_3$ | —C(O)OCH$_3$ |
| 3,5-dichlorophenyl | —CH$_3$ | —CH$_2$CH$_2$CH$_3$ | —C(O)OCH$_3$ |
| 3,5-dichlorophenyl | —CH$_3$ | —CH$_2$-φ | —C(O)OCH$_3$ |
| 3,4-dichlorophenyl | —CH$_3$ | —CH$_2$C(O)OCH$_3$ | —C(O)OCH$_3$ |
| 3,4-dichlorophenyl | —CH$_3$ | —CH$_2$-(1-N-benzyl-imidazol-4-yl) | —C(O)OCH$_3$ |
| 3,4-dichlorophenyl | —CH$_3$ | —(CH$_2$)$_2$C(O)O-tert-Bu | —C(O)OCH$_3$ |
| 3,4-dichlorophenyl | —CH$_3$ | —CH$_2$CH(CH$_3$)$_2$ | —C(O)NH$_2$ |
| 3,4-dichlorophenyl | —CH$_3$ | —CH$_2$CH$_2$COOH | —C(O)OCH$_3$ |
| 3,4-dichlorophenyl | —CH$_3$ | —CH$_2$-(3,5-diiodo-4-hydroxyphenyl) | —C(O)OCH$_3$ |
| 3,4-dichlorophenyl | —CH$_3$ | —CH$_2$-(3-iodo-4-hydroxyphenyl) | —C(O)OCH$_3$ |
| 3,4-dichlorophenyl | H | —CH$_2$CH$_2$CH$_3$ | —C(O)OCH$_3$ |
| 3,4-dichlorophenyl | —CH$_3$ | —(CH$_2$)$_4$NC(O)—(CH$_2$)$_4$CH$_3$ | —C(O)OCH$_3$ |
| 3,4-dichlorophenyl | —CH$_3$ | —CH$_2$-φ | —C(O)NH$_2$ |
| 3,4-dichlorophenyl | —CH$_3$ | —CH$_2$CH$_2$CH$_2$CH$_3$ | —C(O)NHCH$_3$ |
| 3,4-dichlorophenyl | —CH$_3$ | —CH$_2$-cyclohexyl | —C(O)OCH$_3$ |
| 3,4-dichlorophenyl | —CH$_3$ | —(CH$_2$)$_3$CH$_3$ | —C(O)NH$_2$ |
| 3,4-dichlorophenyl | —CH$_3$ | —(CH$_2$)$_3$CH$_3$ | —C(O)N(CH$_3$)$_2$ |
| 3,4-dichlorophenyl | —CH$_3$ | —CH$_2$CH$_2$SCH$_3$ | —C(O)OCH$_3$ |
| 3,5-dichlorophenyl | —CH$_3$ | —CH$_2$CH$_2$CH$_2$CH$_3$ | —C(O)N(CH$_3$)$_2$ |
| 3,5-dichlorophenyl | —CH$_3$ | —CH$_2$CH$_2$CH$_2$CH$_3$ | —C(O)NH$_2$ |
| 3,5-dichlorophenyl | —CH$_3$ | —CH$_2$CH$_2$CH$_2$CH$_3$ | —C(O)NHCH$_3$ |
| 3,4-dichlorophenyl | —CH$_3$ | —CH$_2$-imidazol-4-yl | —C(O)OCH$_3$ |
| quinolin-3-yl | —CH$_3$ | —CH$_2$CH$_2$CH$_2$CH$_3$ | —C(O)OCH$_3$ |
| benzothiazol-2-yl | —CH$_3$ | —CH$_2$CH$_2$CH$_2$CH$_3$ | —C(O)OCH$_3$ |
| 3,5-difluorophenyl | —CH$_3$ | —CH$_3$ | —C(O)OCH$_3$ |
| 3,5-difluorophenyl | —CH$_3$ | —CH$_2$CH$_2$CH$_2$CH$_3$ | —C(O)OCH$_3$ |
| 3,4-dichlorophenyl | —CH$_3$ | —CH$_2$CH$_2$CH$_2$CH$_3$ | —C(O)NH$_2$ |
| 3,4-dichlorophenyl | —CH$_3$ | —CH$_2$CH$_2$CH$_2$CH$_3$ | —C(O)NHCH$_2$-φ |
| 3,4-dichlorophenyl | —CH$_3$ | -φ | —CH$_2$OH |
| 3,5-dichlorophenyl | -φ | —CH$_3$ | —C(O)OCH$_3$ |
| 3,4-dichlorophenyl | —CH$_3$ | —CH$_2$CH$_2$CH$_2$CH$_3$ | —CH$_2$OH |
| 3,5-dichlorophenyl | —CH$_3$ | -φ | —CH$_2$OH |
| 3,5-dichlorophenyl | —CH$_3$ | -φ | —C(O)OC(CH$_3$)$_3$ |

TABLE I-continued

| R¹ | R² | R³ | X |
|---|---|---|---|
| 3,5-di-(trifluoro-methyl)phenyl | —CH₃ | -φ | —C(O)OC(CH₃)₃ |
| 3,5-dimethoxy-phenyl | —CH₃ | —CH₂CH₂CH₂CH₃ | —C(O)OCH₃ |

DETAILED DESCRIPTION OF THE INVENTION

As above, this invention relates to compounds which inhibit β-amyloid peptide release and/or its synthesis, and, accordingly, have utility in treating Alzheimer's disease. However, prior to describing this invention in further detail, the following terms will first be defined.

Definitions

The term "β-amyloid peptide" refers to a 39–43 amino acid peptide having a molecular weight of about 4.2 kD which peptide is substantially homologous to the form of the protein described by Glenner, et al.[1] including mutations and post-translational modifications of the normal β-amyloid peptide. In whatever form, the β-amyloid peptide is approximately a 39–43 amino acid fragment of a large membrane-spanning glycoprotein, referred to as the β-amyloid precursor protein (APP). Its 43-amino acid sequence is:

1
Asp Ala Glu Phe Arg His Asp Ser Gly Tyr
11
Glu Val His His Gln Lys Leu Val Phe Phe
21
Ala Glu Asp Val Gly Ser Asn Lys Gly Ala
31
Ile Ile Gly Leu Met Val Gly Gly Val Val
41
Ile Ala Thr (SEQ ID NO: 1)

or a sequence which is substantially homologous thereto.

"Alkyl" refers to monovalent alkyl groups preferably having from 1 to 10 carbon atoms and more preferably 1 to 6 carbon atoms. This term is exemplified by groups such as methyl, ethyl, n-propyl, iso-propyl, n-butyl, iso-butyl, n-hexyl, and the like.

"Substituted alkyl" refers to an alkyl group, preferably of from 1 to 10 carbon atoms, having from 1 to 3 substituents selected from the group consisting of alkoxy, substituted alkoxy, acyl, acylamino, acyloxy, amino, aminoacyl, aminoacyloxy, cyano, halogen, hydroxyl, carboxyl, carboxylalkyl, cycloalkyl, oxyacylamino, thiol, thioalkoxy, substituted thioalkoxy, aryl, heteroaryl, heterocyclic, nitro, and mono- and di-alkylamino, mono- and di-(substituted alkyl)amino, mono- and di-cycloalkylamino, mono- and di-arylamino, mono- and di-heteroaryl-amino, mono- and di-heterocyclic amino, and unsymmetric di-substituted amines having different substituents selected from alkyl, substituted alkyl, cycloalkyl, aryl, heteroaryl and heterocyclic.

"Alkylene" refers to divalent alkylene groups preferably having from 1 to 10 carbon atoms and more preferably 1 to 6 carbon atoms. This term is exemplified by groups such as methylene (—CH₂—), ethylene (—CH₂CH₂—), the propylene isomers (e.g., —CH₂CH₂CH₂— and —CH(CH₃)CH₂—) and the like.

"Alkaryl" refers to -alkylene-aryl groups preferably having from 1 to 10 carbon atoms in the alkylene moiety and from 6 to 10 carbon atoms in the aryl moiety. Such alkaryl groups are exemplified by benzyl, phenethyl and the like.

"Alkoxy" refers to the group "alkyl-O-". Preferred alkoxy groups include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

"Substituted alkoxy" refers to the group "substituted alkyl-O-" where substituted alkyl is as defined above.

"Alkylalkoxy" refers to the group "-alkylene-O-alkyl" where alkylene and alkyl are as defined above. Such groups include, by way of example, methylenemethoxy (—CH₂OCH₃), ethylenemethoxy (—CH₂CH₂OCH₃), n-propylene-iso-propoxy (—CH₂CH₂C₂OCH(CH₃)₂), methylene-tert-butoxy (—CH₂—O—C(CH₃)₃) and the like.

"Alkylthioalkoxy" refers to the group "-alkylene-S-alkyl" where alkylene and alkyl are as defined above. Such groups include, by way of example, methylenethiomethoxy (—CH₂SCH₃), ethylenethiomethoxy (—CH₂CH₂SCH₃), n-propylene-iso-thiopropoxy (—CH₂CH₂CH₂SCH(CH₃)₂), methylenethio-tert-butoxy (—CH₂SC(CH₃)₃) and the like.

"Alkenyl" refers to alkenyl groups preferably having from 2 to 10 carbon atoms and more preferably 2 to 6 carbon atoms and having at least 1 and preferably from 1–2 sites of alkenyl unsaturation. Preferred alkenyl groups include ethenyl (—CH=CH₂), n-propenyl (—CH₂CH=CH₂), iso-propenyl (—C(CH₃)=CH₂), and the like.

"Substituted alkenyl" refers to an alkenyl group as defined above having from 1 to 3 substituents selected from the group consisting of alkoxy, substituted alkoxy, acyl, acylamino, acyloxy, amino, aminoacyl, aminoacyloxy, cyano, cycloalkyl, oxyacylamino, halogen, hydroxyl, carboxyl, carboxylalkyl, thiol, thioalkoxy, substituted thioalkoxy, aryl, heteroaryl, heterocyclic, nitro, and mono- and di-alkylamino, mono- and di-(substituted alkyl)amino, mono- and di-cycloalkyl, mono- and di-arylamino, mono- and di-heteroarylamino, mono- and di-heterocyclic amino, and unsymmetric di-substituted amines having different substituents selected from alkyl, substituted alkyl, cycloalkyl, aryl, heteroaryl and heterocyclic.

"Alkynyl" refers to alkynyl groups preferably having from 2 to 10 carbon atoms and more preferably 2 to 6 carbon atoms and having at least 1 and preferably from 1–2 sites of alkynyl unsaturation. Preferred alkynyl groups include ethynyl (—C≡CH), propargyl (—CH₂C≡CH) and the like.

"Substituted alkynyl" refers to an alkynyl group as defined above having from 1 to 3 substituents selected from the group consisting of alkoxy, substituted alkoxy, acyl, acylamino, acyloxy, amino, aminoacyl, aminoacyloxy, cyano, cycloalkyl, oxyacylamino, halogen, hydroxyl, carboxyl, carboxylalkyl, thiol, thioalkoxy, substituted thioalkoxy, aryl, heteroaryl, heterocyclic, nitro, and mono- and di-alkylamino, mono- and di-(substituted alkyl)amino, mono- and di-cycloalkylamino, mono- and di-arylamino, mono- and di-heteroarylamino, mono- and di-heterocyclic amino, and unsymmetric di-substituted amines having different substituents selected from alkyl, substituted alkyl, cycloalkyl, aryl, heteroaryl and heterocyclic.

"Acyl" refers to the groups alkyl-C(O)—, substituted alkyl-C(O)—, cycloalkyl-C(O)—, aryl-C(O)—, heteroaryl-C(O)— and heterocyclic-C(O)— where alkyl, substituted alkyl, cycloalkyl, aryl, heteroaryl and heterocyclic are as defined herein.

"Acylamino" refers to the group —C(O)NRR where each R is independently hydrogen, alkyl, substituted alkyl, cycloalkyl, aryl, heteroaryl, and heterocyclic and where each of alkyl, substituted alkyl, cycloalkyl, aryl, heteroaryl and heterocyclic are as defined herein.

"Aminoacyl" refers to the group —NRC(O)R where each R is independently hydrogen, alkyl, substituted alkyl, cycloalkyl, aryl, heteroaryl, and heterocyclic and where each of alkyl, substituted alkyl, cycloalkyl, aryl, heteroaryl and heterocyclic are as defined herein.

"Acyloxy" refers to the groups —OC(O)-alkyl, —OC(O)-substituted alkyl, —OC(O)-cycloalkyl, —OC(O)-aryl, —C(O)O-heteroaryl-, and —C(O)O-heterocyclic where alkyl, substituted alkyl, cycloalkyl, aryl, heteroaryl and heterocyclic are as defined herein.

"Aminoacyloxy" refers to the groups —NRC(O)O-alkyl, —NRC(O)O-substituted alkyl, —NRC(O)O-cycloalkyl, —NRC(O)O-aryl, —NRC(O)O-heteroaryl-, and —NRC(O)O-heterocyclic where R is hydrogen, alkyl, substituted alkyl, cycloalkyl, aryl, heteroaryl, and heterocyclic and where each of alkyl, substituted alkyl, cycloalkyl, aryl, heteroaryl and heterocyclic are as defined herein.

"Oxyacylamino" refers to the groups —OC(O)NR-alkyl, —OC(O)NR-substituted alkyl, —OC(O)NR-aryl, —OC(O)NR-heteroaryl-, and —OC(O)NR-heterocyclic where R is hydrogen, alkyl, substituted alkyl, cycloalkyl, aryl, heteroaryl, and heterocyclic and where each of alkyl, substituted alkyl, cycloalkyl, aryl, heteroaryl and heterocyclic are as defined herein.

"Aryl" refers to an unsaturated aromatic carbocyclic group of from 6 to 14 carbon atoms having a single ring (e.g., phenyl) or multiple condensed rings (e.g., naphthyl or anthryl). Preferred aryls include phenyl, naphthyl and the like.

Unless otherwise constrained by the definition for the aryl substituent, such aryl groups can optionally be substituted with from 1 to 3 substituents selected from the group consisting of hydroxy, acyl, acyloxy, alkyl, substituted alkyl, alkoxy, substituted alkoxy, alkenyl, substituted alkenyl, alkynyl, substituted alkynyl, amino, aminoacyl, acylamino, aminoacyloxy, oxyacylamino, aryl, aryloxy, carboxyl, carboxylalkyl, cyano, halo, nitro, heteroaryl, trihalomethyl, thioalkoxy, substituted thioalkoxy, mono- and di-alkylamino, mono- and di-(substituted alkyl)amino, mono- and di-cycloalkylamino, mono- and di-arylamino, mono-and di-heteroarylamino, mono- and di-heterocyclic amino, and unsymmetric di-substituted amines having different substituents selected from alkyl, substituted alkyl, cycloalkyl, aryl, heteroaryl and heterocyclic, and the like. Preferred substituents include alkyl, alkoxy, halo, cyano, nitro, trihalomethyl, and thioalkoxy. When so substituted, such aryl groups are sometimes referred to herein as "substituted aryl".

"Aryloxy" refers to the group aryl-O- wherein the aryl group is as defined above including optionally substituted aryl groups as also defined above.

"Carboxyalkyl" refers to the groups —C(O)O-alkyl and —C(O)O-substituted alkyl where alkyl and substituted alkyl are as defined herein.

"Cycloalkyl" refers to cyclic alkyl groups of from 3 to 20 carbon atoms having a single cyclic ring or multiple condensed rings (including aromatic rings fused to the cycloalkyl ring) which can be optionally substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, or multiple ring structures such as dibenzosuberane, adamantanyl, and the like.

"Cycloalkenyl" refers to cyclic alkenyl groups of from 4 to 8 carbon atoms having a single cyclic ring or multiple condensed rings and at least one point of internal unsaturation which can be optionally substituted with from 1 to 3 alkyl groups. Examples of suitable cycloalkenyl groups include, for instance, cyclobut-2-enyl, cyclopent-3-enyl, cyclooct-3-enyl and the like.

"Halo" or "halogen" refers to fluoro, chloro, bromo and iodo and preferably is either chloro or bromo.

"Heteroaryl" refers to a monovalent aromatic group of from 2 to 10 carbon atoms and 1 to 4 heteroatoms selected from oxygen, nitrogen and sulfur within the ring.

Unless otherwise constrained by the definition for the heteroaryl substituent, such heteroaryl groups can be optionally substituted with 1 to 3 substituents selected from the group consisting of hydroxy, acyl, acyloxy, alkyl, substituted alkyl, alkoxy, substituted alkoxy, alkenyl, substituted alkenyl, alkynyl, substituted alkynyl, amino, aminoacyl, acylamino, aminoacyloxy, oxyacylamino, aryl, aryloxy, carboxyl, carboxylalkyl, cyano, halo, nitro, heteroaryl, trihalomethyl, thioalkoxy, substituted thioalkoxy, mono- and di-alkylamino, mono- and di-(substituted alkyl)amino, mono- and di-cycloalkylamino, mono- and di-arylamino, mono-and di-heteroarylamino, mono- and di-heterocyclic amino, and unsymmetric di-substituted amines having different substituents selected from alkyl, substituted alkyl, cycloalkyl, aryl, heteroaryl and heterocyclic, and the like. Such heteroaryl groups can have a single ring (e.g., pyridyl, furyl, etc.) or multiple condensed rings (e.g., indolizinyl or benzothienyl). Preferred heteroaryls include pyridyl, pyrrolyl, and furyl. When so substituted, such heteroaryl groups are sometimes referred to herein as "substituted heteroaryl".

"Heterocycle" or "heterocyclic" refers to a monovalent saturated or unsaturated group having a single ring or multiple condensed rings, from 1 to 12 carbon atoms and from 1 to 4 hetero atoms selected from nitrogen, sulfur or oxygen within the ring.

Unless otherwise constrained by the definition for the heterocyclic substituent, such heterocyclic groups can be optionally substituted with 1 to 3 substituents selected from the group consisting of hydroxy, acyl, acyloxy, alkyl, substituted alkyl, alkoxy, substituted alkoxy, alkenyl, substituted alkenyl, alkynyl, substituted alkynyl, amino, aminoacyl, acylamino, aminoacyloxy, oxyacylamino, aryl, aryloxy, carboxyl, carboxylalkyl, cyano, halo, nitro, heteroaryl, trihalomethyl, thioalkoxy, substituted thioalkoxy, mono- and di-alkylamino, mono- and di-(substituted alkyl) amino, mono- and di-arylamino, mono- and di-heteroarylamino, mono- and di-heterocyclic amino, and unsymmetric di-substituted amines having different substituents selected from alkyl, substituted alkyl, cycloalkyl, aryl, heteroaryl and heterocyclic, and the like. Such heterocyclic groups can have a single ring or multiple condensed rings. Preferred heterocyclics include morpholino, piperidinyl, and the like.

Examples of heterocycles and heteroaryls include, but are not limited to, furan, thiophene, thiazole, oxazole, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholino, piperidinyl, pyrrolidine, tetrahydrofuranyl, and the like.

"Thiol" refers to the group —SH.

"Thioalkoxy" refers to the group —S-alkyl.

"Substituted thioalkoxy" refers to the group —S-substituted alkyl.

"Thioaryloxy" refers to the group aryl-S— wherein the aryl group is as defined above including optionally substituted aryl groups as also defined above.

"Thioheteroaryloxy" refers to the group heteroaryl-S— wherein the heteroaryl group is as defined above including optionally substituted aryl groups as also defined above.

In the compounds of formula I, $R^b$ and $R_c$ can be fused to form a heteroaryl or heterocyclic ring with the phenyl ring. Fusion in this manner results in a fused bicyclic ring structure of the formula:

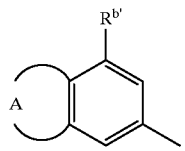

where $R^b$ is as defined above and A is the fused heteroaryl or heterocyclic group as these terms are as defined above wherein the two atoms of the phenyl ring are included in the total atoms present in the heteroaryl or heterocyclic group. Examples of such fused ring systems include, for instance, indol-5-yl, indol-6-yl, thionaphthen-5-yl, thionaphthen-6-yl, isothionaphthen-5-yl, isothionaphthen-6-yl, indoxazin-5-yl, indoxazin-6-yl, benzoxazol-5-yl, benzoxazol-6-yl, anthranil-5-yl, anthranil-6-yl, quinolin-6-yl, quinolin-7-yl, isoquinolin-6-yl, isoquinolin-7-yl, cinnolin-6-yl, cinnolin-7-yl, quinazolin-6-yl quinazolin-7-yl, benzofuran-5-yl, benzofuran-6-yl, isobenzofuran-5-yl, isobenzofuran-6-yl, and the like.

"Pharmaceutically acceptable salt" refers to pharmaceutically acceptable salts of a compound of Formula I which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

Compound Preparation

The compounds of formula I above are readily prepared via several divergent synthetic routes with the particular route selected relative to the ease of compound preparation, the commercial availability of starting materials, and the like.

In one synthetic method, the $R^1$ group of the amino acid $NH_2CH(R^2)COOH$ or an ester thereof is first introduced onto the molecule. Afterwards, conventional coupling of the first $R^1NHCH(R^2)COOH$ or ester thereof with the amine of $NH_2CH(R^3)C(O)Y$ provides for compounds of formula I wherein X is —C(O)Y.

Similarly, conventional reduction of the —C(O)Y group leads to —$CH_2OH$ groups and the like.

The introduction of the $R^1$ group onto the amino acid $NH_2CH(R^2)COOH$ or ester thereof can be accomplished using several methods. For example, conventional coupling of a halo acetic acid with a primary amine forms an amino acid as shown in reaction (1) below:

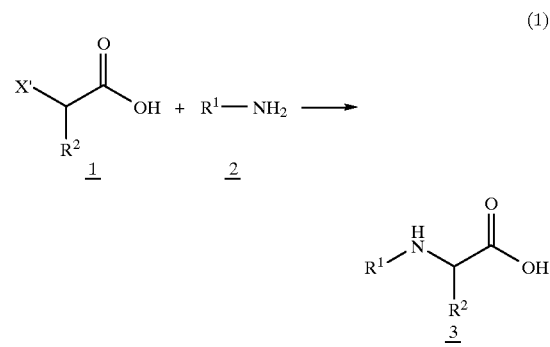

wherein $R^1$ and $R^2$ are as defined above and X' is preferably a halo group such as chloro or bromo. Alternatively, leaving groups other than halo may be employed such as triflate, mesylate, tosylate and the like. Additionally, suitable esters of 1 may be employed in this reaction.

Reaction (1) involves coupling of a suitable haloacetic acid derivative 1 with a primary aryl/heteroarylamine 2 under conditions which provide for amino acid 3. This reaction is described by, for example, Yates, et al.[10] and proceeds by combining approximately stoichiometric equivalents of haloacetic acid 1 with primary aryl/heteroarylamine 2 in a suitable inert diluent such as water, dimethylsulfoxide (DMSO) and the like. The reaction employs an excess of a suitable base such as sodium bicarbonate, sodium hydroxide, etc. to scavenge the acid generated by the reaction. The reaction is preferably conducted at from about 25° C. to about 100° C. until reaction completion which typically occurs within 1 to about 24 hours. This reaction is further described in U.S. Pat. No. 3,598,859, which is incorporated herein by reference in its entirety. Upon reaction completion, N-aryl/N-heteroaryl amino acid 3 is recovered by conventional methods including precipitation, chromatography, filtration and the like.

In reaction (1), each of the reagents (haloacetic acid 1, primary aryl/heteroarylamine 2 and alcohol 3) are well known in the art with a plurality of each being commercially available.

In an alternative embodiment, the $R^1$ group can be coupled to an alanine ester (or other suitable amino acid ester) by conventional N-arylation. For example, a stoichiometric equivalent or slight excess of the amino acid ester can be dissolved in a suitable diluent such as DMSO and coupled with a haloaryl compound, X—$R^1$ where X is a halo group such as fluoro, chloro or bromo and $R^1$ is as defined above. The reaction is conducted in the presence of an excess of base such as sodium hydroxide to scavenge the acid generated by the reaction. The reaction typically proceeds at from 15° C. to about 250° C. and is complete in about 1 to 24 hours. Upon reaction completion, N-aryl amino acid ester is recovered by conventional methods including chromatography, filtration and the like.

In still another alternative embodiment, the esterified amino acids of formula I above can be prepared by reductive amination of a suitable 2-oxocarboxylic acid ester (such as a pyruvate ester) in the manner illustrated in Reaction (2) below:

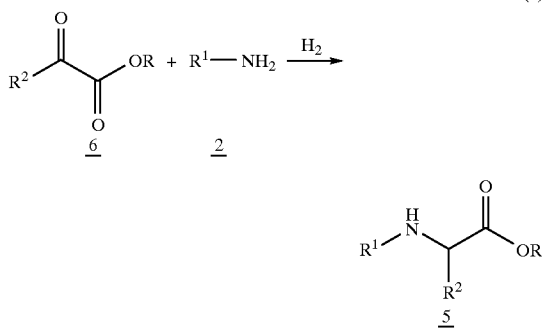

(2)

wherein $R^1$ and $R^2$ are as defined above.

In reaction (2), approximately stoichiometric equivalents of a 2-oxocarboxylic acid ester 6 and arylamine 2 are combined in an inert diluent such as methanol, ethanol and the like and the reaction solution treated under conditions which provide for imine formation (not shown). The imine formed is then reduced under conventional conditions by a suitable reducing agent such as sodium cyanoborohydride, $H_2$/palladium on carbon and the like to form the N-aryl amino acid ester 5. In a particularly preferred embodiment, the reducing agent is $H_2$/palladium on carbon which is incorporated into the initial reaction medium which permits imine reduction in situ in a one pot procedure to provide for the N-aryl amino acid ester 5.

The reaction is preferably conducted at from about 20° C. to about 80° C. at a pressure of from 1 to 10 atmospheres until reaction completion which typically occurs within 1 to about 24 hours. Upon reaction completion, N-aryl amino acid ester 5 is recovered by conventional methods including chromatography, filtration and the like.

Subsequent hydrolysis of the ester 5 leads to the corresponding carboxylic acid derivative.

A further embodiment for preparing N-aryl amino acids includes aromatic nucleophilic substitution of fluorobenzenes by the amine group of an amino acid.

The carboxylic acid derivative 5 is then coupled under conventional conditions well known in the art with a compound of the formula $NH_2CH(R^3)C(O)Y$ where $R^3$ and Y are as defined above. Such coupling leads to compounds of formula I. Subsequent modifications (e.g., reduction) lead to further compounds of formula I.

When Y is an ester group, conventional transesterification techniques can be used to prepare a variety of different ester groups on the compounds of formula I. Numerous techniques are known in the art to effect transesterification and each technique merely replaces the ester group with a different ester group derived from the corresponding alcohol or thioalcohol and, in some cases, a catalyst such as titanium (IV) iso-propoxide is used to facilitate reaction completion. In one technique, the alcohol or thioalcohol is first treated with sodium hydride in a suitable diluent such as toluene to form the corresponding sodium alkoxide or thioalkoxide which is then employed to effect transesterification. The efficiency of this technique makes it particularly useful with high boiling and/or expensive alcohols.

In another transesterification technique, the ester to be transesterified is placed in a large excess of the alcohol or thioalcohol which effects transesterification. A catalytic amount of sodium hydride is then added and the reaction proceeds quickly under conventional conditions to provide the desired transesterified product. Because this protocol requires the use of a large excess of alcohol or thioalcohol, this procedure is particularly useful when the alcohol is inexpensive.

Transesterification provides a facile means to provide for a multiplicity of different ester substituents on the compounds of formula I above. In all cases, the alcohols and thioalcohols employed to effect transesterification are well known in the art with a significant number being commercially available.

Other methods for preparing the esters of this invention include, by way of example, first hydrolyzing the ester to the free acid followed by O-alkylation with, e.g., a haloalkyl group in the presence of a base such as potassium carbonate.

Still other methods for the preparation of compounds of formula I are provided in the examples below.

Compounds where X is $-CR^4R^4Y'$ are readily prepared by coupling, e.g. an amino alcohol $H_2NCHR^3CR^4R^4OH$, to the carboxyl group of $R^1NHCHR^2C(O)OH$ under standard coupling conditions well known in peptide coupling chemistry which can use well known coupling reagents such as carbodiimides with or without the use of well known additives such as N-hydroxysuccinimide, 1-hydroxybenzotriazole, etc. If necessary, well known blocking groups on Y' can be employed to protect the group during coupling. Such blocking groups are particularly desirable when Y' is an amino group.

The reaction is conventionally conducted in an inert aprotic diluent such as dimethylformamide, dichloromethane, chloroform, acetonitrile, tetrahydrofuran and the like. Upon reaction completion, any blocking groups on Y' are selectively removed to provide for the desired compound.

When Y' is —OH or —SH, post-synthetic conversion of these groups to the corresponding esters (i.e., $-OC(O)R^5$), disulfides (i.e., $-SSR^5$) and $-SSC(O)R^5$ groups is accomplished using well known chemistry. For example, ester synthesis requires only reaction with a suitable acid such as acetic acid ($R^7$=methyl), acid halide (e.g., acid chloride) or acid anhydride under suitable esterification conditions.

When one of $R^4$ groups is hydrogen, post-synthetic oxidation of the $-CHR^4OH$ group leads to the ketone derivatives. Alternatively, such ketones can be prepared by coupling the suitable aminoketone.HCl salt with the terminal carboxyl group of the amino acid.

In these synthetic methods, the starting materials can contain a chiral center (e.g., alanine) and, when a racemic starting material is employed, the resulting product is a mixture of diastereomers or R,S enantiomers. Alternatively, a chiral isomer of the starting material can be employed and, if the reaction protocol employed does not racemize this starting material, a chiral product is obtained. Such reaction protocols can involve inversion of the chiral center during synthesis.

Accordingly, unless otherwise indicated, the products of this invention are a mixture of diastereomers (if two or more chiral centers are present) or R,S enantiomers (if only one chiral center is present). Preferably, however, when a chiral product is desired, the chiral product corresponds to the L-amino acid derivative. Alternatively, chiral products can be obtained via purification techniques which separates diastereomers or enantiomers from a R,S mixture to provide for one or the other stereoisomer. Such techniques are well known in the art.

Pharmaceutical Formulations

When employed as pharmaceuticals, the compounds of formula I are usually administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound.

This invention also includes pharmaceutical compositions which contain, as the active ingredient, one or more of the compounds of formula I above associated with pharmaceutically acceptable carriers. In making the compositions of this invention, the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Preferably, the compound of formula I above is employed at no more than about 20 weight percent of the pharmaceutical composition, more preferably no more than about 15 weight percent, with the balance being pharmaceutically inert carrier(s).

The active compound is effective over a wide dosage range and is generally administered in a pharmaceutically effective amount. It, will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices which deliver the formulation in an appropriate manner.

The following formulation examples illustrate representative pharmaceutical compositions of the present invention.

Formulation Example 1

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules in 340 mg quantities.

Formulation Example 2

A tablet formula is prepared using the ingredients below:

| Ingredient | Quantity (mg/tablet) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 3

A dry powder inhaler formulation is prepared containing the following components:

| Ingredient | Weight % |
|---|---|
| Active Ingredient | 5 |
| Lactose | 95 |

The active ingredient is mixed with the lactose and the mixture is added to a dry powder inhaling appliance.

Formulation Example 4

Tablets, each containing 30 mg of active ingredient, are prepared as follows:

| Ingredient | Quantity (mg/tablet) | |
|---|---|---|
| Active Ingredient | 30.0 | mg |
| Starch | 45.0 | mg |
| Microcrystalline cellulose | 35.0 | mg |
| Polyvinylpyrrolidone (as 10% solution in sterile water) | 4.0 | mg |
| Sodium carboxymethyl starch | 4.5 | mg |
| Magnesium stearate | 0.5 | mg |
| Talc | 1.0 | mg |
| Total | 120 | mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation Example 5

Capsules, each containing 40 mg of medicament are made as follows:

| Ingredient | (mg/capsule) | |
|---|---|---|
| Active Ingredient | 40.0 | mg |
| Starch | 109.0 | mg |
| Magnesium stearate | 1.0 | mg |
| Total | 150.0 | mg |

The active ingredient, starch, and magnesium stearate are blended, passed through a No. 20 mesh U.S. sieve, and filled into hard gelatin capsules in 150 mg quantities.

Formulation Example 6

Suppositories, each containing 25 mg of active ingredient are made as follows:

| Ingredient | Amount | |
|---|---|---|
| Active Ingredient | 25 | mg |
| Saturated fatty acid glycerides to | 2,000 | mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 7

Suspensions, each containing 50 mg of medicament per 5.0 mL dose are made as follows:

| Ingredient | Amount | |
|---|---|---|
| Active Ingredient | 50.0 | mg |
| Xanthan gum | 4.0 | mg |
| Sodium carboxymethyl cellulose (11%) | 50.0 | mg |
| Microcrystalline cellulose (89%) | | |
| Sucrose | 1.75 | g |
| Sodium benzoate | 10.0 | mg |
| Flavor and Color | q.v. | |
| Purified water to | 5.0 | mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Example 8

| Ingredient | Quantity (mg/capsule) | |
|---|---|---|
| Active Ingredient | 15.0 | mg |
| Starch | 407.0 | mg |
| Magnesium stearate | 3.0 | mg |
| Total | 425.0 | mg |

The active ingredient, starch, and magnesium stearate are blended, passed through a No. 20 mesh U.S. sieve, and filled into hard gelatin capsules in 425.0 mg quantities.

Formulation Example 9

A subcutaneous formulation may be prepared as follows:

| Ingredient | Quantity |
| --- | --- |
| Active Ingredient | 5.0 mg |
| Corn Oil | 1.0 mL |

Formulation Example 10

A topical formulation may be prepared as follows:

| Ingredient | Quantity |
| --- | --- |
| Active Ingredient | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472 which is herein incorporated by reference.

Indirect techniques, which are generally preferred, usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

Other suitable formulations for use in the present invention can be found in *Remington's Pharmaceutical Sciences*, Mace Publishing Company, Philadelphia, Pa., 17th ed. (1985).

Utility

The compounds and pharmaceutical compositions of the invention are useful in inhibiting β-amyloid peptide release and/or its synthesis, and, accordingly, have utility in treating Alzheimer's disease in mammals including humans.

As noted above, the compounds described herein are suitable for use in a variety of drug delivery systems described above. Additionally, in order to enhance the in vivo serum half-life of the administered compound, the compounds may be encapsulated, introduced into the lumen of liposomes, prepared as a colloid, or other conventional techniques may be employed which provide an extended serum half-life of the compounds. A variety of methods are available for preparing liposomes, as described in, e.g., Szoka, et al., U.S. Pat. Nos. 4,235,871, 4,501,728 and 4,837,028 each of which is incorporated herein by reference.

The amount of compound administered to the patient will vary depending upon what is being administered, the purpose of the administration, such as prophylaxis or therapy, the state of the patient, the manner of administration, and the like. In therapeutic applications, compositions are administered to a patient already suffering from AD in an amount sufficient to at least partially arrest further onset of the symptoms of the disease and its complications. An amount adequate to accomplish this is defined as "therapeutically effective dose." Amounts effective for this use will depend on the judgment of the attending clinician depending upon factors such as the degree or severity of AD in the patient, the age, weight and general condition of the patient, and the like. Preferably, for use as therapeutics, the compounds described herein are administered at dosages ranging from about 0.1 to about 500 mg/kg/day.

In prophylactic applications, compositions are administered to a patient at risk of developing AD (determined for example by genetic screening or familial trait) in an amount sufficient to inhibit the onset of symptoms of the disease. An amount adequate to accomplish this is defined as "prophylactically effective dose." Amounts effective for this use will depend on the judgment of the attending clinician depending upon factors such as the age, weight and general condition of the patient, and the like. Preferably, for use as prophylactics, the compounds described herein are administered at dosages ranging from about 0.1 to about 500 mg/kg/day.

As noted above, the compounds administered to a patient are in the form of pharmaceutical compositions described above. These compositions may be sterilized by conventional sterilization techniques, or may be sterile filtered. When aqueous solutions are employed, these may be packaged for use as is, or lyophilized, the lyophilized preparation being combined with a sterile aqueous carrier prior to administration. The pH of the compound preparations typically will be between 3 and 11, more preferably from 5 to 9 and most preferably from 7 and 8. It will be understood that use of certain of the foregoing excipients, carriers, or stabilizers will result in the formation of pharmaceutical salts.

The following synthetic and biological examples are offered to illustrate this invention and are not to be construed in any way as limiting the scope of this invention. Unless otherwise stated, all temperatures are in degrees Celsius.

EXAMPLES

In the examples below, the following abbreviations have the following meanings. If an abbreviation is not defined, it has its generally accepted meaning.

BOC=tert-butoxycarbonyl
bd=broad doublet
bs=broad singlet
Cbz=carbobenzyloxy
cc=cubic centimeter
CDI=1,1'-carbonyldiimidazole d=doublet
dd=doublet of doublets
DMF=dimethylformamide
DMSO=dimethyl sulfoxide
EDC=1-(3-dimethyaminopropyl)-ethylcarbodiimide hydrochloride
EDTA=ethylene diamine tetraacetic acid
eq.=equivalents
ether=diethyl ether
g=grams
L=liter
m=multiplet
M=molar
max=maximum
mg=milligram
min.=minutes
mL=milliliter
mM=millimolar
mmol=millimole
N=normal
ng=nanogram
nm=nanometers
OD=optical density
pg=picograms
pM=picomolar
psi=pounds per square inch
q=quartet
quint.=quintet
rpm=rotations per minute
rt=room temperature
s=singlet
sept=septet
t=triplet
THF=tetrahydrofuran
tlc=thin layer chromatography
μg=microgram
μL=microliter
UV=ultraviolet
w/v=weight to volume Additionally, the term "Aldrich" indicates that the compound or reagent used in the following procedures is commercially available from Aldrich Chemical Company, Inc., 1001 West Saint Paul Avenue, Milwaukee, Wis. 53233 U.S.A.; the term "Bachem" indicates the compound or reagent is commercially available from Bachem Biosciences Inc., 3700 Horizon Drive, Renaissance at Gulph Mills, King of Prussia, Pa. 19406 U.S.A.; the term "Fluka" indicates the compound or reagent is commercially available from Fluka Chemical Corp., 980 South 2nd Street, Ronkonkoma, N.Y. 11779 U.S.A.; the term "Lancaster" indicates the compound or reagent is commercially available from Lancaster Synthesis, Inc., P.O. Box 100, Windham, N.H. 03087 U.S.A.; the term "Sigma" indicates the compound or reagent is commercially available from Sigma, P.O. Box 14508, St. Louis, Mo. 63178 U.S.A. ; and the term "Sennchem" indicates the compound or reagent is commercially available from Senn Chemicals AG, P.O. Box 267, CH-9157 Dielsdorf, Switzerland.

In the examples below, all temperatures are in degrees Celsius (unless otherwise indicated) and the following general procedures were used prepare the compounds as indicated.

GENERAL PROCEDURE A

Reductive Amination

To a solution of arylamine in ethanol in a hydrogenation flask was added 1 equivalent of the 2-oxocarboxylic acid ester (e.g., pyruvate ester), followed by 10% palladium on carbon (25 weight percent based on the arylamine). The reaction was hydrogenated at 20 psi $H_2$ on a Parr shaker until complete reaction was indicated by tlc (30 minutes to 16 hours). The reaction mixture was then filtered through a pad of Celite 545 (available from Aldrich Chemical Company, Inc.) and stripped free of solvent on a rotary evaporator. The crude product residue was then further purified via chromatography.

GENERAL PROCEDURE B

N-Heteroarylation of Alanine

A solution of 1.1 equivalents of L-alanine and 2 equivalents NaOH in DMSO was stirred at room temperature for 1 hour, then 1 equivalent of 2-chlorobenzothiazole was added. The mixture was heated to 100° C. for 4 hours, then cooled to room temperature and poured onto ice. The pH of the resulting aqueous solution was adjusted to ~2, and the precipitated solid was removed by filtration. This solid was then dissolved in 1N NaOH and the resulting solution was filtered through a pad of Celite 545. The pH of the filtrate was adjusted to ~2, and the white precipitate was removed by filtration and washed with water to yield the product.

GENERAL PROCEDURE C

Ester Hydrolysis to Free Acid

Ester hydrolysis to the free acid was conducted by conventional methods. Below are two examples of such conventional de-esterification methods.

To a carboxylic ester compound (prepared, for example, by reductive amination via General Procedure A to provide for the N-aryl amino acid ester) in a 1:1 mixture of $CH_3OH/H_2O$ was added 2–5 equivalents of $K_2CO_3$. The mixture was heated to 50° C. for 0.5 to 1.5 hours until tlc showed complete reaction. The reaction was cooled to room temperature and the methanol was removed on a rotary evaporator. The remaining aqueous solution was adjusted to pH ~2, and ethyl acetate was added to extract the product. The organic phase was then washed with saturated aqueous NaCl and dried over $MgSO_4$. The solution was stripped free of solvent on a rotary evaporator to yield the product.

The amino acid ester was dissolved in dioxane/water (4:1) to which was added LiOH (~2 eq.) that was dissolved in water such that the total solvent after addition was about 2:1 dioxane:water. The reaction mixture was stirred until reaction completion and the dioxane was removed under reduced pressure. The residue was diluted with EtOAc, the layers were separated and the aqueous layer acidified to pH 2. The aqueous layer was back extracted with EtOAc, the combined organics were dried over $Na_2SO_4$ and the solvent was removed under reduced pressure after filtration. The residue was purified by conventional methods (e.g., recrystallization).

The following exemplifies this latter example. The methyl ester of 3-$NO_2$ phenylacetyl alanine 9.27 g (0.0348 mols) was dissolved in 60 mL dioxane and 15 mL of $H_2O$ and adding LiOH (3.06 g, 0.0731 mol) that has been dissolved in 15 mL of $H_2O$. After stirring for 4 hours, the dioxane was removed under reduced pressure and the residue diluted with EtOAc, the layers were separated and the aqueous layer acidified to pH 2. The aqueous layer was back extracted with EtOAc (4×100 mL), the combined organics were dried over $Na_2SO_4$ and the solvent was removed under reduced pressure after filtration. The residue was recrystallized from EtOAc/isooctane giving 7.5 g (85%). $C_{11}H_{12}N_2O_5$ requires C, 52.38 H, 4.80 N, 11.11. Anal found C, 52.54 H, 4.85 N, 11.08. $[\alpha]_{23}$=−29.9 @ 589 nm.

GENERAL PROCEDURE D

First EDC Coupling Procedure

To a 1:1 mixture of the desired acid and amino ester/amide in $CH_2Cl_2$ at 0° C. was added 1.5 equivalents triethylamine, followed by 2.0 equivalents hydroxybenzotriazole monohydrate, then 1.25 equivalents of ethyl-3-(3-dimethylamino)-propyl carbodiimide.HCl (EDC). The reaction was stirred overnight at room temperature, then transferred to a separatory funnel and washed with water, saturated aqueous $NaHCO_3$, 1N HCl, and saturated aqueous NaCl, and was then dried over $MgSO_4$. The solution was stripped free of solvent on a rotary evaporator to yield the crude product.

GENERAL PROCEDURE E

Second EDC Coupling Procedure

The carboxylic acid was dissolved in methylene chloride. The amino acid ester/amide (1 eq.), N-methylmorpholine (5 eq.) and hydroxybenzotriazole monohydrate (1.2 eq.) were added in sequence. A cooling bath was applied to the round bottomed flask until the solution reached 0° C. At that time, 1.2 eq. of 1-(3-dimethylaminopropyl)-3-ethylcarbodiimide hydrochloride (EDC) was added. The solution was allowed to stir overnight and come to room temperature under nitrogen pressure. The reaction mixture was worked up by washing the organic phase with saturated aqueous sodium carbonate, 0.1M citric acid, and brine before drying with sodium sulfate. The solvents were then removed to yield crude product. Pure products were obtained by flash chromatography in an appropriate solvent.

GENERAL PROCEDURE F

BOC and tert-Butyl Ester Removal Procedure

The BOC- or tert-butyl ester compound was added to a 1:1 mixture of $CH_2Cl_2$ and trifluoroacetic acid, and was stirred until tlc indicated complete conversion, typically 2 hours. The solution was then stripped to dryness and the residue was taken up in ethyl acetate. For the BOC protected compounds the solution was washed with dilute HCl. The aqueous phase was adjusted to a basic pH, then extracted with ethyl acetate. For the tert-butyl ester compounds, the solution was washed with saturated aqueous $NaHCO_3$. The aqueous phase was then adjusted to pH 2 and extracted with ethyl acetate. The organic phase for either case was then washed with saturated aqueous NaCl and dried over $MgSO_4$. The solution was stripped free of solvent on a rotary evaporator to yield the product.

GENERAL PROCEDURE G

N-Alkylation

To a solution of 3-aminoquinoline in $CH_2Cl_2$ was added 1.1 equivalent of triethylamine, followed by a $CH_2Cl_2$ solution of p-nitrobenzenesulfonyl (nosyl) chloride. The reaction was stirred at room temperature for 5 hours, then the di-nosylated aminoquinoline was isolated by filtration and was washed with ethyl acetate. This material was then added to a 1:1 mixture of dioxane and 1N NaOH and this solution was heated to 60° C. for 4 hours, at which time all solids had dissolved. The reaction was cooled to room temperature, then the pH was adjusted to ~4. The precipitated mono-nosylated aminoquinoline was removed by filtration and washed with $H_2O$. A solution of this compound in THF was then added to a −78° C. suspension of NaH in THF, then ethyl 2-bromopropionate was added. The reaction was warmed to rt, then refluxed for 4 days. The crude reaction mixture was stripped free of solvent on a rotary evaporator, and the alkylated, nosylated aminoquinoline was obtained by chromatography. This product was then dissolved in DMF and 3 equivalents $K_2CO_3$ was added, followed by 1.2 equivalents of thiophenol. The reaction was stirred overnight at room temperature. The reaction was then quenched with water and ether, and the organic phase was washed with saturated aqueous $NaHCO_3$ and saturated aqueous NaCl, then dried over $MgSO_4$. The solution was stripped free of solvent on a rotary evaporator to yield the crude product, which was then purified through chromatography.

GENERAL PROCEDURE H

Ester/Amide Exchange

To a solution of 3 equivalents of the desired amine in 1,2-dichloroethane was added 5.2 equivalents trimethylaluminum wherein said addition was conducted below the surface of the solution via syringe. After stirring for 30 minutes at room temperature, a solution of the desired ester dissolved in 1,2-dichloroethane was added. The reaction was refluxed until tlc showed complete conversion, typically 3 hours. The reaction was then cooled to 0° C. and quenched with 10% HCl (Note: the acid should be added slowly as some foaming occurs during its addition). For those products not soluble in aqueous acid, the mixture was transferred to a separatory funnel and the layers were separated. The aqueous phase was washed with ethyl acetate, and the organic phases were washed with saturated aqueous NaCl, dried over $MgSO_4$, and concentrated under reduced pressure to leave the crude product.

For products soluble in aqueous acid, after reaction quench, the reaction volume was reduced to ~⅓ of initial volume under reduced pressure. To the resulting solution was added 20% aqueous potassium sodium tartrate (Rochelle's salt) and ethyl acetate. The pH of the solution was adjusted to ~13, and the aluminum salts dissolved in the aqueous solution. The organic phase was separated, and the aqueous phase was extracted with ethyl acetate. The combined organic solution was washed with saturated aqueous NaCl, dried over $MgSO_4$, and concentrated under reduced pressure to leave the crude product.

GENERAL PROCEDURE I

Ester Reduction to Alcohol

To a 0° C. solution of the starting ester in anhydrous THF was added 1.0 equivalent of $LiBH_4$ in THF. The reaction was stirred at room temperature overnight, and was then quenched with water. The THF was removed on a rotary evaporator, and ethyl acetate was added, and the phases were separated. The organic phase was washed with saturated aqueous NaCl, dried over $MgSO_4$, and concentrated under reduced pressure to leave the product.

GENERAL PROCEDURE J

Triflate Displacement

To a 0° C. solution of isobutyl R-(+)-lactate in $CH_2Cl_2$ was added 1.1 equivalents of trifluoromethanesulfonic anhydride. After stirring at room temperature for 20 minutes, 1.1 equivalents of 2,6-lutidine was added and stirring was continued for 10 min. This solution was then transferred to a flask containing 1 equivalent arylamine and 1 equivalent diisopropylethylamine in $CH_2Cl_2$ or $CH_3NO_2$ at 0° C. The reaction was held overnight at room temperature, then stripped free of solvent on a rotary evaporator. The residue was dissolved in ethyl acetate, washed with 5% citric acid, followed by saturated aqueous NaCl, and then the solution was stripped free of solvent on a rotary evaporator to yield the crude product, which was-then purified by chromatography.

GENERAL PROCEDURE K

Methyl Ester Formation from Amino Acids

The amino acid (amino acid or amino acid hydrochloride) is suspended in methanol and chilled to 0° C. HCl gas is bubbled through this solution for 5 min. The reaction is allowed to warm to room temperature then stirred for 4 hours. The solvents are then removed to afford the desired amino acid methyl ester hydrochloride. This product is usually used without further purification.

Example A

Synthesis of N-(3,4-dichlorophenyl)-D,L-alanine

Using the procedure set forth in U.S. Pat. No. 3,598,859, the disclosure of which is incorporated herein by reference in its entirety, N-(3,4-dichlorophenyl)-D,L-alanine was prepared. Specifically, to a solution of 3,4-dichloroaniline (1 equivalent) (Aldrich) in isopropanol (about 500 mL per mole of 3,4-dichloroaniline) is added water (about 0.06 mL per mL of isopropanol) and 2-chloropropionic acid (2 equivalents) (Aldrich). This mixture is warmed to 40° C. and sodium bicarbonate (0.25 equivalents) is added in successive portions before heating under reflux for 4–5 days. After cooling, the reaction mixture is poured into water and the unreacted 3,4-dichloroaniline is removed by filtration. The filtrate is acidified to pH 3–4 with concentrated hydrochloric acid and the resultant precipitate is filtered, washed and dried to yield the tide compound, m.p.=148–149° C.

Alternatively, following General Procedure A above and using 3,4-dichloroaniline (Aldrich) and ethyl pyruvate (Aldrich), N-(3,4-dichlorophenyl)-D,L-alanine ethyl ester was prepared as an oil. The reaction was monitored by tlc on silica gel (Rf=0.4 in 25% EtOAc/Hexanes) and purification was by preparative plate chromatography (silica gel using 25% EtOAc/Hexanes as eluent).

NMR data was as follows:

$^1$H-nmr (CDCl$_3$): δ=7.2 (d, 1H); 6.7 (d, 1H,); 6.4 (dd, 1H); 4.30 (bs, 1H); 4.2 (q, 2H); 4.1 (q, 1H); 1.5 (d, 3H); 1.3 (t, 3H).

$^{13}$C-nmr (CDCl$_3$): δ=175; 146.7; 133; 131; 121; 114.9; 112.6; 72.0; 52.4; 28.3; 19.5.

$C_{11}H_{13}Cl_2NO_2$ (MW=262.14); mass spectroscopy (MH$^+$) 263.

Hydrolysis of this ester via, e.g., General Procedure C provides the title compound.

Example B

Synthesis of N-(3,5-dichlorophenyl)-D,L-alanine

Using the procedure set forth in U.S. Pat. No. 3,598,859 (or Example A above), N-(3,5-dichlorophenyl)-D,L-alanine was prepared using 3,5-dichloroaniline (Aldrich) and 2-chloropropionic acid (Aldrich).

Example C

Synthesis of N-(3,5-difluorophenyl)-D,L-alanine

Using the procedure set forth in U.S. Pat. No. 3,598,859 (or Example A above), N-(3,5-difluorophenyl)-D,L-alanine was prepared using 3,5-difluoroaniline (Aldrich) and 2-chloropropionic acid (Aldrich).

Example D

Synthesis of L-Valine N,N-dimethyl amide

To a stirred solution of 2.51 g (10 mmol) of Cbz-L-Valine (Bachem) in 20 mL of DMF was added 1.46 g (9 mmol) of CDI and the mixture was stirred for 50 min. To this mixture was added 6 mL (12 mmol) of dimethylamine (Aldrich) in 5 mL of THF and the reaction mixture was stirred for 18 hours. The mixture was taken up in 100 mL of ethyl acetate, washed with 10% HCl (3×40 mL), 10 mL of brine, and 20% potassium carbonate (2×50 mL), and dried over MgSO$_4$. The mixture was filtered and concentrated to yield Cbz-L-valine N,N-dimethyl amide, which was hydrogenated under standard conditions with 10% Pd/C as the catalyst to remove the Cbz group and provide the title compound as an oil.

NMR data was as follows:

$^1$H-nmr (CDCl$_3$): δ=3.47 (d, J=5.4 Hz, 1H), 3.03 (s, 3H), 2.96 (s, 3H), 1.83 (m, 1H), 1.60 (s, 2H), 0.95 (d, J=6.8 Hz, 3H), 0.89 (d, J=6.8 Hz, 3H).

$^{13}$C-nmr (CDCl$_3$): δ=175.1, 56.2, 37.0, 35.7, 32.0, 19.9, 16.8.

Example E

Synthesis of L-Valine N-methyl amide

The title compound was prepared following the procedure described in Example D above and using methylamine in place of dimethylamine. The title compound was an oil.

NMR data was as follows:

$^1$H-nmr (CDCl$_3$): δ=7.27 (bs, 1H), 3.20 (d, J=3.8 Hz, 1H), 2.79 (d, J=5.0 Hz, 3H), 2.27 (m, 1H), 1.40 (bs, 2H), 0.96 (d, J=7.1 Hz, 3H), 0.79 (d, J=6.8 Hz, 3H).

$^{13}$C-nmr (CDCl$_3$): δ=175.0, 60.1, 30.7, 25.6, 19.7, 15.9.

Example F

Synthesis of BOC-Norleucine amide

To a stirred mixture of 3.47 g (15 mmol) of BOC-norleucine (Bachem), 3.44 g (22.5 mmol) of 1-hydroxybenzotriazole monohydrate and 50 mL of dichloromethane at 0° C. was added 3.45 g (1.2 mmol) of EDC. The resulting mixture was stirred at 0° C. for 1 hour and then ammonia gas was bubbled through the mixture for 10 min. The cooling bath was allowed to warm to room temperature and the mixture stirred for 18 hours. The mixture was evaporated to dryness, triturated with 20% Na$_2$CO$_3$. The resulting solid was collected by filtration and washed with water to yield 2.69 g (11.7 mmol, 78%) of the title compound.

Example G

Synthesis of N-[3,5-di(trifluoromethyl)phenyl]-L-alanine

Step A: Following General Procedure J and using 3,5-di(trifluoromethyl)aniline (Aldrich) and isobutyl R-(+)-lactate (Aldrich), N-[3,5-di(trifluoromethyl)phenyl]-L-alanine isobutyl ester was prepared as an oil. The reaction was monitored by silica gel tlc (Rf=0.38 in 10% EtOAc/hexanes). Purification was by preparative plate thin layer chromatography using 10% EtOAc/hexanes as the eluant.

NMR data was as follows:

$^1$H-nmr (CDCl$_3$): δ=7.13 (s, 1H), 6.91 (s, 2H), 4.97 (d, J=8.24 Hz, 1H), 4.18 (m, 1H), 3.93 (d, J=6.59 Hz, 2H), 1.93 (sept, J=6.71 Hz, 1H), 1.49 (d, J=7.02 Hz, 3H), 0.89 (d, J=6.59 Hz, 6H).

$^{13}$C-nmr (CDCl$_3$): δ=174.4, 147.9, 133.6, 133.2, 132.7, 132.3, 129.4, 125.8, 122.2, 118.6, 112.81, 112.76, 111.42, 111.37, 111.32, 111.27, 111.22, 72.2, 52.0, 32.1, 28.24, 28.17, 23.2, 19.5, 19.3, 19.2, 18.9, 14.6.

$C_{15}H_{17}F_6NO_2$ (MW=357.30); mass spectroscopy (MH$^+$) 358.

Step B: N-[3,5-Di(trifluoromethyl)phenyl]-L-alanine isobutyl ester was then hydrolyzed according to General Procedure C using lithium hydroxide in THF.

Example H

Synthesis of N-(3,5-dimethoxyphenyl)-D,L-alanine

The title compound was prepared according to the procedure described in U.S. Pat. No. 3,598,859 (or Example A above) using 3,5-dimethoxyaniline (Aldrich) and 2-chloropropionic acid (Aldrich).

Example I

Synthesis of N-(3,4-dichlorophenyl)glycine

Using the procedure set forth in U.S. Pat. No. 3,598,859, N-(3,4-dichlorophenyl)glycine was prepared using 3,4-dichloroaniline (Aldrich) and 2-chloroacetic acid (Aldrich).

Example J

Synthesis of N-(3,5-dichlorophenyl)-D,L-phenylglycine 3,5-Dichloroaniline (1 eq.) (Aldrich) and methyl α-bromophenylacetate (1 eq.) (Aldrich) were refluxed in ethanol with N-methyl morpholine (Aldrich) for 3 days. After standard work-up, the residue was crystallized from ethyl acetate/hexane/ether/water to afford methyl N-(3,5-dichlorophenyl)-D,L-phenylglycine. The methyl ester was then hydrolyzed using 1M NaOH/water in methanol to afford the title compound.

Example 1

Synthesis of N-[N-(3,4-dichlorophenyl)-D,L-alanyl]-L-valine methyl ester

Following General Procedure D (without the 1N HCl wash) and using L-valine methyl ester hydrochloride (Sigma) and N-(3,4-dichlorophenyl)alanine (from Example A above), the title compound was prepared.

NMR data was as follows:

$^1$H-nmr (CDCl$_3$): δ=7.20 (m, 1H), 6.92–7.03 (m, 1H), 6.69 (m, 1H), 6.44 (m, 1H), 4.50 (m, 1H), 4.19 (m, 1H), 3.78 (m, 1H), 3.71 (s, 1.5H), 3.65 (s, 1.5H), 2.12 (m, 1H), 1.50 (d, J=7.0 Hz, 3H), 0.80–0.92 (m, 4.5H 0.71 (d, J=6.8 Hz, 1.5H).

$^{13}$C-nmr (CDCl$_3$): δ=173.4, 173.0, 172.2, 171.8, 146.0, 145.8, 132.9, 132.8, 130.7, 130.6, 121.7, 115.1, 114.8, 113.5, 113.1, 56.9, 56.6, 55.1, 54.8, 52.2, 52.1, 31.1, 31.0, 30.9, 19.6, 19.4, 17.7, 17.4.

Example 2

Synthesis of N-[N-(3,4-dichlorophenyl)-D,L-alanyl]-L-valine N-iso-butyl amide

Following General Procedure H above and using N-[N-(3,4-dichlorophenyl)-D,L-alanyl]-L-valine methyl ester (from Example 1 above) and isobutylamine (Aldrich), the title compound was prepared as a oil. The reaction was monitored by tlc (Rf=0.3 in 10% methanol/dichloromethane).

NMR data was as follows:

$^1$H-nmr (CDCl$_3$): δ=7.2 (d, 1H), 7.0 (m, 1H), 6.7 (m, 1H), 6.4 (m, 1H), 4.6 (m, 1H), 4.1 (m, 1H), 3.8 (m, 3H), 3.6 (s, 3H), 1.9 (m, 2H), 1.4 (d, 3H), 1.1 (m, 6H), 0.9 (m, 6H).

$^{13}$C-nmr (CDCl$_3$): δ=173.8, 173.4, 172.9, 146.6, 133.6, 133.4, 131.3, 122.5, 122.4, 115.8, 113.8, 56.9, 55.7, 38.2, 25.6, 20, 16, 12.1.

$C_{18}H_{27}N_3O_2Cl_2$ (MW=388.3); mass spectroscopy (MH$^+$) 389.

Example 3

N-[N-(3,4-dichlorophenyl)-D,L-alanyl]-L-threonine methyl ester

Following General Procedure D (without the 1N HCl wash) and using N-(3,4-dichlorophenyl)-D,L-alanine (from Example A above) and L-threonine methyl ester hydrochloride (Sigma), the title compound was prepared as a oil. The reaction product was purified by silica gel chromatography using 50% ethyl acetate/hexane.

NMR data was as follows:

$^1$H-nmr (CDCl$_3$): δ=1.06 (d, J=6.4) and 1.17 (d, J=6.3; 3H total in 2:1 ratio), 1.53 (d, J=7, 3H), 2.31 (d, J=5.6) and 2.58 (d, J=4.7; 1H total in 2:1 ratio), 3.68 (s) and 3.75 (s) (3H total in 1:2 ratio), 3.8–3.9 (m, 1H), 4.15–4.25 (m, 1H), 4.3–4.45 (m, 1H), 4.5–4.6 (m, 1H), 6.4–6.5 (m, 1H), 6.65–6.7 (m, 1H), 7.4–7.55 (m, 2H).

$^{13}$C-nmr (CDCl$_3$): δ=19.96, 20.23, 20.39, 20.49, 53.23, 53.28, 55.35, 55.59, 57.5, 68.13, 68.21, 113.72, 114.20, 115.42, 115.60, 122.26, 122.35, 131.22, 131.33, 133.41, 133.55, 146.47, 146.6, 171.63, 171.80, 174.69, 174.86.

$C_{14}H_{18}N_2O_4Cl_2$ (MW=349.22); mass spectroscopy (MH$^+$) 349.

Example 4

Synthesis of N-[N-(3,4-dichlorophenyl)-D,L-alanyl]-L-valine methyl ester

Following General Procedure D (without the 1N HCl wash) and using N-(3,4-dichlorophenyl)-D,L-alanine (from Example A above) and L-valine ethyl ester HCl, the title compound was prepared as a oil. The reaction product was purified by silica gel chromatography using 35% ethyl acetate/hexane.

NMR data was as follows:

$^1$H-nmr (CDCl$_3$): δ=0.7–1.0 (overlapping group of d, J=7, 6H), 1.19 and 1.27 (pair of t, J=7, 3H), 1.5 (d, J=7, 3H), 2.05–2.2 (m, 1H), 3.7–3.9 (m, 1H), 4.0–4.3 (m, 3H), 4.5–4.6 (m, 1H), 6.4–6.5 (m, 1H), 6.5–6.6 (m, 1H), 6.9–7.1 (M, 1H), 7.2–7.3 (M, 1H).

$^{13}$C-nmr (CDCl$_3$): δ=14.65, 14.77, 17.96, 18.25, 19.56, 20.06, 20.31, 31.77, 31.81, 55.50, 55.73, 57.22, 57.46, 61.88, 61.94, 113.76, 114.01, 115.48, 115.76, 122.40, 122.46, 131.30, 131.33, 133.48, 133.61, 146.41, 146.60, 171.86, 172.36, 173.54, 173.84.

$C_{16}H_{22}N_2O_3Cl_2$ (MW=361.27); mass spectroscopy (MH$^+$) 361.

Example 5

Synthesis of N-[N-(3,4-dichlorophenyl)-D,L-alanyl]-L-valine-tert-butyl ester Following General Procedure D (without the 1N HCl wash) and using N-(3,4-dichlorophenyl)-D,L-alanine (from Example A above) and L-valine tert-butyl ester hydrochloride (Sigma), the title compound was prepared as a oil. The reaction product was purified by silica gel chromatography using 25% ethyl acetate/hexane.

NMR data was as follows:

$^1$H-nmr (CDCl$_3$): δ=0.7–1.0 (overlapping group of d, J=7, 6H), 1.36 (s) and 1.45 (s) (9H), 1.5–1.54 (2 d, J=7, 3H), 2.0–2.2 (m, 1H), 3.7–3.85 (m, 1H), 4.1–4.2 (m, 1H), 4.3–4.5 (m, 1H), 6.4–6.5 (m, 1H), 6.7 (s, 1H), 6.9–7.1 (m, 1H), 7.15–7.3 (m, 1H).

$^{13}$C-nmr (CDCl$_3$): δ=17.84, 18.25, 19.50, 20.06, 20.29, 29.42, 28.62, 31.96, 32.16, 55.45, 55.65, 57.53, 57.92, 82.72, 113.75, 114.00, 115.43, 115.65, 122.26, 122.32, 131.29, 131.50, 146.46, 146.65, 170.88, 171.48, 173.39, 173.65.

$C_{18}H_{26}N_2O_3Cl_2$ (MW=389.33); mass spectroscopy (MH$^+$) 389.

Example 6

Synthesis of N-[N-(3,4-dichlorophenyl)-D,L-alanyl]-L-valine amide

Following General Procedure D (without the 1N HCl wash) and using N-(3,4-dichlorophenyl)-D,L-alanine (from Example A above) and L-valine amide hydrochloride (Sigma), the title compound was prepared as a solid having a melting point of 156–158° C. The reaction product was purified by silica gel chromatography using 90:10:1 CH$_2$Cl$_2$:MeOH:NH$_4$OH.

NMR data was as follows:

$^1$H-nmr (DMSO-d$_6$): δ=0.6–0.9 (m, 6H), 1.2–1.4 (overlapping d, 3H), 1.8–2.0 (m, 1H), 3.9–4.2 (m, 2H), 6.3–6.4 (m, 1H), 6.35–6.4 (m, 1H), 6.7–6.8 (m, 1H), 7.0–7.15 (m, 1H), 7.2–7.3 (m, 1H), 7.4 (bs, 1H), 7.8 (d, J=10) and 8.0 (d, J=10) (total 1H in 3:2 ratio).

$^{13}$C-nmr (DMSO-d$_6$): δ=17.8, 18.2, 19.00, 19.25, 19.6, 19.7, 31.16, 31.20, 51.9, 52.7, 57.11, 57.4, 113.46, 113.58, 113.67, 113.85, 117.20, 117.45, 130.64, 130.76, 131.53, 131.56; 148.25, 148.45, 173.06, 173.11, 173.38, 173.51.

$C_{14}H_{19}N_3O_2Cl_2$ (MW=331); mass spectroscopy (MH$^+$) 332.

Example 7

Synthesis of N-[N-(3,4-dichlorophenyl)-L-alanine N-(1-hydroxy-3-methyl-2-butyl)amide Following General Procedure D (without the 1N HCl wash) and using N-(3,4-dichlorophenyl)-D,L-alanine (from Example A above) and valinol (Sigma), the title compound was prepared as an oil. The reaction product was purified by silica gel chromatography using 45:55 EtOAc/hexanes and 90:10:1 CH$_2$Cl$_2$:MeOH:NH$_4$OH.

NMR data was as follows:

$^1$H-nmr (DMSO-d$_6$): δ=0.86 (d, J=7, 3H), 0.91 (d, J=7, 3H), 1.50 (d, J=7, 3H), 1.8–2.0 (m, 1H), 2.6 (bs, 1H), 3.5–3.8 (m, 4H), 4.1 (bs, 1H), 6.45 (dd, J=2.8, 8.7, 1H), 6.7 (d, J=2.8, 1H), 6.8 (bd, 1H), 7.2 (d, J=5, 1H).

$^{13}$C-nmr (DMSO)-d$_6$): δ=19.3, 20.1, 20.2, 29.5, 55.8, 57.4, 64.1, 113.7, 115.7, 122.4, 131.4, 133.5, 146.6, 174.6.

$C_{14}H_{20}N_2O_2Cl_2$ (MW=319.23); mass spectroscopy (MH$^+$) 319.

Example 8

Synthesis of N-[N-(3,4-dichlorophenyl)-D,L-alanyl]-L-valine N,N-dimethyl amide Following General Procedure D and using valine N,N-dimethyl amide (from Example D above) and N-(3,4-dichlorophenyl)-D,L-alanine (from Example A above), the title compound was prepared as a solid (mp=145–160° C.).

NMR data was as follows:

$^1$H-nmr (CDCl$_3$): δ=7.38 (m, 1H), 7.14 (m, 1H), 6.66 (m, 1H), 6.41 (m, 1H), 4.78 (m, 1H), 3.88 (m, 1H), 3.10 and 3.09 (s,s, 3H), 2.94 and 2.90 (s,s, 3H), 1.96 (m, 1H), 1.43 (m 3H), 0.88 and 0.67 (m, 6H).

$^{13}$C-nmr (CDCl$_3$): δ=173.6, 173.1, 171.4, 171.3, 146.3, 146.0, 132.7, 132.6, 130.52, 130.46, 120.9, 120.8, 114.5, 113.4, 113.0, 54.25, 54.15, 53.4, 53.2, 37.4, 35.6, 31.4, 31.3, 19.50, 19.46, 19.2, 17.5, 17.0.

$C_{16}H_{23}N_3O_2Cl_2$ (MW=360.29); mass spectroscopy (MH$^+$) 360.

Example 9

Synthesis of N-[N-(3,4-dichlorophenyl)-D,L-alanyl]-L-valine N-methyl amide

Following General Procedure D and using L-valine N-methyl amide (from Example E above) and N-(3,4-dichlorophenyl)-D,L-alanine (from Example A above), the title compound was prepared as a solid (mp=145–160° C.).

NMR data was as follows:

$^1$H-nmr (DMSO-d$_6$) δ=8.10 and 7.90 (m, 2H), 7.23 (m, 1H), 6.76 and 6.69 (m, 1H), 6.57 (m, 1H), 6.34 (m, 1H), 3.90–4.14 (m, 2H), 2.57 and 2.56 (s, s, 3H), 1.88 (m, 1H), 1.27 (m, 3H), 0.65–0.86 (m, 6H).

$^{13}$C-nmr (DMSO-d$_6$): δ=173.1, 171.2, 171.1, 148.1, 147.9, 131.19, 131.16, 130.4, 130.2, 116.8, 113.5, 113.2, 113.1, 57.5, 57.3, 52.2, 51.5, 30.9, 30.8, 25.4, 19.2, 19.1, 18.8, 18.6, 18.2, 17.9.

$C_{15}H_{21}N_3O_2Cl_2$ (MW=346.26); mass spectroscopy (MH$^+$) 346.

Example 10

Synthesis of N-[N-(3,4-dichlorophenyl)-D,L-alanyl]-L-alanine methyl ester

Following General Procedure D (without the 1N HCl wash) and using L-alanine methyl ester hydrochloride (Sigma) and N-(3,4-dichlorophenyl)-D,L-alanine (from Example A above), the title compound was prepared as an oil. The reaction was monitored by tlc (Rf=0.24 in 1:1 EtOAc:Hexanes) and the product was purified by flash chromatography using 1:1 EtOAc:Hexanes as the eluent.

NMR data was as follows:

$^1$H-nmr (CDCl$_3$) δ=7.15 (m, 2H), 6.63 (dd, 1H), 6.40 (m, 1H), 4.50 (m, 2H), 3.75 (m, 1H), 3.67 (s, 1.5H), 3.61 (s, 1.5H), 1.45 (d, 3H), 1.31 (m, 3H).

<sup>13</sup>C-nmr (CDCl$_3$): δ=173.5, 173.2, 173.0, 172.8, 146.3, 146.2, 132.6, 130.6, 130.5, 121.2, 114.9, 114.7, 113.3, 113.0, 54.6, 54.5, 52.43, 52.39, 47.9, 47.8, 19.3, 19.1, 17.9, 17.8.

C$_{13}$H$_{16}$N$_2$O$_3$Cl$_2$ (MW=319.19); mass spectroscopy (MH$^+$) 319.

Example 11

Synthesis of N-[N-(3,4-dichlorophenyl)-L-alanyl]-L-leucine methyl ester

Following General Procedure D and using L-leucine methyl ester hydrochloride (Sigma) and N-(3,4-dichlorophenyl)-D,L-alanine (from Example A above), the tide compound was prepared as a solid (mp=120–132° C.). The reaction was monitored by tlc (Rf=0.49 in 1:1 EtOAc:Hexanes) and the product was purified by flash chromatography using 1:1 EtOAc:Hexanes as the eluent.

NMR data was as follows:

$^1$H-nmr (CDCl$_3$) δ=7.18 (d, 1H), 6.95 (bd, 1H), 6.69 (d, 1H), 6.43 (dd, 1H), 4.58 (m, 1H), 4.32 (d, 1H), 3.75 (m, 1H), 3.61 (s, 3H), 1.54 (m, 6H), 0.90 (m, 6H).

$^{13}$C-nmr (CDCl$_3$): δ=174.1, 173.4, 146.8, 133.3, 131.2, 122.2, 115.7, 114.1, 55.5, 52.9, 51.1, 41.6, 25.5, 23.4, 22.2, 20.0.

C$_{16}$H$_{22}$N$_2$O$_3$Cl$_2$ (MW=361.27); mass spectroscopy (MH$^+$) 361.1.

Example 12

Synthesis of N-[N-(3,4-dichlorophenyl)-L-alanyl]-L-phenylalanine methyl ester

Following General Procedure D and using L-phenylalanine methyl ester hydrochloride (Sigma) and N-(3,4-dichlorophenyl)-D,L-alanine (from Example A above), the title compound was prepared as a solid (mp=122–124.5° C.). The reaction was monitored by tlc (Rf=0.47 in 1:1 EtOAc:Hexanes) and the product was purified by flash chromatography using 1:1 EtOAc:Hexanes as the eluent.

NMR data was as follows:

$^1$H-nmr (CDCl$_3$) δ=7.21 (m, 4H), 7.05 (m, 2H), 6.91(d, 1H), 6.64 (d, 1H), 6.38 (dd, 1H), 4.84 (q, 1H), 4.05 (bs, 1H), 3.71 (m, 4H), 3.20 (m, 1H), 3.04 (m, 1H), 1.37 (d, 3H).

$^{13}$C-nmr (CDCl$_3$): δ=173.6, 172.1, 146.5, 136.2, 133.4, 131.2, 129.7, 129.1, 127.7, 122.3, 115.6, 113.9, 55.4, 53.3, 53.0, 38.1, 19.9.

C$_{19}$H$_{20}$N$_2$O$_3$Cl$_2$ (MW=395.29); mass spectroscopy (MH$^+$) 395.

Example 13

Synthesis of N-[N-(3,4-dichlorophenyl)-D,L-alanyl]-L-isoleucine methyl ester

Following General Procedure D (without the 1N HCl wash) and using L-isoleucine methyl ester hydrochloride (Sigma) and N-(3,4-dichlorophenyl)-D,L-alanine (from Example A above), the title compound was prepared as a solid (mp=95.5–101.5° C.). The reaction was monitored by tlc (Rf=0.62 in 1:1 EtOAc:Hexanes) and the product was purified by flash chromatography using 1:1 EtOAc:Hexanes as the eluent.

NMR data was as follows:

$^1$H-nmr (CDCl$_3$) δ=7.21 (d, 1H), 6.98 (m, 1H), 6.70 (m, 1H), 6.45 (m, 1H), 4.55 (m, 1H), 4.11 (m, 1H), 3.79 (m, 1H), 3.72 (s, 1.5H), 3.67 (s, 1.5H), 1.87 (m, 1H), 1.51 (d, 3H), 1.10 (m, 8H).

$^{13}$C-nmr (CDCl$_3$): δ=173.8, 173.4, 172.9, 172.4, 146.6, 146.4, 133.6, 133.4, 131.30, 131.28, 122.5, 122.4, 115.8, 115.4, 114.1, 113.8, 56.9, 56.8, 55.7, 55.5, 52.8, 52.7, 38.3, 38.2, 25.6, 25.5, 20.2, 20.0, 16.05, 16.03, 12.1, 12.0.

C$_{16}$H$_{22}$N$_2$O$_3$Cl$_2$ (MW=361.27); mass spectroscopy (MH$^+$) 361.1.

Example 14

Synthesis of N-[N-(3,4-dichlorophenyl)-L-alanyl]-(S)-2-aminopentanoic acid methyl ester Following General Procedure D (without the 1N HCl wash) and using L-norvaline methyl ester hydrochloride (Sennchem) and N-(3,4-dichlorophenyl)-D,L-alanine (from Example A above), the title compound was prepared as a solid (mp=150–153° C.). The reaction was monitored by tlc (Rf=0.57 in 1:1 EtOAc:Hexanes) and the product was purified by flash chromatography using 1:1 EtOAc:Hexanes as the eluent.

NMR data was as follows:

$^1$H-nmr (CDCl$_3$) δ=7.21 (d, 1H), 6.95 (bd, 1H), 6.70 (d, 1H), 6.47 (dd, 1H), 4.57 (m, 1H), 4.13 (bd, 1H), 3.78 (m, 1H), 3.67 (s, 3H), 1.81 (m, 1H) 1.62 (m, 1H), 1.51 (d, 3H), 1.30 (m, 2H), 0.9 (t, 3H).

$^{13}$C-nmr (CDCl$_3$): δ=173.8, 173.0, 146.6, 133.4, 1313, 122.4, 115.7, 114.1, 55.6, 52.9, 52.4, 34.8, 20.2, 19.2, 14.2.

C$_{15}$H$_{20}$N$_2$O$_3$Cl$_2$ (MW 347.24); mass spectroscopy (M$^+$) 347.

Example 15

Synthesis of N-[N-(3,4dichlorophenyl)-L-alanyl]-(S)-2-aminopentanoic acid methyl ester Following General Procedure D (without the 1N HCl wash) and using L-norleucine methyl ester hydrochloride (Sigma) and N-(3,4-dichlorophenyl)alanine (from Example A above), the title compound was prepared as a solid (mp=163–165° C.). The reaction was monitored by tlc (Rf=0.55 in 1:1 EtOAc:Hexanes) and the product was purified by flash chromatography using 1:1 EtOAc:Hexanes as the eluent.

NMR data was as follows:

$^1$H-nmr (CDCl$_3$) δ=7.18 (d, 1H, J=8.7 Hz), 6.99 (bd, 1H, J=8.2 Hz), 6.69 (d, 1H, J=2.7 Hz), 6.45 (dd, 1H, J=8.7 Hz, J=2.7 Hz), 4.53 (m, 1H), 4.23 (d, 1H, J=4.2 Hz), 3.77 (m, 1H), 3.66 (s, 3H), 1.83 (m, 1H), 1.62 (m, 1H), 1.48 (d, 3H, J=7.0 Hz), 1.27 (m, 4H), 0.85 (t, 3H).

$^{13}$C-nmr (CDCl$_3$): δ=173.9, 173.1, 146.7, 133.4, 131.2, 122.3, 115.7, 114.1, 55.5, 52.9, 52.6, 32.4, 28.0, 22.8, 20.1, 14.4.

C$_{16}$H$_{22}$N$_2$O$_3$Cl$_2$ (MW=361.27); mass spectroscopy (MH$^+$) 361.

Example 16

Synthesis of N-[N-(3,4dichlorophenyl)-D,L-alanyl]-L-tryptophan methyl ester

Following General Procedure D (without the 1N HCl wash) and using L-tryptophan methyl ester hydrochloride (Sigma) and N-(3,4-dichlorophenyl)-1D,L-alanine (from Example A above), the title compound was prepared as a solid (mp=54–66° C.). The reaction was monitored by tlc (Rf=0.43 in 1:1 EtOAc:Hexanes) and the product was purified by flash chromatography using 1:1 EtOAc:Hexanes as the eluent.

NMR data was as follows:

¹H-nmr (CDCl₃) δ=8.15 (s, 0.5H), 7.98 (s, 0.5H), 7.51 (d, 0.5H), 7.12 (m, 6H), 6.60 (d, 0.5H), 6.53 (dd, 1H), 6.24 (m, 1H), 4.88 (m, 1H), 3.90 (d, 0.5H), 3.70 (m, 4.5H), 3.32 (m, 1H), 3.22 (m, 1H), 1.40 (m, 3H).

¹³C-nmr (CDCl₃): δ=173.8, 173.6, 172.8, 172.4, 146.4, 146.3, 136.6, 133.3, 133.2, 131.2, 131.1, 128.2, 127.7, 123.3, 122.8, 122.05, 122.02, 120.3, 120.2, 119.0, 118.7, 115.5, 115.4, 113.8, 113.3, 112.1, 111.9, 110.2, 109.9, 55.3, 55.1, 53.5, 53.1, 53.0, 52.9, 27.9, 27.7, 19.8, 19.6.

$C_{21}H_{21}N_3O_3Cl_2$ (MW=434.33); mass spectroscopy (MH⁺) 434.

Example 17

Synthesis of N-[N-(3,4dichlorophenyl)-D,L-alanyl]-L-aspartic β-(tert-butyl ester)α-methyl ester Following General Procedure D (without the 1N HCl wash) and using L-aspartic acid β-(tert-butyl ester) α-methyl ester hydrochloride (Bachem) and (3,4-dichlorophenyl)-D,L-alanine (from Example A above), the title compound was prepared. The reaction was monitored by tlc (Rf=0.56 in 1:1 EtOAc:Hexanes) and the product was purified by flash chromatography using 1:1 EtOAc:Hexanes as the eluent.

NMR data was as follows:

¹H-nmr (CDCl₃) δ=7.52 (d, 0.5H), 7.42 (d, 0.5H), 7.13 (m, 1H), 6.66 (d, 0.5H), 6.60 (d, 0.5H), 6.40 (m, 1H), 4.76 (m, 1H), 4.40 (d, 0.5H), 4.31 (d, 0.5H), 3.75 (m, 1H), 3.69 (s, 1.5H), 3.62 (s, 1.5H), 2.88 (m, 1H), 2.62 (m, 1H), 1.47 (m, 3H), 1.32 (s, 4.5H), 1.21 (s, 4.5H).

¹³C-nmr (CDCl₃): δ=174.0, 173.7, 171.7, 171.4, 170.30, 170.27, 146.7, 146.6, 133.4, 133.3, 131.2, 131.1, 122.0, 115.6, 115.1, 114.0, 113.4, 82.4, 55.4, 55.2, 53.24, 53.19, 49.0, 48.7, 37.9, 37.8, 28.4, 28.2, 19.9, 19.8.

$CH_{18}H_{24}N_2O_5Cl_2$ (MW=419.31); mass spectroscopy (MH⁺) 418.

Example 18

Synthesis of N-[N-(3,4dichlorophenyl)-D,L-alanyl]-L-aspartic α-methyl ester

The tert-butyl ester group of N-[N-(3,4-dichlorophenyl)-D,L-alanyl]-L-aspartic acid β-(tert-butyl ester) α-methyl ester (from Example 17 above) was removed via General Procedure F to provide for the title compound as a solid (mp=53.5–56° C.). The reaction was monitored by tlc (Rf=0.54 in 1:1 EtOAc:Hexanes).

NMR data was as follows:

¹H-nmr (CDCl₃) δ=7.59 (d, 1H), 7.18 (m, 1H), 6.79 (d, 0.5H), 6.69 (d, 0.5H), 6.58 (m, 0.5H), 6.47 (m, 0.5H), 4.84 (m, 1H), 3.82 (m, 1H), 3.73 (s, 1.5H), 3.68 (s, 1.5H), 3.04 (m, 1H), 2.79 (m, 0.5H), 2.73 (m, 0.5H), 1.49 (m, 3H).

¹³C-nmr (CDCl₃): δ=175.7, 175.6, 175.14, 175.07, 171.1, 171.0, 145.0, 144.6, 133.6, 133.5, 131.44, 131.40, 124.2, 123.4, 55.9, 55.4, 53.8, 53.7, 49.05, 49.00, 36.1 19.2 19.1.

$C_{14}H_{16}N_2O_5Cl_2$ (MW=363.20); mass spectroscopy (M⁺) 363.

Example 19

Synthesis of N-[N-(3,4dichlorophenyl)-D,L-alanyl]-Nε-BOC-L-lysine methyl ester

Following General Procedure D and using N-(3,4-dichlorophenyl)-D,L-alanine (from Example A above) and Nε-BOC-L-lysine methyl ester hydrochloride (Bachem), the title compound was prepared as a oil. The reaction was monitored by tlc (Rf=0.23 in 45% ethyl acetate/hexanes).

NMR data was as follows:

¹H-nmr (CDCl₃): δ=7.22 (m, 4H), 6.63 (q, 1H), 6.43 (m, 1H), 4.72 (t, 0.5H), 4.63 (t, 0.5H), 4.53 (m, 1H), 4.42 (q, 1H), 3.78 (m, 1H), 3.68 (s, 1.5H), 3.62 (d, 1.5H), 3.00 (m, 2H), 1.90–1.05 (m, 4H), 1.48 (d, 3H), 1.42 (s, 9H).

¹³C-nmr (CDCl₃): δ=174.2, 173.9, 173.1, 172.8, 156.7, 156.6, 146.8, 146.7, 133.4, 133.3, 131.2, 131.1, 121.9, 121.8, 115.5, 115.1, 114.0, 113.8, 79.7, 79.6, 60.9, 55.2, 55.1, 53.0, 52.9, 52.4, 52.1, 40.6, 40.5, 32.3, 32.2, 30.1, 28.9, 22.8, 21.6, 19.9, 14.7.

Example 20

Synthesis of N-[N-benzothiazol-6-yl)-D,L-alanyl]-(S)-2-aminohexanoic acid methyl ester Step A: Synthesis of N-[N-benzothiazol-6-yl)-D,L-alanine A solution of 1 gram of 6-aminobenzothiazole (Lancaster) in 60 mL of dichloromethane was treated with 0.63 grams of pyridine and then 2.1 grams of trifluoroacetic acid anhydride at room temperature. The reaction was stirred for 3 hours during which time the initially warm reaction mixture cooled to room temperature. The mixture was washed with a 5% aqueous citric acid solution, dried with MgSO₄ and the solvents removed to provide a quantitative yield of 6-aminobenzotriazole trifluoroacetamide as a cream colored solid that was used immediately in the following reaction.

A 300 mg portion of 6-aminobenzotriazole trifluoroacetamide was dissolved in 35 mL of THF and added to 1.2 eq. of KH at room temperature. The solution was refluxed for 5 hours, cooled and a crystal of 18-crown-6 (Aldrich) was added along with 331 mg of ethyl 2-bromopropionate (Aldrich) and the resulting mixture was refluxed for 36 hours. The reaction mixture was cooled, the solvents removed under reduced pressure and the residue dissolved in ethyl acetate. The organics were washed with water. The aqueous layer pH was adjusted to pH 5 and extracted with ethyl acetate. The organics were combined, dried with MgSO₄ and the solvents removed. The crude material was purified by preparative tlc using dichloromethane/methanol (94:4) to give N-(benzothiazol-6-yl)-D,L-alanine ethyl ester (Rf=0.5). This material was treated with methanol and 5 eq. of potassium carbonate at reflux, and then cooled and the solvents removed. The residue was taken up in water and ethyl acetate. The aqueous layer was adjusted to pH 2 and extracted with ethyl acetate. The ethyl acetate extracts were dried and the solvents removed to provide N-(benzothiazol-6-yl)-D,L-alanine.

Step B: Synthesis of N-[N-benzothiazol-6-yl)-D,L-alanyl]-(S)-2-aminohexanoic acid methyl ester Following General Procedure D (using DMF as the reaction solvent, ethyl acetate for extraction and without the 1N HCl wash) and using L-norleucine methyl ester hydrochloride (Sigma) and N-(benzothiazol-6-yl)-D,L-alanine (from Step A above), the title compound was prepared. The reaction was monitored by tlc (Rf=0.28 in 1:1 EtOAc:Hexanes) and the product was purified by flash chromatography using 1:1 EtOAc:Hexanes as the eluent.

NMR data was as follows:

¹H-nmr (CDCl₃) δ=8.74 (s, 1H), 7.91 (s, 1, J=8.8 Hz), 7.15 (m, 1H), 7.06 (d, 0.5H, J=2.3 Hz), 7.00 (d, 0.5H, J=2.3

Hz), 6.87 (m, 1H), 4.58 (m, 1H), 4.20 (bs, 2H), 3.87 (m, 1H), 3.70 (s, 1.5H), 3.59 (s, 1.5H), 1.30 (m, 10H), 0.84 (t, 1.5H, J=6.9 Hz), 0.60 (t, 1.5H, J=6.9H).

$^{13}$C-nmr (CDCl$_3$): δ=174.3, 174.0, 173.4, 173.0, 151.1, 151.0, 147.2, 145.5, 145.3, 136.2, 136.1, 124.4, 124.2, 116.1, 115.9, 104.6, 103.9, 56.2, 55.69, 53.0, 52.9, 52.5, 52.2, 32.42, 32.36, 28.0, 27.7, 22.8, 22.6, 20.3, 20.1, 14.4, 14.2.

$C_{17}H_{23}N_3O_3S2$ (MW=349.46); mass spectroscopy (MH$^+$) 350.

Example 21

Synthesis of N-[N-(3,4-dichlorophenyl)-D,L-alanyl]-L-lysine methyl ester

Following General Procedure F and using N-[N-(3,4-dichlorophenyl)-D,L-alanyl]-Nε-BOC-L-lysine methyl ester (from Example 19 above), the title compound was prepared as an oil. The reaction product was purified by silica gel chromatography using 89:10:1 CH$_2$Cl$_2$:MeOH:NH$_4$H.

NMR data was as follows:

$^1$H-nmr (CDCl$_3$—2 diastereomers): δ=7.21 (d, 1H), 7.09 (bd, 1H), 6.68 (q, 1H), 6.46 (m, 1H), 4.56 (m, 1H), 4.22 (bs, 1H), 3.78 (m, 1H), 3.70 (s, 1.5H), 3.67 (s, 1.5H), 2.66 (t, 1H), 2.54 (t, 1H), 1.80 (m, 1H), 1.62 (m, 1H), 1.51 (d, 1.5H), 1.50 (d, 1.5H), 1.32 (m, 2H), 1.11 (m, 1H).

$^{13}$C-nmr (CDCl$_3$—2 diastereomers): δ=174.8, 174.3, 173.1, 172.8, 171.8, 146.9, 146.7, 133.3, 133.1, 131.2, 131.1, 121.7, 121.5, 115.2, 1115.1, 113.9, 113.8, 60.9, 55.0, 54.9, 53.1, 53.0, 52.5, 52.3, 32.1, 32.09, 32.05, 31.8, 23.1, 22.9, 21.6, 19.9, 19.8, and 14.7.

$C_{16}H_{23}N_3O_3Cl_2$ (MW=376.28).

Example 22

Synthesis of N-[N-(3,4-dichlorophenyl)-D,L-alanyl]-L-tyrosine methyl ester

Following General Procedure D and using L-tyrosine methyl ester (Sigma) and N-(3,4-dichlorophenyl)-D,L-alanine (from Example A above), the title compound was prepared as a mixture of stereoisomers about alanine. The reaction was monitored by tlc (Rf=0.29 in 10% MeOH/CH$_2$Cl$_2$) and purification was by flash chromatography (10% methanol/methylene chloride).

NMR data was as follows:

$^1$H-nmr (CDCl$_3$) δ=7.22–7.50 (m, 7H), 6.36 (dd, 0.5H), 6.28 (dd, 0.5H), 4.83 (m 1H), 4.04 (dd, 1H), 3.73 (s, 1.5H), 3.70 (m, 1H), 3.68 (s, 1.5H), 3.14 (dd, 0.5H), 2.97 (m, 1.5H), 1.43 (d, 1.5H), 1.35 (d, 1.5H).

$^{13}$C-nmr (CDCl$_3$): δ=174.20, 174.08, 172.75, 172.26, 156.10, 155.99, 146.45, 146.32, 133.50, 133.38, 131.39, 131.26, 130.81, 130.67, 127.43, 127.00, 122.41, 122.22, 116.15, 116.12, 115.68, 115.39, 113.94, 113.46, 55.47, 55.08, 53.54, 53.18, 37.62, 37.44, 19.91, 19.87.

$C_{19}H_{20}N_2O_4Cl_2$ (MW=411.28).

Example 23

Synthesis of N-[N-(3,5-dichlorophenyl)-D,L-alanyl]-L-alanine methyl ester

Following General Procedure D and using N-(3,5-dichlorophenyl)-D,L-alanine (from Example B above) and L-alanine methyl ester hydrochloride (Sigma), the title compound was prepared as a oil. The reaction product was purified by silica gel chromatography using 50% ethyl acetate/hexane.

NMR data was as follows:

$^1$H-nmr (CDCl$_3$): δ=1.3–1.55 (three sets of doublets at 1.34, 1.39 and 1.48, all J=7, total 6H), 3.7–3.9 (m with singlets at 3.67 and 3.72, 4H), 4.3–4.4 (m, 1H), 4.5–4.65 (m, 1H), 6.4–6.6 (m, 2H), 6.73 (s, 1H), 6.95–7.1 (m, 1H).

$^{13}$C-nmr (CDCl$_3$): δ=15.52, 15.59, 16.75, 16.87, 45.29, 45.39, 50.02, 51.89, 51.999 108.9, 109.2, 109.5, 116.14, 116.19, 132.96, 133.96, 133.05, 145.67, 145.76, 170.13, 170.32, 170.40, 170.63.

$C_{13}H_{16}N_2O_3Cl_2$ (MW=319.19); mass spectroscopy (MH$^+$) 319.

Example 24

Synthesis of N-[N-(3,5-dichlorophenyl)-L-alanyl]-(S)-2-aminopentanoic acid methyl ester Following General Procedure D and using N-(3,5-dichlorophenyl)-D,L-alanine (from Example B above) and L-norvaline methyl ester hydrochloride (Sennchem), the title compound was prepared. The reaction product was purified by silica gel chromatography using 50% ethyl acetate/hexane.

NMR data was as follows:

$^1$H-nmr (CDCl$_3$): δ=0.92 (t, J=7, 3H), 1.2–1.4 (m, 2H), 1.50 (d, J=7, 3H), 1.5–1.7 (m, 1H), 1.75–1.9 (m, 1H), 3.69 (s, 3H), 3.75–3.9 (m, 1H), 4.2 (bs, 1H), 4.5–4.65 (m, 1H), 6.5 (bs, 2H), 6.73 (s, 1H), 6.85 (bs, 1H).

$^{13}$C-nmr (CDCl$_3$): δ=14.2, 19.25, 20.13, 34.8, 52.4, 53.0, 55.2, 112.7, 119.5, 136.1, 148.7, 173.0, 173.5.

$C_{15}H_{20}N_2O_3Cl_2$ (MW=347.24); mass spectroscopy (MH$^+$) 346.

Example 25

Synthesis of N-[N-(3,5-dichlorophenyl)-L-alanyl]-L-phenylalanine methyl ester Following General Procedure D and using N-(3,5-dichlorophenyl)-D,L-alanine and L-phenylalanine methyl ester hydrochloride (Sigma), the title compound was prepared. The reaction product was purified by silica gel chromatography using 50% ethyl acetate/hexane.

NMR data was as follows:

$^1$H-nmr (CDCl$_3$): δ=1.40 (d, J=7, 3H), 3.10 (dd, J=7,14, 1H), 3.23 (dd, J=5,14, 1H), 3.74 (s, 3H), 3.75–3.9 (m, 1H), 4.0 (bs, 1H), 4.8–4.95 (m, 1H), 6.45 (bs, 2H), 6.73 (s, 2H), 7.0–7.2 (m, 2H), 7.2–7.3 (m, 5H).

$^{13}$C-nmr (CDCl$_3$): δ=19.4, 37.5, 52.4, 52.7, 54.5, 112.0, 118.9, 127.1, 128.5, 129.1, 135.5, 135.6, 148.0, 171.4, 172.6.

$C_{19}H_{20}N_2O_3Cl_2$ (MW=395.29); mass spectroscopy (MH$^+$) 394.

Example 26

Synthesis of N-[N-(3,4-dichlorophenyl)-D,L-alanyl]-L-aspartic acid β-(methyl ester) α-methyl ester Following General Procedure D (without the 1N HCl wash) and using L-aspartic acid β-(methyl ester) α-methyl ester (Sigma) and N-(3,4-dichlorophenyl)-D,L-alanine (from Example A above), the title compound was prepared as a solid (mp=113.5–118° C.). The reaction was monitored by tlc (Rf=0.29 in 1:1 EtOAc:Hexanes) and the product was purified by flash chromatography using 1:1 EtOAc:Hexanes as the eluent.

NMR data was as follows:

$^1$H-nmr (CDCl$_3$) δ=7.47 (bd, 1H), 7.20 (m, 1H), 6.69 (d, 0.5H), 6.60 (d, 0.5H), 6.44 (m, 1H), 4.83 (m, 1H), 4.25 (bs, 0.5H), 4.18 (bs, 0.5H), 3.79 (m, 1H), 3.72 (s, 1.5H), 3.67 (s, 1.5H), 3.65 (s, 1.5H), 3.48 (s, 1.5H), 3.00 (m, 1H), 2.79 (m, 1H), 1.50 (m, 3H).

$^{13}$C-nmr (CDCl$_3$): δ=174.0, 173.6, 172.0, 171.7, 171.4, 171.3, 146.6, 146.4, 133.43, 133.37, 131.22, 131.20, 122.2, 122.0, 115.5, 115.0, 114.1, 113.6, 55.4, 55.2, 53.46, 53.44, 52.7, 52.5, 48.8, 48.7, 36.4, 36.3, 19.9, 19.7.

$C_{15}H_{18}N_2O_5Cl_2$ (MW=377.23); mass spectroscopy (MH$^+$) 377.

Example 27

Synthesis of N-[N-(3,4-dichlorophenyl)-D,L-alanyl]-(N'-1-benzyl)-L-histidine methyl ester Following General Procedure D (without the 1N HCl wash) and using 1-benzyl-L-histidine methyl ester hydrochloride (Sigma) and N-(3,4-dichlorophenyl)-D,L-alanine (from Example A above), the title compound was prepared as a solid (mp=49–51° C.). The reaction was monitored by tlc (Rf=0.21 in 5% methanol/methylene chloride) and the product was purified by flash chromatography using 5% methanol:methylene chloride as the eluent.

NMR data was as follows:

$^1$H-nmr (CDCl$_3$) δ=8.22 (d, 0.5H), 7.88 (d, 0.5H), 7.29 (m, 3H), 7.08 (m, 4H), 6.65 (d, 0.5H), 6.44 (m, 2.5H), 4.90 (s, 1H), 4.86 (s, 1H), 4.62 (m, 1H), 4.47 (m, 1H), 3.72 (m, 1H), 3.61 (s, 1.5H), 3.47 (s, 1.5H), 2.95 (m, 2H), 1.42 (d, 3H).

$^{13}$C-nmr (CDCl$_3$): δ=174.0, 173.9, 172.4, 172.0, 146.9, 138.1, 137.9, 137.6, 136.7, 136.5, 133.1, 133.0, 131.0, 130.9, 129.6, 129.5, 128.84, 128.79, 127.74, 127.71, 121.1, 121.0, 117.3, 115.3, 115.1, 113.9, 113.6, 54.9, 54.8, 53.2, 52.9, 52.8, 52.7, 51.3, 51.2, 30.2, 29.8, 19.8.

$C_{23}H_{24}N_4O_3Cl_2$ (MW=475.38); mass spectroscopy (M$^+$) 475.

Example 28

Synthesis of N-[N-(3,4-dichlorophenyl)-D,L-alanyl]-L-glutamic acid β-(tert-butyl ester) α-methyl ester Following General Procedure D (without the 1N HCl wash) and using L-glutamic acid β-(tert-butyl ester) α-methyl ester hydrochloride (Bachem) and N-(3,4-dichlorophenyl)-D,L-alanine (from Example A above), the title compound was prepared as an oil. The reaction was monitored by tlc (Rf=0.52 and 0.59 in 1:1 EtOAc:Hexanes) and the product was purified by flash chromatography using 1:1 EtOAc: Hexanes as the eluent.

NMR data was as follows:

$^1$H-nmr (CDCl$_3$) δ=7.25 (m, 2H), 6.69 (m, 1H), 6.45 (m, 1H), 4.54 (m, 1H), 3.78 (m, 1H), 3.70 (s, 1.5H), 3.65 (s, 1.5H), 2.10 (m, 4H), 1.49 (d, 3H), 1.40 (s, 9H).

$^{13}$C-nmr(CDCl$_3$): δ=174.2, 173.9, 172.8, 172.7, 172.5, 172.3, 146.6, 146.5, 133.5, 133.3, 131.3, 131.2, 122.16, 122.14, 115.7, 115.4, 114.0, 113.6, 81.6, 81.5, 55.4, 55.2, 53.1, 53.0, 52.3, 51.9, 32.0, 31.7, 28.6, 27.6, 27.3, 20.0, 19.8.

$C_{19}H_{26}N_2O_5Cl_2$ (MW=433.34); mass spectroscopy (MH$^+$) 432.

Example 29

Synthesis of N-[N-(3,4-dichlorophenyl)-D,L-alanyl]-L-glutamic acid α-methyl ester The tert-butyl ester group of N-[N-(3,4-dichlorophenyl)alanyl]glutamic acid β-(tert-butyl ester) α-methyl ester (from Example 28 above) was removed via General Procedure F (the NaHCO$_3$ wash was omitted and the product was recovered from the ethyl acetate phase) to provide for the title compound as a solid (mp=42–45° C.). The reaction was monitored by tlc (Rf=0.42 and 0.50 in 10% methanol/methylene chloride).

NMR data was as follows:

$^1$H-nmr (CDCl$_3$) δ=7.57 (bs, 1H), 7.25 (d, 1H), 6.75 (d, 1H), 6.51 (m, 1H), 4.67 (m, 1H), 3.91 (m, 1H), 3.76 (s, 1.5H), 3.69 (s, 1.5H), 2.50–2.15 (m, 3H), 2.10–1.85 (m, 1H), 1.51 (bs, 3H).

$^{13}$C-nmr (CDCl$_3$): δ=177.98, 177.73, 175.17, 174.94, 172.64, 172.26, 146.60, 146.45, 133.52, 133.33, 131.41, 131.27, 122.32, 122.28, 115.68, 155.47, 113.98, 113.59, 55.37, 55.17, 53.35, 53.29, 52.20, 51.85, 30.68, 30.26, 227.29, 27.18, 19.86, 19.77.

$C_{15}H_{18}N_2O_5Cl_2$ (MW=377.23).

Example 30

Synthesis of N-[N-(3,4-dichlorophenyl)-L-alanyl]-L-leucine amide

Following General Procedure D and using L-leucinamide hydrochloride (Sigma) and N-(3,4-dichlorophenyl)-D,L-alanine (from Example A above), the title compound was prepared. This compound was then purified by column chromatography, eluted first with 1:1 EtOAc/hexane, then with 5% MeOH) in methylene chloride.

NMR data was as follows:

$^1$H-nmr (CDCl$_3$) δ=7.32 (d, 8.6, 1H), 7.17 (d, 8.7, 1H), 6.66 (d, 2.7, 1H), 6.54 (s, 1H), 6.41 (dd, 2.7, 8.7, 1H), 6.13 (s, 1H), 4.48 (m, 1H), 4.33 (d, 5.3, 1H), 3.83 (quint, 6.9, 1H), 1.58 (m, 3H), 1.44 (d, 7.0, 3H), 0.89 (d, 6.0, 3H), 0.85 (d, 5.9, 3H).

$^{13}$C-nmr (CDCl$_3$): δ=174.5, 173.9, 146.0, 132.8, 130.7, 121.5, 114.7, 113.3, 54.3, 51.1, 40.8, 24.8, 22.9, 21.7, 19.2.

$C_{15}H_{21}N_3O_2Cl_2$ (MW=346.26); mass spectroscopy (MH$^+$) 346.

Example 31

Synthesis of N-[N-(3,4-dichlorophenyl)-D,L-alanyl]-(3,5-diiodo)-L-tyrosine methyl ester Following General Procedure D and using 3,5-diiodo-L-tyrosine methyl ester hydrochloride (Bachem) and N-(3,4-dichlorophenyl)-D,L-alanine (from Example A above), the title compound was prepared as a mixture of stereoisomers about alanine. The reaction was monitored by tlc (Rf=0.29 in 10% MeOH/CH$_2$Cl$_2$) and purification was by flash chromatography (10% methanol/methylene chloride).

NMR data was as follows:

$^1$H-nmr (CDCl$_3$—partially pure diastereomer A) δ=7.37 (s, 2H), 7.19 (d, 1H), 6.99 (bd, 1H), 6.65 (d, 1H), 6.40 (m, 1H), 5.78 (s, 1H), 4.73 (q, 1H), 3.72 (m, 1H), 0.70 (s, 3H).

$^{13}$C-nmr (CDCl$_3$—two diastereomers): δ=173.86, 171.87, 171.41, 171.37, 170.90, 153.48, 150.74, 146.37, 146.30, 141.01, 140.09, 138.39, 133.50, 133.45, 132.14, 131.62, 131.34, 131.28, 122.80, 122.62, 121.82, 115.89, 115.78, 115.72, 115.47, 114.54, 113.79, 113.21, 82.92, 77.08, 61.01, 55.69, 53.32, 53.28, 53.18, 53.14, 52.97, 52.90, 52.76, 36.37, 36.15, 21.67, 20.20, 20.11, 19.76, 14.79.

$C_{19}H_{18}N_2O_4Cl_2I_2$ (MW=663.08); mass spectroscopy (MH$^+$)=663.

Example 32

Synthesis of N-[N-(3,4-dichlorophenyl)-D,L-alanyl]-(3-iodo)-L-tyrosine methyl ester Following General Procedure D and using 3-iodo-L-tyrosine methyl ester hydrochloride (prepared following General Procedure K and using 3-iodo-L-tyrosine (Aldrich)) and N-(3,4-dichlorophenyl)-D,L-alanine (from Example A above), the title compound was prepared as a mixture of stereoisomers about alanine. The reaction was monitored by tlc (Rf=0.29 in 10% MeOH/CH$_2$Cl$_2$) and purification was by flash chromatography (10% methanol/methylene chloride).

NMR data was as follows:

$^1$H-nmr (CDCl$_3$) δ=7.37–7.20 (m, 3H), 6.97–6.60 (m, 3H), 6.42 (dd, 1.5H), 6.32 (dd, 1.5H), 5.52 (bs, 0.5H), 5.43 (bs, 0.5H), 4.80 (m, 1H), 3.94 (dd, 1H), 3.73 (s, 1.5H), 3.70 (s, 1.5H), 3.12 (dd, 0.5H), 2.94 (m, 1.5H), 1.48 (d, 1.5H), 1.43 (d, 1.5H).

$^{13}$C-nmr (CDCl$_3$): δ=173.56, 171.80, 171.33, 154.52, 154.47, 145.69, 139.15, 138.74, 132.88, 132.71, 130.83, 130.61, 130.40, 130.26, 129.14, 128.81, 121.76, 121.73, 115.04, 114.97, 114.86, 113.20, 112.71, 84.96, 84.68, 54.85, 54.65, 52.78, 52.60, 52.57, 52.51, 36.29, 36.08, 19.40, 19.27.

$C_{19}H_{19}N_2O_4Cl_2I$ (MW=537.18); mass spectroscopy (MH$^+$)=538.

Example 33

Following the General Procedures and Examples described herein, the following compound could be prepared:

N-[N-(4-chlorophenyl)-D,L-alanyl]-L-phenylalanine methyl ester

Example 34

Synthesis of N-[N-(3,4-dichlorophenyl)glycyl]-(S)-2-aminopentanoic acid methyl ester Following General Procedure D and using N-(3,4-dichlorophenyl)glycine (from Example I above) and L-norvaline methyl ester hydrochloride (Sennchem), the title compound was prepared. The reaction was monitored by tlc (Rf=0.32 in 50% ethyl acetate/hexanes) and purification was by silica gel chromatography using ethyl acetate/hexanes as the eluent.

NMR data was as follows:

$^1$H-nmr (CDCl$_3$) δ=7.21 (d, J=8.7, 1H), 6.94 (d, J=7.8, 1H), 6.68 (d, J=2.6, 1H), 6.4 (m, 1H), 4.6 (m, 2H), 3.79 (d, J=2.6, 2H), 3.7 (s, 3H), 1.7 (m, 2H), 1.2 (m, 2H), 0.88 (t, J=7.3, 7.3, 3H).

$^{13}$C-nmr (CDCl$_3$): δ=173.3, 170.2, 147.2, 133.6, 131.3, 122.2, 115.0, 113.6, 53.0, 52.3, 48.8, 34.8, 19.2, 14.1.

$C_{14}H_{18}N_2O_3Cl_2$ (MW=333.22); mass spectroscopy (MH$^+$)=334.

Example 35

Synthesis of N-[N-(3,4-dichlorophenyl)-D,L-alanyl]-Nε-(hexanoyl)-L-lysine methyl ester Following General Procedure D and using N-[N-(3,4-dichlorophenyl)-D,L-alanyl]-L-lysine methyl ester (from Example 21 above) and hexanoic acid (Aldrich), the title compound was prepared. The reaction was monitored by tlc (Rf=0.38 in 60% CH$_2$CH$_2$/10% hexanes/27% EtOAc/3% MeOH) and purification was by flash chromatography using 60% CH$_2$CH$_2$/10% hexanes/27% EtOAc/3% MeOH as the eluent.

NMR data was as follows:

$^1$H-nmr (CDCl$_3$) δ=7.70 (d), 7.25 (m), 7.15 (m), 6.68 (m), 6.42 (m), 5.95 (bs), 5.79 (bs), 4.70 (bs), 4.50 (m), 3.80 (m), 3.78 (s), 3.72 (s), 3.45 (m), 3.20 (m), 3.05 (m), 2.12 (m), 1.98 (m), 1.80 (m), 1.60 (m), 1.45 (m), 1.30 (m), 1.10 (m).

$^{13}$C-nmr (CDCl$_3$): δ=175.6, 174.4, 174.0, 173.9, 173.7, 173.1, 156.6, 146.9, 146.8, 133.5, 133.2, 131.2, 131.1, 121.7, 115.4, 115, 23, 115.1, 114.0, 113.9, 79.6, 55.1, 54.9, 54.8, 53.0, 52.9, 52.4, 52.0, 42.6, 40.9, 39.4, 37.1, 32.1, 31.7, 30.3, 29.4, 28.9,.28.5, 26.9, 25.9, 25.9, 23.0, 19.9, 19.7.

$C_{22}H_{33}N_3O_4Cl_2$ (MW=474.43); mass spectroscopy (MH$^+$)=NA.

Example 36

Synthesis of N-[N-(3,4-dichlorophenyl)-D,L-alanyl]-L-phenylalanine amide

Following General Procedure D and using phenylalanine amide (Bachem) and N-(3,4-dichlorophenyl)-D,L-alanine (from Example A above), the title compound was prepared as a solid (mp=177–179° C.). This compound was then purified by trituration with chloroform.

NMR data was as follows:

$^1$H-nmr (DMSO-d$_6$) δ=8.0–8.2 (d, 1H), 7.45 (m, 1H), 7.05–7.30 (m, 7H), 7.65–7.72 (m, 1H), 6.24–6.51 (m, 2H), 4.45 (m, 1H), 3.82 (m, 1H), 2.95 (m, 1H), 2.78 (m, 1H), 1.05–1.25 (m, 3H).

$^{13}$C-nmr (CDCl$_3$): δ=173.0, 172.9, 172.8, 172.7, 147.9, 137.7, 131.1, 130.3, 129.21, 129.15, 128.0, 127.9, 126.21, 126.19, 116.8, 113.5, 113.0, 112.6, 53.4, 53.3, 52.0, 51.8, 37.92, 37.86, 18.9, 18.6.

$C_{18}H_{19}N_3O_2Cl_2$ (MW=380.28); mass spectroscopy (MH$^+$) 380.

Example 37

Synthesis of N-[N-(3,4-dichlorophenyl)-D,L-alanyl]-(S)-2-aminohexan-(N-methyl)-amide Following General Procedure D and using L-norleucine N-methyl amide (prepared by coupling BOC-L-norleucine (Bachem) with methylamine (Aldrich) using General Procedure E, followed by removal of the BOC group using General Procedure F) and N-(3,4-dichlorophenyl)-D,L-alanine, the tile compound was prepared. This compound was then purified by washing with aqueous potassium carbonate.

NMR data was as follows:

$^1$H-nmr (CD$_3$OD) δ=6.99 (t, 1H), 6.48 (d, 10.8, 1H), 6.32 (d, 8.7, 1H), 4.09 (m, 1H), 3.68 (q, 7.0, 0.5H), 3.59 (q, 7.1, 0.5H), 2.50 (s, 1.5H), 2.47 (s, 1.5H), 1.28–1.60 (m, 2H), 1.23 (t, 6.5, 3H), 0.80–1.20 (m, 4H), 0.68 (t, 6.7, 1.5H), 0.59 (t, 7.1, 1.5H).

$^{13}$C-nmr (CD$_3$OD): δ=176.6 (overlapping), 174.54, 174.51, 148.8, 148.5, 133.6, 133.5, 131.7, 131.6, 121.0, 120.8, 115.2, 115.1, 114.5, 114.2, 55.3, 54.7, 54.3, 54.1, 33.3 (overlapping), 29.0, 28.8, 26.3, 26.2, 23.4, 23.3, 19.0 (overlapping), 14.3, 14.2.

$C_{16}H_{23}N_3O_2Cl_2$ (MW=360.29); mass spectroscopy (MH$^+$) 360.

Examples 38 and 39

Synthesis of N-[N-(3,4-dichlorophenyl)-D,L-alanyl]-β-cyclohexylalanine methyl ester Following General Procedure D and using β-cyclohexylalanine methyl ester (prepared from β-cyclohexylalanine (Bachem) using General Procedure K) and N-(3,4-dichlorophenyl)-D,L-alanine, the title compound, as a mixture of diastereomers about alanine, was prepared as an oil. The reaction was monitored by tlc (Rf=0.27 (second isomer) and 0.30 (first isomer) in 35% EtOAc/hexanes) and purification was by flash chromatography (35% EtOAc/hexanes).

NMR data was as follows (First Isomer—Example 38):

$^1$H-nmr (CD$_3$OD) δ=7.21 (d, 1H), 6.81 (bd, 1H), 6.70 (d, 1H), 6.46 (dd, 1H), 4.62 (m, 1H), 4.19 (d, 1H), 3.77 (m, 1H), 3.65 (s, 3H), 1.65–0.90 (m, 10H), 1.50 (d, 3H).

C$^{13}$C-nmr (CD$_3$OD): δ=173.78, 173.48, 146.62, 133.45, 131.26, 122.51, 115.84, 114.17, 55.64, 52.91, 50.47, 40.18, 34.81, 34.04, 32.88, 26.86, 26.71, 26.55, 20.13.

NMR data was as follows (Second Isomer—Example 39):

$^1$H-nmr (CD$_3$OD) δ=7.23 (d, 1H), 6.83 (bd, 1H), 6.67 (d, 1H), 6.45 (dd, 1H), 4.63 (m, 1H), 4.10 (d, 1H), 3.69 (m, 1H), 3.72 (s, 3H), 1.65–0.90 (m, 10H), 1.51(d, 3H).

$^{13}$C-nmr (CD$_3$OD): δ=173.98, 173.56, 146.38, 133.65, 131.34, 122.49, 115.35, 113.78, 55.39, 52.95, 50.21, 40.26, 34.61, 34.10, 32.68, 26.82, 26.64, 26.41, 19.98.

$C_{19}H_{26}N_2O_3Cl_2$ (MW=401.34); mass spectroscopy (MH$^+$) 401.

Example 40

Synthesis of N-[N-(3,4-dichlorophenyl)-L-alanyl]-(S)-2-aminohexanamide

Following General Procedure D and using L-norleucine amide (prepared from BOC-L-norleucine amide (from Example F above) using General Procedure F) and N-(3,4-dichlorophenyl)-D,L-alanine, the title compound was prepared as a solid (mp=156–161° C.).

NMR data was as follows:

$^1$H-nmr (CD$_3$OD) δ=6.49 (m, 1H), 6.32 (m, 1H), 1.14 (m, 1H), 3.54–3.71 (m, 1H), 0.80–1.62 (m, 9H), 0.68 (m, 1.5H), 0.58 (m, 1.5H).

$^{13}$C-nmr (CD$_3$OD): δ=176.63, 176.56, 148.8, 148.5, 133.6, 133.5, 131.7, 131.6, 120.8, 115.2, 115.1, 114.4, 114.2, 55.3, 54.7, 53.9, 53.7, 33.4, 33.3, 29.0, 28.6, 23.4, 23.3, 19.03, 18.99, 14.3, 14.2.

$C_{15}H_{21}N_3O_2Cl_2$ (MW=346.26); mass spectroscopy (MH$^+$) 346.

Example 41

Synthesis of N-[N-(3,4-dichlorophenyl)-D,L-alanyl]-(S)-2-aminohexan-(N,N-dimethyl)-amide Following General Procedure D and using L-norleucine N,N-dimethyl amide (prepared by coupling BOC-L-norleucine (Bachem) with dimethylamine (Aldrich) using General Procedure E, followed by removal of the BOC group using General Procedure F) and N-(3,4-dichlorophenyl)-D,L-alanine, the title compound was prepared as a solid (mp=137–160° C.). The reaction was monitored by tlc (0.20 and 0.24 (5% MeOH in CH$_2$Cl$_2$) and purification of this compound was by precipitation from water.

NMR data was as follows:

$^1$H-nmr (CDCl$_3$) δ=0.77 (m, 3H), 1.11 (m, 1H), 1.24 (m, 3H), 1.47 (m, 3H), 1.40–1.80 (m, 2H), 2.92 and 2.94 (two s, 3H), 3.07 (s, 3H), 3.84 (m, 1H), 4.32 (d, J=5.3 Hz, 1H), 4.90 (m, 1H), 6.44 (m, 1H), 6.65 (s, 1H), 7.17 (m, 1H), 7.35 (m, 1H).

$^{13}$C-nmr (CDCl$_3$): δ=13.8, 13.9, 19.3, 19.4, 22.38, 22.45, 27.06, 27.14, 32.3, 32.5, 35.7 (possibly overlapping), 37.0, 37.1, 48.6, 48.8, 54.3, 54.5, 113.1, 113.5, 114.4, 114.7, 121.1, 121.3, 130.6 (overlapping), 132.7, 132.9, 146.0, 146.2, 171.4, 171.5, 172.6, 172.9.

$C_{17}H_{25}N_3O_2Cl_2$ (MW=374.31); mass spectroscopy (MH$^+$) 374.

Example 42

Synthesis of N-[N-(3,4-dichlorophenyl)-D,L-alanyl]-L-methionine methyl ester

Following General Procedure D and using L-methionine methyl ester hydrochloride (Sigma) and N-(3,4-dichlorophenyl)-D,L-alanine (from Example A above), the title compound was prepared as a mixture of diastereomers. The reaction was monitored by tlc (Rf=0.35 in 43% EtOAc/hexanes) and purification of this compound was by flash chromatography with 43% EtOAc/hexanes.

NMR data was as follows:

$^1$H-nmr (CDCl$_3$): δ=7.21 (d, 2H), 6.68 (m, 1H), 6.43 (m, 1H), 4.68 (m, 1H), 4.21 (dd, 1H), 3.79 (m, 1H), 3.73 (s, 1.5H), 3.68 (s, 1.5H), 2.46 (m, 1H), 2.31 (t, 1H), 2.23–1.88 (m, 2H), 2.06 (s, 1.5H), 1.93 (s, 1.5H), 1.50 (d, 3H).

$^{13}$C-nmr (CDCl$_3$): δ=174.09, 173.81, 172.73, 172.38, 146.60, 146.47, 133.43, 131.37, 131.27, 122.36, 122.33, 115.65, 115.31, 114.05, 113.65, 55.48, 55.32, 53.19, 53.16, 51.99, 51.68, 31.74, 31.64, 30.62, 30.42, 20.10, 19.92, 16.08, 15.91.

$C_{15}H_{20}N_2O_2Cl_2S$ (MW=379.31); mass spectroscopy (MH$^+$) 379.

Example 43

Synthesis of N-[N-(3,5-dichlorophenyl)-D,L-alanyl]-(S)-2-aminohexan-(N,N-dimethyl)-amide Following General Procedure E and using L-norleucine N,N-dimethyl amide (prepared by coupling BOC-L-norleucine (Bachem) with dimethylamine (Aldrich) using General Procedure E, followed by removal of the BOC group using General Procedure F) and N-(3,5-dichlorophenyl)-D,L-alanine (from Example B above), the title compound was prepared. The reaction was monitored by tlc (Rf=0.25–0.30 in 3% methanol/dichloromethane) and purification of this compound was by chromatography with 3% methanol/dichloromethane.

NMR data was as follows:

$^1$H-nmr (CDCl$_3$): δ=0.8–0.95 (overlapping t, 3H), 1.2–1.8 (m containing overlapping d at 1.45 and 1.48, 9H), 2.95 (s, 3H), 3.10 (s, 3H), 3.8–3.9 (m, 1H), 4.3–4.4 (m, 1H), 4.8–4.95 (m, 1H), 6.45 (s, 2H), 6.6–6.7 (m, 1H).

$C_{17}H_{25}N_3O_2Cl_2$ (MW=374.31).

Example 44

Synthesis of N-[N-(3,5-dichlorophenyl)-D,L-alanyl]-(S)-2-aminohexanamide

Following General Procedure D and using N-(3,5-dichlorophenyl)-D,L-alanine (from Example B above) and L-norleucine amide (from Example F above), the title compound was prepared. The reaction was monitored by tlc (Rf=0.15 in 3% methanol/dichloromethane) and purification of this compound was by thin layer chromatography with 3% methanol/dichloromethane.

NMR data was as follows:

$^1$H-nmr (CD$_3$OD): δ=0.9 (t, J=7, 3H), 1.2–1.4 (m, 2H), 1.45 (d, J=7, 3H), 1.5–1.7 (m, 1H), 1.75–1.9 (m, 1H), 3.9–4.0 (m, 1H), 4.1–4.3 (m, 1H), 4.3–4.4 (m, 1H), 6.5 (bs, 2H), 6.6 (bs, 1H).

C$_{15}$H$_{21}$N$_3$O$_2$Cl$_2$ (MW=346.26).

Example 45

Synthesis of N-[N-(3,5-dichlorophenyl)-D,L-alanyl]-(S)-2-aminohexan-(N-methyl)-amide Following General Procedure D and using N-(3,5-dichlorophenyl)-D,L-alanine and L-norleucine N-methyl amide (prepared by coupling BOC-L-norleucine (Bachem) with methylamine (Aldrich) using General Procedure E, followed by removal of the BOC group using General Procedure F), the title compound was prepared. The reaction was monitored by tlc (Rf=0.25 in 3% methanol/dichloromethane) and purification of this compound was by thin layer chromatography with 3% methanol/dichloromethane.

NMR data was as follows:

$^1$H-nmr (CD$_3$OD): δ=0.9 (t, J=7, 3H), 1.2–1.4 (m, 2H), 1.45 (d, J=7, 3H), 1.5–1.7 (m, 1H), 1.75–1.9 (m, 1H), 2.6–2.7 (m with s at 2.7, 4H), 3.8–4.0 (m, 1H), 4.1–4.3 (m, 2H), 6.5 (bs, 2H), 6.6 (bs, 1H)

C$_{16}$H$_{23}$N$_3$O$_2$Cl$_2$ (MW=360.29).

Example 46

Synthesis of N-[N-(3,4-dichlorophenyl)-D,L-alanyl]-L-histidine methyl ester

Following General Procedure D (without the 1N HCl wash) and using L-histidine methyl ester dihydrochloride (Sigma) and N-(3,4-dichlorophenyl)-D,L-alanine, the title compound was prepared as a solid (mp=55–60° C.). The reaction was monitored by tlc (Rf=0.52 in 10% methanol/methylene chloride) and purification of this compound was by flash chromatography with 50% EtOAc/hexanes.

NMR data was as follows:

$^1$H-nmr (CDCl$_3$): δ=8.14 (bd, J=7.02 Hz, 0.5H), 7.79 (bd, 7.57 Hz, 0.5H), 7.33 (s, 1H), 7.14 (m, 1H), 6.73 (s, 0.5H), 6.69 (s, 0.5H), 6.59 (m, 1H), 6.47 (m, 0.5H), 6.37 (m, 0.5H), 4.74 (m, 1H), 4.33 (m, 1H), 3.79 (m, 1H), 3.69 (s, 1.5H), 3.62 (s, 1.5H), 3.05 (m, 2H), 1.47 (d, J=7.02 Hz, 3H).

$^{13}$C-nmr (CDCl$_3$): δ=174.35, 174.15, 172.45, 172.08, 146.80, 146.67, 135.48, 135.07, 134.65, 133.24, 133.12, 131.13, 131.04, 121.54, 121.49, 115.96, 115.78, 115.38, 115.05, 113.90, 113.72, 61.04, 54.98, 53.11, 52.97, 52.71, 29.71, 19.43, 21.68, 19.86, 19.84, 14.77.

C$_{16}$H$_{18}$N$_4$O$_3$Cl$_2$ (MW=385.25); mass spectroscopy (MH$^+$) 385.

Example 47

Synthesis of N-[N-(quinolin-3-yl)-D,L-alanyl]-(S)-2-aminohexanoic acid methyl ester Using General Procedure G, followed by hydrolysis set forth in General Procedure C, N-(quinolin-3-yl)-D,L-alanine was prepared. This compound was then coupled to L-norleucine methyl ester hydrochloride (Sigma) using General Procedure D to provide for the title compound as an oil. The latter reaction was monitored by tlc (Rf=0.76 in 10% methanol/methylene chloride and 0.07 in 1:1 EtOAc:Hexanes and the product was purified by flash chromatography using 10% methanol/methylene chloride as the eluent.

NMR data was as follows:

$^1$H-nmr (CDCl$_3$): δ=8.53 (t, J=2.8 Hz, 1H), 7.95 (m, 1H), 7.63 (m, 1H), 7.46 (m, 2H), 7.20 (m, 1H), 7.10 (d, J=2.75 Hz, 0.5H), 7.01 (d, J=2.75 Hz, 0.5H), 4.60 (m, 2H), 3.94 (m, 1H), 3.71 (s, 1.5H), 3.54 (s, 1.5H), 1.90–0.80 (m, 12H).

$^{13}$C-nmr (CDCl$_3$): δ=173.82, 173.50 ,173.40, 172.96, 143.65, 143.60, 143.39, 143.32, 140.34, 140.26, 129.57, 129.49, 127.869 127.78, 126.94, 126.78, 126.54, 113.39, 112.65, 55.69, 55.46, 53.00, 52.86, 52.62, 52.28, 32.42, 32.35, 28.03, 27.79, 22.78, 22.62, 20.22, 20.01, 14.41, 14.12.

C$_{19}$H$_{25}$N$_3$O$_3$ (MW=343.43).

Example 48

Synthesis of

N-[-N-(benzothiazol-2-yl)-L-alanyl](S)-2-aminohexanoic acid methyl ester

Following General Procedure B and using 2-chlorobenzothiazole (Aldrich) and L-alanine (Aldrich), N-(benzothiazol-2-yl)-L-alanine was prepared. This compound was then coupled to L-norleucine methyl ester hydrochloride (Sigma) using General Procedure D (without the 1N HCl wash) to provide for the title compound as a solid (mp=99–120° C.). The latter reaction was monitored by tlc (Rf=0.42 in 1:1 EtOAc:Hexanes) and the product was purified by preparative plate chromatography using 1:1 EtOAc:Hexanes and 5:95 MeOH:dichloromethane as the eluent.

NMR data was as follows:

$^1$H-nmr (CDCl$_3$): δ=7.66–7.03 (m, 6H), 4.69 (m, 1H), 4.58 (m, 1H), 3.72 (s, 1.9H), 3.61 (s, 1.1H), 1.91–1.50 (m, 5H), 1.32–1.08 (m, 4H), 0.87–0.65 (m, 3H).

$^{13}$C-nmr (CDCl$_3$): δ=175.8, 170.3, 166.8, 160.2, 152.3, 148.4, 132.1, 131.1, 126.8, 126.5, 124.5, 122.6, 122.0, 121.4, 120.9, 119.4, 54.3, 54.2, 53.0, 52.9, 3.5, 28.1, 28.0, 23.9, 22.9, 19.0, 18.8, 14.2.

C$_{17}$H$_{23}$N$_3$O$_3$S (MW=349.46); mass spectroscopy (MH$^+$ 350).

Example 49

Synthesis of N-[N-(3,5-difluorophenyl)-D,L-alanyl]-L-alanine methyl ester

Following General Procedure E and using L-alanine methyl ester hydrochloride (Sigma) and N-(3,5-difluorophenyl)-D,L-alanine (from Example C above), the title compound was prepared as a solid (mp=93–95° C.). The reaction was monitored by tlc (Rf=0.4 in 3% methanol/methylene chloride) and purification of this compound was by flash chromatography with 3% methanol/methylene chloride.

NMR data was as follows:

$^1$H-nmr (CDCl$_3$): δ=6.9 (q), 6.25 (t), 6.10 (q), 5.3 (s), 4.6 (m), 4.25 (m), 33.7–3.8 (m), 1.8 (s), 1.5 (d), 1.4 (q), 1.25 (s).

$^{13}$C-nmr (CDCl$_3$): δ=173.78, 173.51, 173.44, 173.27, 166.24, 166.09, 163.04, 162.83, 149.41, 149.37, 97.47, 97.34, 97.20, 97.09, 96.82, 95.08, 95.03, 94.73, 94.69, 94.39, 94.34, 55.27, 55.22, 53.10, 53.02, 48.46, 48.35, 19.99, 19.87, 18.72, 18.66.

$C_{13}H_{16}N_2O_3F_2$ (MW=286.3); mass spectroscopy (MH$^+$) 287.

Example 50

Synthesis of N-[N-(3,5-difluorophenyl)-D,L-alanyl]-(S)-2-aminohexanoic acid methyl ester Following General Procedure E and using L-norleucine methyl ester hydrochloride (Sigma) and N-(3,5-difluorophenyl)-D,L-alanine, the title compound was prepared as a solid (mp=93–95° C.). The reaction was monitored by tlc (Rf=0.6 in 3% methanol/methylene chloride) and purification of this compound was by flash chromatography with 3% methanol/methylene chloride.

NMR data was as follows:

$^1$H-nmr (CDCl$_3$): δ=6.95 (d), 6.85 (d), 6.25 (t), 6.15 (t), 4.6 (m), 4.3 (m), 3.8 (m), 3.75 (s), 3.70 (s), 1.8 (m), 1.65 (m), 1.55 (d), 1.3 (m), 1.1 (m), 0.85 (t), 0.80 (t).

$^{13}$C-nmr (CDCl$_3$): δ=173.64, 173.42, 173.35, 173.04, 149.38, 149.23, 97.52, 97.21, 97.14, 96.83, 95.10, 95.05, 94.75, 94.70, 94.41, 77.61, 77.19, 55.34, 55.25, 52.97, 52.87, 52.58, 52.25, 32.41, 27.96, 27.74, 22.79, 22.68, 20.05, 19.87, 14.39, 14.25.

$C_{16}H_{22}N_2O_3F_2$ (MW=328.3); mass spectroscopy (MH$^+$) 329.

Example 51

Synthesis of N-[N-(3,4-dichlorophenyl)-L-alanyl]-(S)-2-aminohexanamide

Following General Procedure D (using DMF as the solvent and ethyl acetate for extraction, and without the 1N HCl wash) and using L-norleucine amide (prepared from BOC-L-norleucine amide (from Example F above) using General Procedure F) and N-(3,4-dichlorophenyl)-L-alanine prepared from 3,4-dichloroaniline (Aldrich) and isobutyl R-(+)-lactate (Aldrich) using General Procedure J, followed by hydrolysis using General Procedure C), the title compound was prepared as a solid (mp=184–186° C.). The reaction was monitored by tlc (Rf=0.48 in 12% methanol/methylene chloride) and purification of this compound was by preparative plate chromatography using 12% methanol/methylene chloride as eluent.

NMR data was as follows:

$^1$H-nmr (CD$_3$OD): δ=6.97 (d, J=8.79 Hz, 1H), 6.51 (d, J=2.68 Hz, 1H), 6.32 (dd, J=8.73 Hz, J=2.68 Hz, 1H), 4.14 (m, 1H), 3.67 (q, J=6.96 Hz, 1H), 1.40 (m, 10H), 0.70 (m, 3H)

$^{13}$C-nmr (CDCl$_3$): δ=177.19, 177.11, 149.41, 134.05, 132.13, 121.38, 115.82, 114.96, 55.26, 54.48, 33.92, 29.54, 23.95, 19.58, 14.83.

$C_{15}H_{21}N_3O_2Cl_2$ (MW=346.26); mass spectroscopy (MH$^+$) 346.

Example 52

Synthesis of N-[N-(3,4-dichlorophenyl)-D,L-alanyl]-(S)-2-aminohexan(N-benzyl)-amide Following General Procedure H above and using N-[N-(3,4-dichlorophenyl)-D,L-alanyl]-(S)-2-aminohexanoic acid methyl ester (from Example 15 above) and benzylamine (Aldrich), the title compound was prepared as a solid (mp=141–146° C.). The reaction was monitored by tlc on silica gel (Rf=0.32 in 5% methanol/methylene chloride) and purification was by preparative plate chromatography (silica gel using 5% methanol/methylene chloride as eluent).

NMR data was as follows:

$^1$H-nmr (CDCl$_3$): δ=7.6 (m, 2H), 7.2 (m, 6H), 6.6 (m, 1H), 6.3 (m, 1H), 4.47 (m, 4H), 3.75 (m, 1H), 1.28 (m, 12H).

$^{13}$C-nmr (CDCl$_3$): δ=174.56, 174.50, 172.39, 172.32, 146.78, 146.65, 138.38, 133.439 133.38, 131.22, 129.21, 128.06, 121.98, 121.72, 121.66, 115.21, 115.08, 113.73, 113.55, 54.94, 54.36, 53.60, 53.22, 43.95, 33.10, 32.98, 28.24, 27.95, 22.96, 22.90, 19.78, 19.70, 14.49, 14.41.

$C_{22}H_{27}Cl_2N_3O_2$ (MW=436.39); mass spectroscopy (MH$^+$) 436.

Example 53

Synthesis of N-[N-(3,4-dichlorophenyl)-D,L-alanyl]-(S)-2-amino-2-phenylethanol

Following General Procedure E and using N-(3,4-dichlorophenyl)-D,L-alanine (from Example A above) and (S)-(+)-2-phenylglycinol (Aldrich), the title compound was prepared as a solid (mp=66–70° C.). The reaction was monitored by tlc on silica gel (Rf=0.25 in 5% methanol/methylene chloride) and purification was by flash column chromatography (silica gel using 5% methanol/methylene chloride as eluent).

NMR data was as follows:

$^1$H-nmr (CDCl$_3$): δ=7.4–7.1 (m, 6H), 6.75 (d, J=3 Hz, 1H), 6.5–6.4 (m, 1H), 5 (m, 1H), 4.2–4.0 (m, J=4 Hz, 1H), 3.8 (2H), 1.7 (s, 1H), 1.55 (m, 3H).

$^{13}$C-nmr (CDCl$_3$): δ=174, 146, 139, 134, 131.8, 129.5, 128.5, 127, 123, 116, 114, 112, 67, 56.5, 55.5, 20.

$C_{16}H_{18}Cl_2N_2O_2$ (MW=341); mass spectroscopy (MH$^+$) 342.

Examples 54 and 55

Synthesis of N-[N-(3,5-dichlorophenyl)-D,L-phenylglycyl]-L-alanine methyl ester

Following General Procedure E and using N-(3,5-dichlorophenyl)-D,L-phenylglycine (from Example J above) and L-alanine methyl ester hydrochloride (Sigma), the title compound was prepared. The reaction was monitored by tlc (Rf=0.95 in 3% methanol/methylene chloride) and purification of this compound was by recrystallization from EtOAc, hexane and ether. Two partially separated diastereomeric mixtures were obtained.

NMR data was as follows:

$^1$H-nmr (CDCl$_3$—75% isomer A/25% isomer B): δ=7.45–7.35 (m, 5H) 6.7 (m, 2H), 6.47 (m, 2H), 5.1–5.0 (dd, J=3 Hz, 1H), 4.75 (d, J=3.5 Hz, 1H), 4.65–4.5 (m, 7.2 Hz 1H), 3.75–3.68 (2 s in a ratio of 3:1, 3H), 1.43–1.3 (2 d in a ratio of 3:1, J=7.2 Hz, 3H).

$^{13}$C-nmr (CDCl$_3$—75% isomer A/25% isomer B): δ=173.27, 170.24, 148.61, 138.23, 136.07, 136.00, 130.11, 129.60, 129.58, 127.83, 127.69, 119.10, 112.68, 112.56, 78.03, 63.27, 53.20, 48.94, 18.85.

$^1$H-nmr (CDCl$_3$—25% isomer A/75% isomer B): δ=7.45–7.35 (m, 5H), 6.7 (m, 2H), 6.47(m, 2H), 5.1–5.0 (2xd, J=3 Hz, 4.75 (d, J=3.5 Hz, 1H), 4.65–4.5 (m, J=7.2 Hz, 1H), 3.75–3.68 (2 s in a ratio of 1:3, 3H), 1.43–1.3 (2 d in a ratio of 1:3, J=7.2 Hz, 3H).

$^{13}$C-nmr (CDCl$_3$—25% isomer A/75% isomer B): δ=173.27, 170.24, 148.61, 138.23, 136.07, 136.00, 130.11, 129.60, 129.58, 127.83, 127.69, 119.10, 112.68, 112.56, 78.03, 63.27, 53.20, 48.94, 18.85.

C$_{18}$H$_{18}$N$_2$O$_3$Cl$_2$ (MW=381.26); mass spectroscopy (MH$^+$) 381.

Example 56

Synthesis of N-[N-(3,4-dichlorophenyl)-D,L-alanyl]-(S)-2-aminohexanol

Following General Procedure I above and using N-[N-(3,4-dichlorophenyl)-D,L-alanyl]-(S)-2-aminohexanoic acid methyl ester (from Example 15 above), the title compound was prepared as an oil. The reaction was monitored by tlc on silica gel (Rf=0.16 and 0.17 in 5% methanol/methylene chloride) and purification was by preparative plate chromatography (silica gel using 5% methanol/methylene chloride as eluent).

NMR data was as follows:

$^1$H-nmr (CD$_3$OD): δ=7.20 (d, 1H), 6.79 (m, 1H), 6.68 (dd, 1H) 6.43 (d, 1H), 4.42 (bd, 0.6H), 4.30 (bd, 0.4H), 3.89 (m, 1H), 3.75 (m, 1H), 3.70–3.40 (m, 2H), 1.60–0.95 (m, 9H), 0.90–0.70 (m, 3H)

$^{13}$C-nmr (CD$_3$OD): δ=174.42, 174.17, 146.06, 145.96, 132.89, 132.85, 130.74, 130.69, 121.64, 121.49, 114.98, 114.70, 113.14, 113.08, 65.42, 65.11, 55.00, 54.76, 51.69, 51.48, 30.67, 30.59, 28.16, 28.00, 22.48, 22.36, 19.44, 13.92, 13.82.

C$_{15}$H$_{22}$Cl$_2$N$_2$O$_2$ (MW=333.26); mass spectroscopy (MH$^+$) 333.

Example 57

Synthesis of N-[-N-(3,5-dichlorophenyl)-D,L-alanyl]-(S)-2-amino-2-phenylethanol

Following General Procedure E and using N-(3,5-dichlorophenyl)-D,L-alanine (from Example B above) and (S)-(+)-2-phenylglycinol (Aldrich), the title compound could be prepared.

Example 58

Synthesis of N-[N-(3,5-dichlorophenyl)-L-alanyl]-L-phenylglycine tert-butyl ester Following General Procedure D (without the 1N HCl wash) and using N-(3,5-dichlorophenyl)-L-alanine (prepared from 3,5-dichloroaniline (Aldrich) and isobutyl R-(+)-lactate (Aldrich) using General Procedure J, followed by hydrolysis using General Procedure C) and L-phenylglycine tert-butyl ester hydrochloride (Bachem), the title compound was prepared. The reaction was monitored by tlc (Rf=0.39 in 25% EtOAc/Hexanes) and purification of this compound was by preparative plate chromatography using 25% EtOAc/Hexanes.

NMR data was as follows:

$^1$H-nmr (CDCl$_3$): δ=7.55 (d, J=7.39 Hz, 1H), 7.30 (s, 5H), 6.73 (t, J=1.68 Hz, 1H), 6.46 (d, J=1.71 Hz, 2H), 5.45 (d, J=7.45 Hz, 1H), 4.47 (d, J=5.19 Hz, 1H), 3.82 (m, 1H), 1.40 (d, J=6.96 Hz, 3H), 1.34 (s, 9H).

$^{13}$C-nmr (CDCl$_3$): δ=173.23, 169.92, 148.93, 137.43, 136.07, 129.40, 128.85, 127.40, 119.04, 112.48, 83.42, 57.37, 54.70, 28.29, 19.79.

C$_{21}$H$_{24}$N$_2$O$_3$Cl$_2$ (MW=423.34); mass spectroscopy (MH$^+$) 423.

Example 59

Synthesis of N-[N-(3,5-di-(trifluoromethyl)phenyl)-L-alanyl]-L-phenylglycine tert-butyl ester Following General Procedure D and using N-[3,5-di-(trifluoromethyl)phenyl]-L-alanine (from Example G above) and L-phenylglycine tert-butyl ester hydrochloride (Bachem), the title compound was prepared. The reaction was monitored by tlc (Rf=0.46 in 25% EtOAc/Hexanes).

NMR data was as follows:

$^1$H-nmr (CDCl$_3$): δ=7.39 (d, J=7.39 Hz, 1H), 7.29 (s, 5H), 6.96 (s, 2H), 5.45 (d, J=7.51 Hz, 1H), 4.69 (d, J=5.31 Hz, 1H), 3.95 (m, 1H), 1.48 (d, J=6.96 Hz, 3H), 1.33 (s, 9H).

$^{13}$C-nmr (CDCl$_3$): δ=172.7, 169.9, 147.9, 137.3, 132.8, 132.4, 129.42, 129.34, 129.31, 128.9, 127.4, 127.2, 127, 122.1, 113.50, 113.47, 112.34, 112.29, 112.24, 83.5, 57.3, 54.6, 28.34, 28.30, 28.2, 19.8.

C$_{23}$H$_{24}$N$_2$O$_3$F$_6$ (MW=490.45).

Example 60

Synthesis of N-[N-(3,5-dimethoxyphenyl)-D,L-alanyl]-(S)-2-aminohexanoic acid methyl ester Following General Procedure E (washing with dilute HCl and extracting with EtOAc) and using N-(3,5-dimethoxyphenyl)-D,L-alanine (from Example H above) and L-norleucine methyl ester hydrochloride (Sigma), the title compound was prepared as a light yellow oil. The reaction was monitored by tlc (Rf=0.3 in 30% EtOAc/Hexanes).

NMR data was as follows:

$^1$H-nmr (CDCl$_3$): δ=0.6–0.9 (two triplets at 0.72 and 0.82, J=7 Hz 3H), 1.0–1.9 (m, 9H), 3.6–3.7 (four singlets at 3.60, 3.65, 3.66 and 3.67, 10H), 3.7–3.8 (m, 1H), 4.6–4.7 (m, 1H), 5.7–5.95 (m, 3H), 7.1–7.3 (m, 1H).

$^{13}$C-nmr (CDCl$_3$): δ=14.21, 14.35, 19.8, 20.0, 22.69, 22.74, 27.8, 28.0, 32.20, 32.45, 52.18, 52.57, 52,65, 52.78, 55.31, 55.52, 55.59, 55.63, 91.6, 91.8, 92.86, 93.24, 149.02, 149.27, 162.11, 162.18, 173.02, 173.44, 174.47, 174.82.

C$_{18}$H$_{28}$N$_2$O$_5$ (MW=352.43).

Example 61

Cellular Screen for the Detection of Inhibitors of β-Amyloid Production

Numerous compounds of formula I above were assayed for their ability to inhibit β-amyloid production in a cell line possessing the Swedish mutation. This screening assay employed cells (K293=human kidney cell line) which were stably transfected with the gene for amyloid precursor protein 751 (APP751) containing the double mutation Lys$_{651}$Met$_{652}$ to Asn$_{651}$Leu$_{652}$ (APP751 numbering) in the manner described in International Patent Application Publication No. 94/10569[8] and Citron et al.[11]. This mutation is commonly called the Swedish mutation and the cells, designated as "293 751 SWE", were plated in Corning 96-well plates at 1.5–2.5×10$^4$ cells per well in Dulbecco's minimal essential media (Sigma, St. Louis, Mo.) plus 10% fetal bovine serum. Cell number is important in order to achieve β-amyloid ELISA results within the linear range of the assay (~0.2 to 2.5 ng per mL).

Following overnight incubation at 37° C. in an incubator equilibrated with 10% carbon dioxide, media were removed and replaced with 200 μL of a compound of formula I (drug)

containing media per well for a two hour pretreatment period and cells were incubated as above. Drug stocks were prepared in 100% DMSO such that at the final drug concentration used in the treatment, the concentration of dimethyl sulfoxide did not exceed 0.5% and, in fact, usually equaled 0.1%.

At the end of the pretreatment period, the media were again removed and replaced with fresh drug containing media as above and cells were incubated for an additional two hours. After treatment, plates were centrifuged in a Beckman GPR at 1200 rpm for five minutes at room temperature to pellet cellular debris from the conditioned media. From each well, 100 μL of conditioned media or appropriate dilutions thereof were transferred into an ELISA plate precoated with antibody 266 [P. Seubert, Nature (1992) 359:325–327] against amino acids 13–28 of β-amyloid peptide as described in International Patent Application Publication No. 94/10569[8] and stored at 4° C. overnight. An ELISA assay employing labelled antibody 6C6 [P. Seubert, Nature (1992) 359:325–327] against amino acids 1–16 of β-amyloid peptide was run the next day to measure the amount of β-amyloid peptide produced.

Cytotoxic effects of the compounds were measured by a modification of the method of Hansen, et al.[12]. To the cells remaining in the tissue culture plate was added 25 μL of a 3-(4,5-dimethylthiazol-2-yl)-2,5-diphenyltetrazolium bromide (MTT) (Sigma, St. Louis, Mo.) stock solution (5 mg/mL) to a final concentration of 1 mg/mL. Cells were incubated at 37° C. for one hour, and cellular activity was stopped by the addition of an equal volume of MTT lysis buffer (20% w/v sodium dodecylsulfate in 50% dimethylformamide, pH 4.7). Complete extraction was achieved by overnight shaking at room temperature. The difference in the $OD_{562nm}$ and the $OD_{650nm}$ was measured in a Molecular Device's $UV_{max}$ microplate reader as an indicator of the cellular viability.

The results of the β-amyloid peptide ELISA were fit to a standard curve and expressed as ng/mL β-amyloid peptide. In order to normalize for cytotoxicity, these results were divided by the MTT results and expressed as a percentage of the results from a drug free control. All results are the mean and standard deviation of at least six replicate assays.

The test compounds were assayed for β-amyloid peptide production inhibition activity in cells using this assay. The results of this assay demonstrate that, each of the compounds of Examples 1–60 inhibit the β-amyloid peptide production by at least 30% as compared to control.

Example 62

In Vivo Suppression of β-Amyloid Release and/or Synthesis

This example illustrates how the compounds of this invention could be tested for in vivo suppression of β-amyloid release and/or synthesis. For these experiments, 3 to 4 month old PDAPP mice are used [Games et al., (1995) Nature 373:523–527]. Depending upon which compound is being tested, the compound is usually formulated at either 5 or 10 mg/mL. Because of the low solubility factors of the compounds, they may be formulated with various vehicles, such as corn oil (Safeway, South San Francisco, Calif.); 10% ethanol in corn oil; 2-hydroxypropyl-β-cyclodextrin (Research Biochemicals International, Natick Mass.); and carboxymethylcellulose (Sigma Chemical Co., St. Louis Mo.).

The mice are dosed subcutaneously with a 26 gauge needle and 3 hours later the animals are euthanized via $CO_2$ narcosis and blood is taken by cardiac puncture using a 1 cc 25G ⅝" tuberculin syringe/needle coated with solution of 0.5M EDTA, pH 8.0. The blood is placed in a Becton-Dickinson vacutainer tube containing EDTA and spun down for 15 minutes at 1500× gravity at 5° C. The brains of the mice are then removed and the cortex and hippocampus are dissected out and placed on ice.

1. Brain Assay

To prepare hippocampal and cortical tissue for enzyme-linked immunosorbent assays (ELISAs) each brain region is homogenized in 10 volumes of ice cold guanidine buffer (5.0M guanidine-HCl, 50 mM Tris-HCl, pH 8.0) using a Kontes motorized pestle (Fisher, Pittsburgh Pa.). The homogenates are gently rocked on a rotating platform for three to four hours at room temperature and stored at −20° C. prior to quantitation of β-amyloid.

The brain homogenates are diluted 1:10 with ice-cold casein buffer [0.25% casein, phosphate buffered saline (PBS), 0.05% sodium azide, 20 μg/mL aprotinin, 5 mM EDTA, pH 8.0, 10 μg/mL leupeptin], thereby reducing the final concentration of guanidine to 0.5M, before centrifugation at 16,00× gravity for 20 minutes at 4° C. The β-amyloid standards (1–40 or 1–42 amino acids) were prepared such that the final composition equaled 0.5M guanidine in the presence of 0.1% bovine serum albumin (BSA).

The total β-amyloid sandwich ELISA, quantitating both β-amyloid (aa 1–40) and β-amyloid (aa 1–42) consists of two monoclonal antibodies (mAb) to β-amyloid. The capture antibody, 266 [P. Seubert, Nature (1992) 359:325–327], is specific to amino acids 13–28 of β-amyloid. The antibody 3D6 [Johnson-Wood et al., PNAS USA (1997) 94:1550–1555], which is specific to amino acids 1–5 of β-amyloid, is biotinylated and served as the reporter antibody in the assay. The 3D6 biotinylation procedure employs the manufacturer's (Pierce, Rockford Ill.) protocol for NHS-biotin labeling of immunoglobulins except that 100 mM sodium bicarbonate, pH 8.5 buffer is used. The 3D6 antibody does not recognize secreted amyloid precursor protein (APP) or full-length APP but detects only β-amyloid species with an amino terminal aspartic acid. The assay has a lower limit of sensitivity of ~50 pg/mL (11 pM) and shows no cross-reactivity to the endogenous murine β-amyloid peptide at concentrations up to 1 ng/mL.

The configuration of the sandwich ELISA quantitating the level of β-amyloid (aa 1–42) employs the mAb 21F12 [Johnson-Wood et al., PNAS USA (1997) 94:1550–1555] (which recognizes amino acids 33–42 of β-amyloid) as the capture antibody. Biotinylated 3D6 is also the reporter antibody in this assay which has a lower limit of sensitivity of ~125 pg/mL (28 pM)

The 266 and 21F12 capture mAbs are coated at 10 μg/mL into 96 well immunoassay plates (Costar, Cambidge Mass.) overnight at room temperature The plates are then aspirated and blocked with 0.25% human serum albumin in PBS buffer for at least 1 hour at room temperature, then stored desiccated at 4° C. until use. The plates are rehydrated with wash buffer (Tris-buffered saline, 0.05% Tween 20) prior to use. The samples and standards are added to the plates and incubated overnight at 4° C. The plates are washed ≧3 times with wash buffer between each step of the assay. The biotinylated 3D6, diluted to 0.5 μg/mL in casein incubation buffer (0.25% casein, PBS, 0.05% Tween 20, pH 7.4) is incubated in the well for 1 hour at room temperature. Avidin-HRP (Vector, Burlingame Calif.) diluted 1:4000 in casein incubation buffer is added to the wells for 1 hour at room temperature. The colorimetric substrate, Slow TMB-ELISA (Pierce, Cambridge Mass.), is added and allowed to react for 15 minutes, after which the enzymatic reaction is stopped with addition of 2N $H_2SO_4$. Reaction product is quantified using a Molecular Devices Vmax (Molecular Devices, Menlo Park Calif.) measuring the difference in absorbance at 450 nm and 650 nm.

2. Blood Assay

The EDTA plasma is diluted 1:1 in specimen diluent (0.2 g/L sodium phosphate.$H_2O$ (monobasic), 2.16 g/L sodium phosphate.$7H_2O$ (dibasic), 0.5 g/L thimerosal, 8.5 g/L sodium chloride, 0.5 mL Triton X-405, 6.0 g/L globulin-free bovine serum albumin; and water). The samples and standards in specimen diluent are assayed using the total β-amyloid assay (266 capture/3D6 reporter) described above for the brain assay except the specimen diluent was used instead of the casein diluents described.

From the foregoing description, various modifications and changes in the composition and method will occur to those skilled in the art. All such modifications coming within the scope of the appended claims are intended to be included therein.

(b) a substituted phenyl group of formula II:

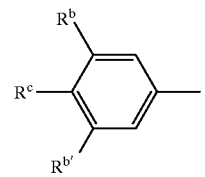

wherein $R^c$ is selected from the group consisting of acyl, alkyl, alkoxy, alkylalkoxy, azido, cyano, halo, hydrogen, nitro, trihalomethyl, thioalkoxy, and wherein $R^b$ and $R^c$ are fused to form a heteroaryl or heterocyclic ring with the phenyl ring, $R^b$ and $R^{b'}$ are independently selected from the group consisting of hydrogen, halo, nitro, cyano, trihalomethyl, alkoxy, and thioalkoxy with the proviso

---

---

What is claimed is:

1. A method for inhibiting β-amyloid peptide release and/or its synthesis in a cell which method comprises administering to such a cell an amount of a compound or a mixture of compounds effective in inhibiting the cellular release and/or synthesis of β-amyloid peptide wherein said compounds are represented by formula I:

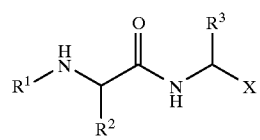

wherein:
   $R^1$ is selected from the group consisting of
      (a) phenyl, that when $R^c$ is hydrogen, then $R^b$ and $R^{b'}$ are either both hydrogen or both substituents other than hydrogen,
   (c) 2-naphthyl,
   (d) 2-naphthyl substituted at the 4, 5, 6, 7 and/or 8 positions with 1 to 5 substituents selected from the group consisting of alkyl, alkoxy, halo, cyano, nitro, trihalomethyl, thioalkoxy, aryl, and heteroaryl,
   (e) heteroaryl, and
   (f) substituted heteroaryl containing 1 to 3 substituents selected from the group consisting of alkyl, alkoxy, aryl, aryloxy, cyano, halo, nitro, heteroaryl, thioalkoxy and thioaryloxy provided that said substituents are not ortho to the heteroaryl attachment to the —NH group;

$R^2$ is selected from the group consisting of hydrogen, alkyl of from 1 to 4 carbon atoms, alkylalkoxy of from 1 to 4 carbon atoms, alkylthioalkoxy of from 1 to 4 carbon atoms, aryl, heteroaryl, substituted aryl and substituted heteroaryl provided that the substituents are not ortho to the attachment of the aryl or heteroaryl atom to the carbon atom;

$R^3$ is selected from the group consisting of alkyl, alkenyl, alkynyl, aryl, cycloalkyl, cycloalkenyl, heteroaryl, substituted alkyl, substituted alkenyl, substituted alkynyl, and heterocyclic;

X is —C(O)Y where Y is selected from the group consisting of
(a) alkyl,
(b) substituted alkyl with the proviso that the substitution on said substituted alkyl does not include α-haloalkyl, α-diazoalkyl or α-OC(O)alkyl groups,
(c) alkoxy or thioalkoxy,
(d) substituted alkoxy or substituted thioalkoxy,
(e) hydroxy,
(f) aryl,
(g) heteroaryl,
(h) heterocyclic,
(i) —NR'R" where R' and R" are independently selected from the group consisting of hydrogen, alkyl, substituted alkyl, cycloalkyl, aryl, heteroaryl, heterocyclic, and where R' and R" are joined to form a cyclic group having from 2 to 8 carbon atoms optionally containing 1 to 2 additional heteroatoms selected from the group consisting of oxygen, sulfur and nitrogen and optionally substituted with one or more alkyl or alkoxy groups, and when $R^3$ contains at least 3 carbon atoms, X can also be —$CR^4R^4Y'$ where each $R^4$ is independently selected from the group consisting of hydrogen, alkyl, cycloalkyl, aryl, heteroaryl and heterocyclic and Y' is selected from the group consisting of hydroxyl, amino, thiol, —$OC(O)R^5$, —$SSR^5$, —$SSC(O)R^5$ where $R^5$ is selected from the group consisting of alkyl, substituted alkyl, cycloalkyl, aryl, heteroaryl and heterocyclic, and with the proviso that when $R^1$ is 3,4-dichlorophenyl, $R^2$ is methyl, and $R^3$ is benzyl derived from D-phenylalanine, then X is not —$C(O)OCH_3$.

2. A method for preventing the onset of AD in a patient at risk for developing AD which method comprises administering to said patient a pharmaceutical composition comprising a pharmaceutically inert carrier and an effective amount of a compound or a mixture of compounds of formula I:

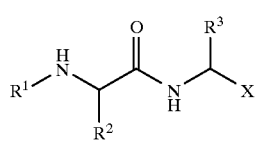

I wherein:

$R^1$ is selected from the group consisting of
(a) phenyl, (b) a substituted phenyl group of formula II:

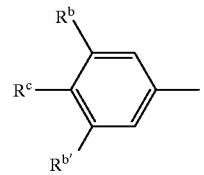

II wherein $R^c$ is selected from the group consisting of acyl, alkyl, alkoxy, alkylalkoxy, azido, cyano, halo, hydrogen, nitro, trihalomethyl, thioalkoxy, and wherein $R^b$ and $R^c$ are fused to form a heteroaryl or heterocyclic ring with the phenyl ring, $R^b$ and $R^{b'}$ are independently selected from the group consisting of hydrogen, halo, nitro, cyano, trihalomethyl, alkoxy, and thioalkoxy with the proviso that when $R^c$ is hydrogen, then $R^b$ and $R^{b'}$ are either both hydrogen or both substituents other than hydrogen, (c) 2-naphthyl,
(d) 2-naphthyl substituted at the 4, 5, 6, 7 and/or 8 positions with 1 to 5 substituents selected from the group consisting of alkyl, alkoxy, halo, cyano, nitro, trihalomethyl, thioalkoxy, aryl, and heteroaryl,
(e) heteroaryl, and
(f) substituted heteroaryl containing 1 to 3 substituents selected from the group consisting of alkyl, alkoxy, aryl, aryloxy, cyano, halo, nitro, heteroaryl, thioalkoxy and thioaryloxy provided that said substituents are not ortho to the heteroaryl attachment to the —NH group;

$R^2$ is selected from the group consisting of hydrogen, alkyl of from 1 to 4 carbon atoms, alkylalkoxy of from 1 to 4 carbon atoms, alkylthioalkoxy of from 1 to 4 carbon atoms, aryl, heteroaryl, substituted aryl and substituted heteroaryl provided that the substituents are not ortho to the attachment of the aryl or heteroaryl atom to the carbon atom;

$R^3$ is selected from the group consisting of alkyl, alkenyl, alkynyl, aryl, cycloalkyl, cycloalkenyl, heteroaryl, substituted alkyl, substituted alkenyl, substituted alkynyl, and heterocyclic;

X is —C(O)Y where Y is selected from the group consisting of
(a) alkyl,
(b) substituted alkyl with the proviso that the substitution on said substituted alkyl does not include α-haloalkyl, α-diazoalkyl or α-OC(O)alkyl groups,
(c) alkoxy or thioalkoxy,
(d) substituted alkoxy or substituted thioalkoxy,
(e) hydroxy,
(f) aryl,
(g) heteroaryl,
(h) heterocyclic,
(i) —NR'R" where R' and R" are independently selected from the group consisting of hydrogen, alkyl, substituted alkyl, cycloalkyl, aryl, heteroaryl, heterocyclic, and where R' and R" are joined to form a cyclic group having from 2 to 8 carbon atoms optionally containing 1 to 2 additional heteroatoms selected from the group consisting of oxygen, sulfur and nitrogen and optionally substituted with one or more alkyl or alkoxy groups, and when $R^3$ contains at least 3 carbon atoms, X can also be —$CR^4R^4Y'$ where each $R^4$ is independently selected from the group consisting of hydrogen, alkyl, cycloalkyl, aryl, heteroaryl and heterocyclic and Y' is selected from the group consisting of hydroxyl, amino, thiol, —OC(O)R$^5$, —SSR$^5$, —SSC(O)R$^5$ where R$^5$ is selected from the group consisting of alkyl, substituted alkyl, cycloalkyl, aryl, heteroaryl and heterocyclic, and with the proviso that when R$^1$ is 3,4-dichlorophenyl, R$^2$ is methyl, and R$^3$ is benzyl derived from D-phenylalanine, then X is not —C(O)OCH$_3$.

3. A method for treating a patient with AD in order to inhibit further deterioration in the condition of that patient which method comprises administering to said patient a pharmaceutical composition comprising a pharmaceutically inert carrier and an effective amount of a compound or a mixture of compounds of formula I:

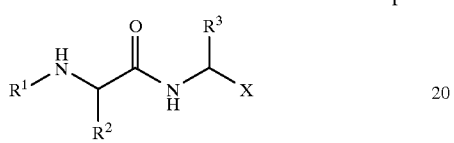

wherein:
R$^1$ is selected from the group consisting of
(a) phenyl,
(b) a substituted phenyl group of formula II:

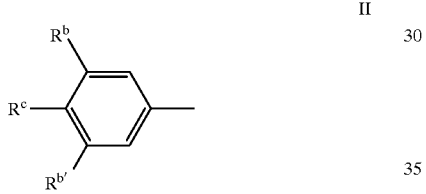

wherein R$^1$ is selected from the group consisting of acyl, alkyl, alkoxy, alkylalkoxy, azido, cyano, halo, hydrogen, nitro, trihalomethyl, thioalkoxy, and wherein R$^b$ and R$^c$ are fused to form a heteroaryl or heterocyclic ring with the phenyl ring, R$^b$ and R$^{b'}$ are independently selected from the group consisting of hydrogen, halo, nitro, cyano, trihalomethyl, alkoxy, and thioalkoxy with the proviso that when R$^c$ is hydrogen, then R$^b$ and R$^{b'}$ are either both hydrogen or both substituents other than hydrogen, (c) 2-naphthyl,
(d) 2-naphthyl substituted at the 4, 5, 6, 7 and/or 8 positions with 1 to 5 substituents selected from the group consisting of alkyl, alkoxy, halo, cyano, nitro, trihalomethyl, thioalkoxy, aryl, and heteroaryl,
(e) heteroaryl, and
(f) substituted heteroaryl containing 1 to 3 substituents selected from the group consisting of alkyl, alkoxy, aryl, aryloxy, cyano, halo, nitro, heteroaryl, thioalkoxy and thioaryloxy provided that said substituents are not ortho to the heteroaryl attachment to the —NH group;

R$^2$ is selected from the group consisting of hydrogen, alkyl of from 1 to 4 carbon atoms, alkylalkoxy of from 1 to 4 carbon atoms, alkylthioalkoxy of from 1 to 4 carbon atoms, aryl, heteroaryl, substituted aryl and substituted heteroaryl provided that the substituents are not ortho to the attachment of the aryl or heteroaryl atom to the carbon atom;

R$^3$ is selected from the group consisting of alkyl, alkenyl, alkynyl, aryl, cycloalkyl, cycloalkenyl, heteroaryl, substituted alkyl, substituted alkenyl, substituted alkynyl, and heterocyclic;

X is —C(O)Y where Y is selected from the group consisting of
(a) alkyl,
(b) substituted alkyl with the proviso that the substitution on said substituted alkyl does not include α-haloalkyl, α-diazoalkyl or α-OC(O)alkyl groups,
(c) alkoxy or thioalkoxy,
(d) substituted alkoxy or substituted thioalkoxy,
(e) hydroxy,
(f) aryl,
(g) heteroaryl,
(h) heterocyclic,
(i) -NR'R" where R' and R" are independently selected from the group consisting of hydrogen, alkyl, substituted alkyl, cycloalkyl, aryl, heteroaryl, heterocyclic, and where R' and R" are joined to form a cyclic group having from 2 to 8 carbon atoms optionally containing 1 to 2 additional heteroatoms selected from the group consisting of oxygen, sulfur and nitrogen and optionally substituted with one or more alkyl or alkoxy groups, and when R$^3$ contains at least 3 carbon atoms, X can also be —CR$^4$R$^4$Y' where each R$^4$ is independently selected from the group consisting of hydrogen, alkyl, cycloalkyl, aryl, heteroaryl and heterocyclic and Y' is selected from the group consisting of hydroxyl, amino, thiol, —C(O)R$^5$, —SSR$^5$, —SSC(O)R$^5$ where R$^5$ is selected from the group consisting of alkyl, substituted alkyl, cycloalkyl, aryl, heteroaryl and heterocyclic, and with the proviso that when R$^1$ is 3,4-dichlorophenyl, R$^2$ is methyl, and R$^3$ is benzyl derived from D-phenylalanine, then X is not —C(O)OCH$_3$.

4. The method according to claim 1, 2 or 3 wherein R$^1$ is phenyl, 2-naphthyl, quinolin-3-yl, benzothiazol-6-yl, and 5-indolyl.

5. The method according to claim 1, 2 or 3 wherein R$^1$ is a substituted phenyl group of the formula:

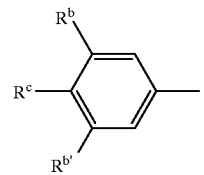

wherein R$^c$ is selected from the group consisting of acyl, alkyl, alkoxy, alkylalkoxy, azido, cyano, halo, hydrogen, nitro, trihalomethyl, thioalkoxy, and wherein R$^b$ and R$^c$ are fused to form a heteroaryl or heterocyclic ring with the phenyl ring, R$^b$ and R$^{b'}$ are independently selected from the group consisting of hydrogen, halo, nitro, cyano, trihalomethyl, alkoxy, and thioalkoxy with the proviso that when R$^c$ is hydrogen, then R$^b$ and R$^{b'}$ are either both hydrogen or both substituents other than hydrogen.

6. The method according to claim 1, 2 or 3 wherein R$^1$ is a substituted 2-naphthyl substituted at the 4, 5, 6, 7 and/or 8 positions with 1 to 5 substituents selected from the group consisting of alkyl, alkoxy, halo, cyano, nitro, trihalomethyl, thioalkoxy, aryl, and heteroaryl.

7. The method according to claim 1, 2 or 3 wherein $R^1$ is a substituted heteroaryl containing 1 to 3 substituents selected from the group consisting of alkyl, alkoxy, aryl, aryloxy, cyano, halo, nitro, heteroaryl, thioalkoxy, thioaryloxy provided that said substituents are not ortho to the heteroaryl attachment to the —NH group.

8. The method according to claim 5 wherein $R^1$ is a 4-substituted, a 3,5-disubstituted or 3,4-disubstituted phenyl.

9. The method according to claim 8 wherein $R^1$ is a 3,5-disubstituted phenyl.

10. The method according to claim 9 wherein the 3,5-disubstituted phenyl is selected from the group consisting of 3,5-dichlorophenyl, 3,5-difluorophenyl, 3,5-di(trifluoromethyl)phenyl and 3,5-dimethoxyphenyl.

11. The method according to claim 8 wherein $R^1$ is a 3,4-disubstituted phenyl.

12. The method according to claim 11 wherein the 3,4-disubstituted phenyl is selected from the group consisting of 3,4-dichlorophenyl, 3,4-difluorophenyl, 3-(trifluoromethyl)-4-chlorophenyl, 3-chloro-4-cyanophenyl, 3-chloro-4-iodophenyl and 3,4-methylenedioxyphenyl.

13. The method according to claim 8 wherein $R^1$ is a 4-substituted phenyl.

14. The method according to claim 13 wherein the 4-substituted phenyl is selected from the group consisting of 4-azidophenyl, 4-bromophenyl, 4-chlorophenyl; 4-cyanophenyl, 4-ethylphenyl, 4-fluorophenyl, 4-iodophenyl, 4-(phenylcarbonyl)phenyl, and 4-(1-ethoxy)ethylphenyl.

15. The method of claims 1, 2 or 3 wherein $R^1$ is 2-methylquinolin-6-yl.

16. The method according to claims 1, 2 or 3 wherein $R^2$ is selected from the group consisting of alkyl of from 1 to 4 carbon atoms, alkylalkoxy of from 1 to 4 carbon atoms, alkylthioalkoxy of from 1 to 4 carbon atoms and aryl.

17. The method according to claim 16 wherein $R^2$ is selected from the group consisting of methyl, ethyl, n-propyl, iso-propyl, n-butyl, so-butyl, —CH$_2$CH$_2$SCH$_3$ and phenyl.

18. The method according to claims 1, 2 or 3 wherein $R^3$ is an alkyl group.

19. The method according to claim 18 wherein the alkyl group is selected from the group consisting of methyl, ethyl, n-propyl, iso-propyl, n-butyl, iso-butyl and sec-butyl.

20. The method according to claims 1, 2 or 3 wherein $R^3$ is a substituted alkyl group.

21. The method according to claim 20 wherein the substituted alkyl group is selected from the group consisting of α-hydroxyethyl, —CH$_2$-cyclohexyl, benzyl, p-hydroxybenzyl, 3-iodo-4-hydroxybenzyl, 3,5-diiodo-4-hydroxybenzyl, —CH$_2$-indol-3-yl, —(CH$_2$)$_4$—NH-BOC, —(CH$_2$)$_4$—NH$_2$, —CH$_2$-(1-N-benzyl-imidazol-4-yl), —CH$_2$-imidazol-4-yl, —CH$_2$CH$_2$SCH$_3$, —(CH$_2$)$_4$NHC(O)(CH$_2$)$_3$CH$_3$, and —(CH$_2$)$_y$C(O)OR$^5$ where y is 1 or 2 and R$^5$ is hydrogen, methyl, or tert-butyl.

22. The method according to claims 1, 2 or 3 wherein X is —C(O)Y wherein Y is selected from the group consisting of alkoxy and thioalkoxy.

23. The method according to claim 22 wherein Y is alkoxy selected from the group consisting of methoxy, ethoxy, n-propoxy, iso-propoxy, n-butoxy, iso-butoxy, and tert-butoxy.

24. The method according to claims 1, 2, or 3 wherein X is —C(O)Y and Y is —NR'R" where R' and R" are independently selected from the group consisting of hydrogen, alkyl, substituted alkyl, cycloalkyl, aryl, heteroaryl, heterocyclic, and where R' and R" are joined to form a cyclic group having from 2 to 8 carbon atoms optionally containing 1 to 2 additional heteroatoms selected from the group consisting of oxygen, sulfur and nitrogen and optionally substituted with one or more alkyl or alkoxy groups.

25. The method according to claim 24 wherein Y is selected from the group consisting of amino (—NH$_2$), N-(iso-butyl)amino, N-methylamino, N,N-dimethylamino, and N-benzylamino.

26. The method according to claims 1, 2 or 3 wherein X is —CH$_2$OH.

27. The method according to claims 1, 2 or 3 wherein the compound of formula I is selected from the group consisting of:

N-[N-(3,4-dichlorophenyl)alanyl]valine methyl ester
N-[N-(3,4-dichlorophenyl)alanyl]valine N-iso-butyl amide
N-[N-(3,4-dichlorophenyl)alanyl]threonine methyl ester
N-[N-(3,4-dichlorophenyl)alanyl]valine ethyl ester
N-[N-(3,4-dichlorophenyl)alanyl]valine tert-butyl ester
N-[N-(3,4-dichlorophenyl)alanyl]valine amide
N-(3,4-dichlorophenyl)alanine N-(1-hydroxy-3-methyl-2-butyl)amide
N-[N-(3,4-dichlorophenyl)alanyl]valine N,N-dimethyl amide
N-[N-(3,4-dichlorophenyl)alanyl]valine N-methyl amide
N-[N-(3,4-dichlorophenyl)alanyl]alanine methyl ester
N-[N-(3,4-dichlorophenyl)alanyl]leucine methyl ester
N-[N-(3,4-dichlorophenyl)alanyl]phenylalanine methyl ester
N-[N-(3,4-dichlorophenyl)alanyl]isoleucine methyl ester
N-[N-(3,4-dichlorophenyl)alanyl]-2-aminopentanoic acid methyl ester
N-[N-(3,4-dichlorophenyl)alanyl]-2-aminohexanoic acid methyl ester
N-[N-(3,4-dichlorophenyl)alanyl]tryptophan methyl ester
N-[N-(3,4-dichlorophenyl)alanyl]aspartic acid α-methyl ester
N-[N-(3,4-dichlorophenyl)alanyl]aspartic acid β-(tert-butyl ester)α-methyl ester
N-[N-(3,4-dichlorophenyl)alanyl]-N-BOC-lysine methyl ester
N-[N-benzothiazol-6-yl)alanyl]-2-aminohexanoic acid methyl ester
N-[N-(3,4-dichlorophenyl)alanyl]lysine methyl ester
N-[N-(3,4-dichlorophenyl)alanyl]tyrosine methyl ester
N-[N-(3,5-dichlorophenyl)alanyl]alanine methyl ester
N-[N-(3,5-dichlorophenyl)alanyl]-2-aminopentanoic acid methyl ester
N-[N-(3,5-dichlorophenyl)alanyl]phenylalanine methyl ester
N-[N-(3,4-dichlorophenyl)alanyl]aspartic acid β-(methyl ester)α-methyl ester
N-[N-(3,4-dichlorophenyl)alanyl]-1-benzylhistidine methyl ester
N-[N-(3,4-dichlorophenyl)alanyl]glutamic acid γ-(tert-butyl ester)α-methyl ester
N-[N-(3,4-dichlorophenyl)alanyl]leucine amide
N-[N-(3,4-dichlorophenyl)alanyl]glutamic acid α-methyl ester
N-[N-(3,4-dichlorophenyl)alanyl]-(3,5-diiodo)tyrosine methyl ester
N-[N-(3,4-dichlorophenyl)alanyl]-(3-iodo)tyrosine methyl ester
N-[N-(3,5-dichlorophenyl)glycyl]-2-aminopentanoic acid methyl ester
N-[N-(3,4-dichlorophenyl)alanyl]-Nε-(hexanoyl)lysine methyl ester N-[N-(3,4-dichlorophenyl)alanyl]phenylalanine amide
N-[N-(3,4-dichlorophenyl)alanyl-]2-aminohexan-(N-methyl)-amide
N-[N-(3,4-dichlorophenyl)alanyl-]β-cyclohexylalanine methyl ester
N-[N-(3,4-dichlorophenyl)alanyl]-2-aminohexanamide
N-[N-(3,4-dichlorophenyl)alanyl]-2-aminohexan-(N,N-dimethyl)-amide
N-[N-(3,4-dichlorophenyl)alanyl]methionine methyl ester
N-[N-(3,5-dichlorophenyl)alanyl]-2-aminohexan-(N,N-dimethyl)-amide
N-[N-(3,5-dichlorophenyl)alanyl]-2-aminohexanamide
N-[N-(3,5-dichlorophenyl)alanyl]-2-aminohexan-(N-methyl)-amide
N-[N-(3,4-dichlorophenyl)alanyl]histidine methyl ester
N-[N-(quinolin-3-yl)alanyl]-2-aminohexanoic acid methyl ester
N-[N-(benzothiazol-2-yl)-L-alanyl]-2-aminohexanoic acid methyl ester
N-[N-(3,5-difluorophenyl)alanyl]alanine methyl ester
N-[N-(3,5-difluorophenyl)alanyl]-2-aminohexanoic acid methyl ester
N-[N-(3,4-dichlorophenyl)-L-alanyl]-S-2-aminohexanamide
N-[N-(3,4-dichlorophenyl)alanyl]-2-aminohexan-(N-benzyl)-amide
N-[N-(3,4-dichlorophenyl)-D,L-alanyl]-2-amino-2-phenylethanol
N-[N-(3,5-dichlorophenyl)phenylglycinyl]alanine methyl ester
N-[N-(3,4-dichlorophenyl)alanyl]-2-aminohexanol
N-[N-(3,5-dichlorophenyl)alanyl]-2-amino-2-phenylethanol
N-[N-(3,5-dichlorophenyl)-L-alanyl]-L-phenylglycine tert-butyl ester
N-[N-(3,5-di-(trifluoromethyl)phenyl)-L-alanyl]-L-phenylglycine tert-butyl ester
N-[N-(3,5-dimethoxyphenyl)-L-alanyl]-2-aminohexanoic acid methyl ester and pharmaceutically acceptable salts thereof.

* * * * *